US010634665B2

(12) United States Patent
Iyer et al.

(10) Patent No.: US 10,634,665 B2
(45) Date of Patent: Apr. 28, 2020

(54) BIO-ASSESSMENT DEVICE AND METHOD OF MAKING THE DEVICE

(71) Applicants: Triad National Security, LLC, Los Alamos, NM (US); Vanderbilt University, Nashville, TN (US)

(72) Inventors: Rashi Iyer, Los Alamos, NM (US); Jen-Huang Huang, Los Alamos, NM (US); Pulak Nath, Los Alamos, NM (US); Jennifer Harris, Los Alamos, NM (US); John P. Wikswo, Jr., Brentwood, TN (US)

(73) Assignees: Triad National Security, LLC, Los Alamos, NM (US); Vanderbilt University, Nashville, TN (US)

( * ) Notice: Subject to any disclaimer, the term of this patent is extended or adjusted under 35 U.S.C. 154(b) by 0 days.

(21) Appl. No.: 15/513,949

(22) PCT Filed: Sep. 24, 2015

(86) PCT No.: PCT/US2015/052039
§ 371 (c)(1),
(2) Date: Mar. 23, 2017

(87) PCT Pub. No.: WO2016/049363
PCT Pub. Date: Mar. 31, 2016

(65) Prior Publication Data
US 2017/0307594 A1    Oct. 26, 2017

Related U.S. Application Data

(60) Provisional application No. 62/054,843, filed on Sep. 24, 2014, provisional application No. 62/160,510, (Continued)

(51) Int. Cl.
*C12M 3/00* (2006.01)
*C12M 1/00* (2006.01)
(Continued)

(52) U.S. Cl.
CPC ........ *G01N 33/5064* (2013.01); *B01L 3/5027* (2013.01); *B01L 3/50273* (2013.01);
(Continued)

(58) Field of Classification Search
CPC ...... C12M 25/02; C12M 21/08; C12M 23/42; C12M 23/44; C12M 41/30; C12M 41/34
See application file for complete search history.

(56) References Cited

U.S. PATENT DOCUMENTS

| 5,633,162 A | 5/1997 | Keen |
| 6,197,575 B1 | 3/2001 | Griffith et al. |

(Continued)

FOREIGN PATENT DOCUMENTS

| WO | WO-2008100559 A2 * | 8/2008 |
| WO | WO 2013/085909 | 6/2013 |

(Continued)

OTHER PUBLICATIONS

Huh et al. Acoustically Detectable Cellular-Level Lung Injury Induced by Fluid Mechanical Stresses in Microfluidic Airway Systems; PNAS, vol. 104, No. 48, pp. 18886-18891. (Year: 2007).*
(Continued)

*Primary Examiner* — Nathan A Bowers
(74) *Attorney, Agent, or Firm* — Klarquist Sparkman, LLP

(57) ABSTRACT

Disclosed herein are embodiments of a device that can be used to mimic the biochemical and physiological actions of a lung organ. Also disclosed herein are embodiments of components that are included in the device as well as methods of making and using the device. Further disclosed are platform device embodiments and various components used therein that can be used in combination with the lung organ devices disclosed herein. In some embodiments, the disclosed devices can be used to determine drug toxicity and
(Continued)

also can be used with one or more disease models to determine methods of treating disease.

17 Claims, 50 Drawing Sheets

Related U.S. Application Data filed on May 12, 2015, provisional application No. 62/212,268, filed on Aug. 31, 2015.

(51) Int. Cl.
| | |
|---|---|
| *G01N 33/50* | (2006.01) |
| *B01L 3/00* | (2006.01) |
| *C12N 5/07* | (2010.01) |
| *F16K 7/04* | (2006.01) |
| *C12N 5/071* | (2010.01) |

(52) U.S. Cl.
CPC ... *B01L 3/502707* (2013.01); *B01L 3/502715* (2013.01); *B01L 3/502738* (2013.01); *C12N 5/06* (2013.01); *G01N 33/5014* (2013.01); *G01N 33/5082* (2013.01); *B01L 2200/027* (2013.01); *B01L 2300/0627* (2013.01); *B01L 2300/0681* (2013.01); *B01L 2300/0832* (2013.01); *B01L 2300/0887* (2013.01); *B01L 2300/123* (2013.01); *B01L 2400/0481* (2013.01); *B01L 2400/0633* (2013.01); *C12N 5/067* (2013.01); *F16K 7/045* (2013.01); *G01N 33/5008* (2013.01)

(56) References Cited

U.S. PATENT DOCUMENTS

| | | | |
|---|---|---|---|
| 6,900,056 | B2 | 5/2005 | Lee et al. |
| 7,863,035 | B2 | 1/2011 | Clemens et al. |
| 8,278,419 | B2 | 10/2012 | Jacobs |
| 8,580,546 | B2 | 11/2013 | Gonda et al. |
| 2005/0051449 | A1 | 3/2005 | Jeter |
| 2005/0130292 | A1 | 6/2005 | Ahn et al. |
| 2007/0276508 | A1 | 11/2007 | Fischer et al. |
| 2010/0240086 | A1* | 9/2010 | Kashanin .......... B01L 3/502753 435/29 |
| 2010/0303687 | A1 | 12/2010 | Blaga et al. |
| 2011/0215107 | A1 | 9/2011 | Lee |
| 2012/0074062 | A1 | 3/2012 | Jovanovic et al. |
| 2012/0135452 | A1 | 5/2012 | Shuler et al. |
| 2012/0263631 | A1 | 10/2012 | Masters et al. |
| 2013/0273643 | A1 | 10/2013 | Vickers et al. |
| 2013/0309677 | A1 | 11/2013 | Blackman et al. |
| 2014/0170693 | A1 | 6/2014 | Ince |
| 2014/0356849 | A1 | 12/2014 | Wikswo et al. |
| 2015/0004077 | A1 | 1/2015 | Wikswo et al. |
| 2018/0355299 | A1* | 12/2018 | Guenat ................. C12M 21/08 |

FOREIGN PATENT DOCUMENTS

| | | |
|---|---|---|
| WO | WO 2013/086329 | 6/2013 |
| WO | WO 2013/086486 | 6/2013 |
| WO | WO 2013/086505 | 6/2013 |
| WO | WO 2013/181656 | 12/2013 |
| WO | WO 2014/081840 | 5/2014 |
| WO | WO 2014/127250 | 8/2014 |
| WO | WO 2015/006751 | 1/2015 |
| WO | WO 2015/138032 | 9/2015 |
| WO | WO 2015/138034 | 9/2015 |

OTHER PUBLICATIONS

Douville et al. Combination of Fluid and Solid Mechanical Stresses Contribute to Cell Death and Detachment in a Microfluidic Alveolar Model; Lab on a Chip, vol. 11, pp. 609-619. (Year: 2011).*

International Search Report and Written Opinion issued for International Application No. PCT/US2015/52043 dated Jan. 21, 2016 (12 pages).

International Search Report and Written Opinion issued for International Application No. PCT/US2015/052039 dated Dec. 22, 2015 (12 pages).

International Search Report and Written Opinion issued for International Application No. PCT/US2015/052046 dated Nov. 12, 2015 (11 pages).

Tavana et al., "Microfluidics, Lung Surfactant, and Respiratory Disorders," *LabMedicine*, 40(4): 204-209, Apr. 2009.

\* cited by examiner

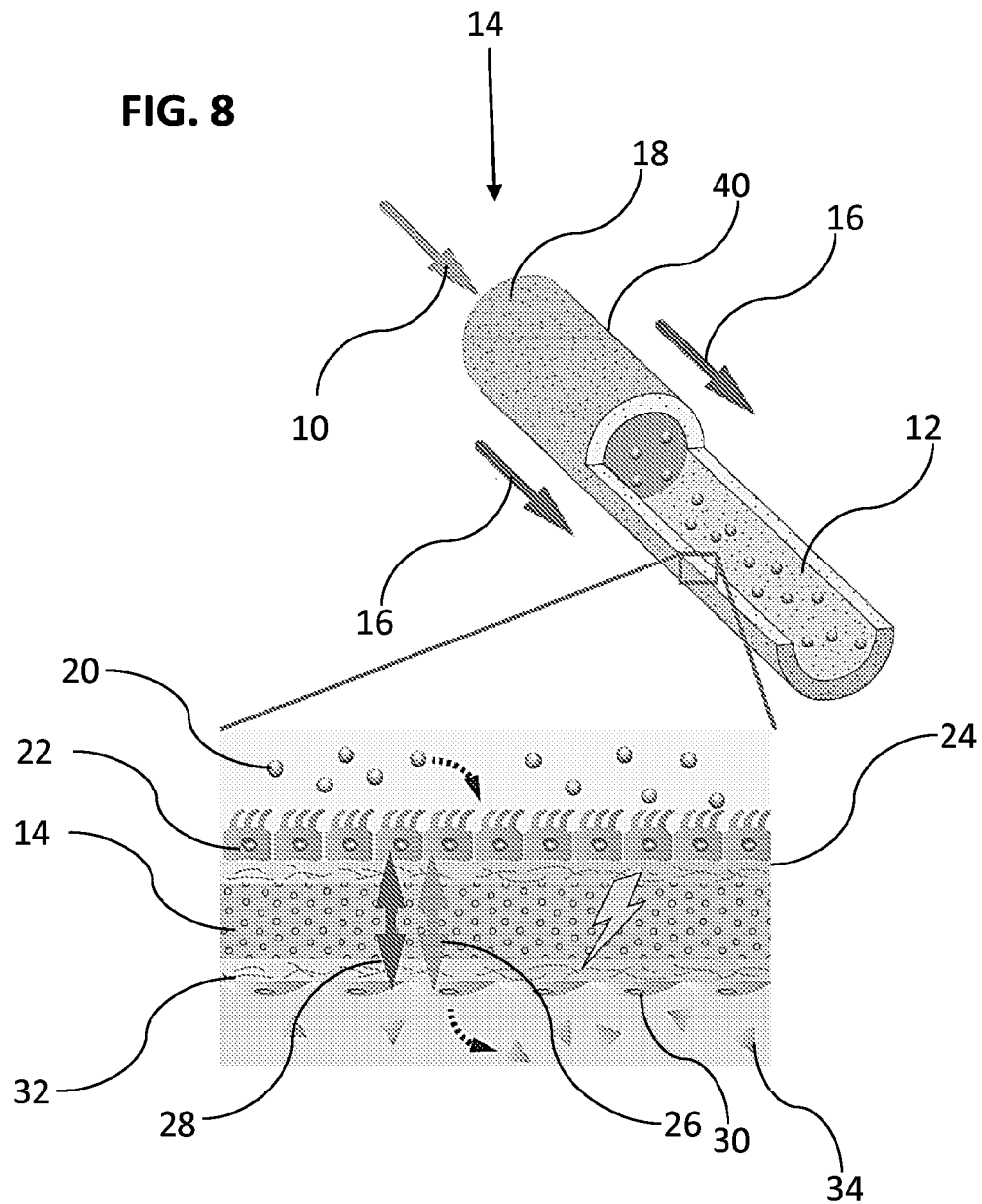

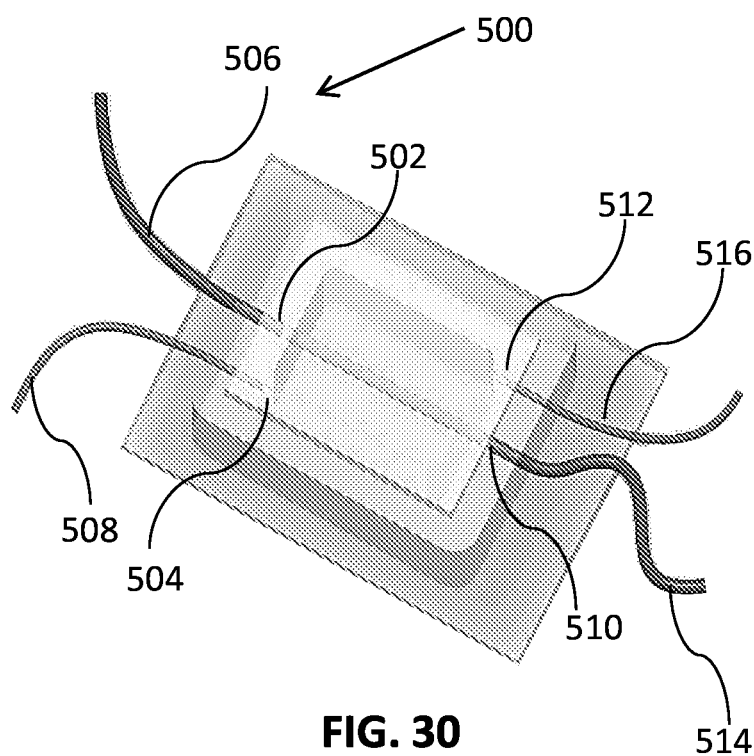
FIG. 30
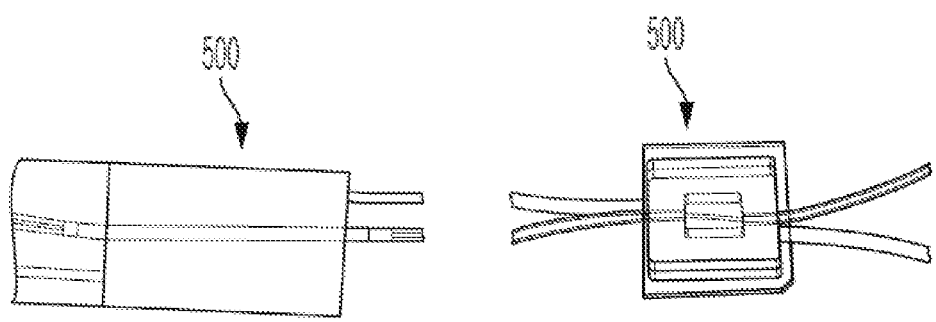
FIG. 31
FIG. 32
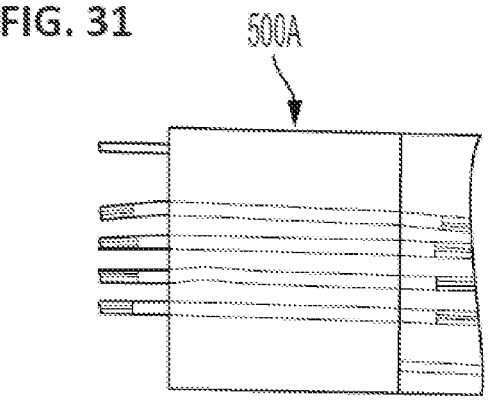
FIG. 33

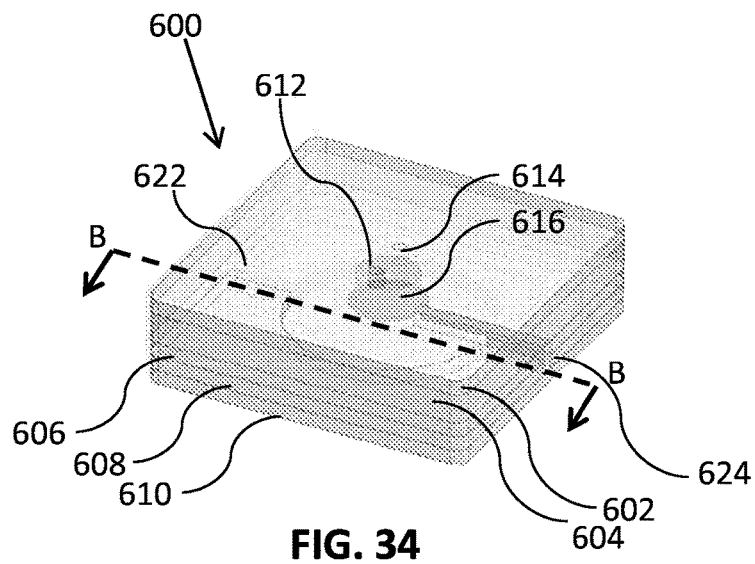
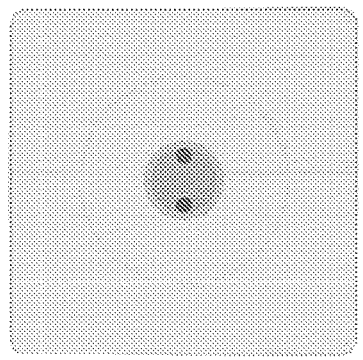
FIG. 34
FIG. 35
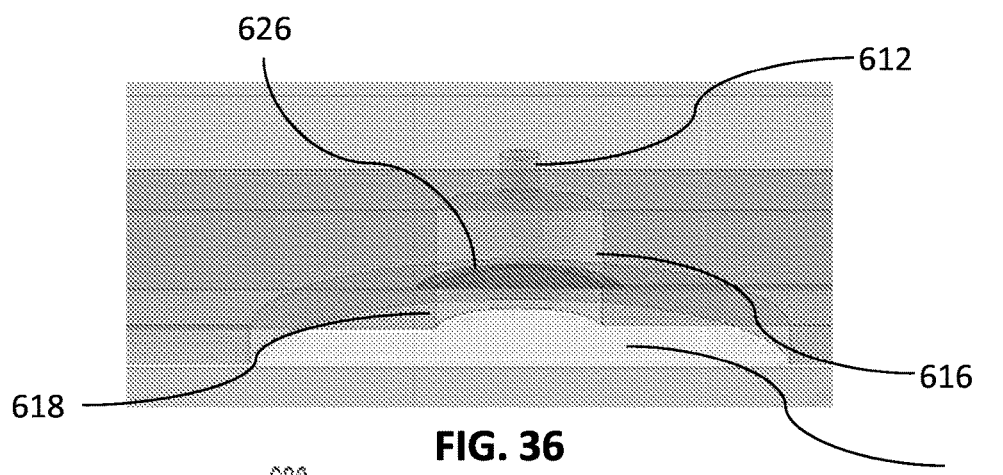
FIG. 36
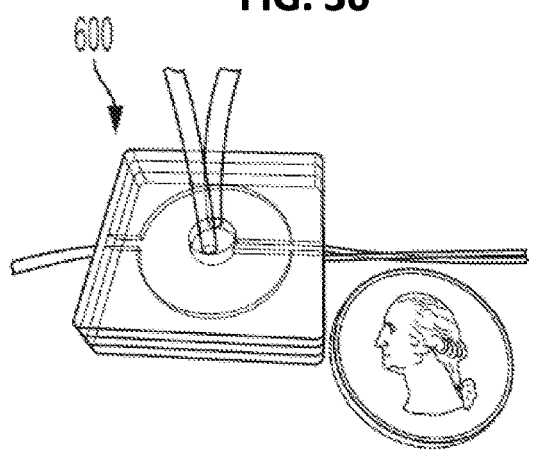
FIG. 37

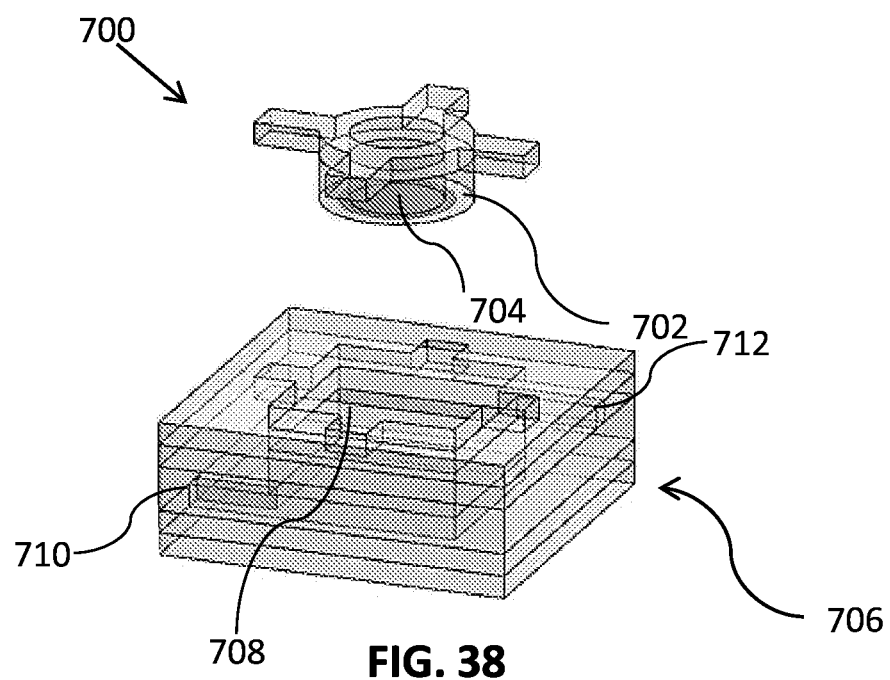
FIG. 38
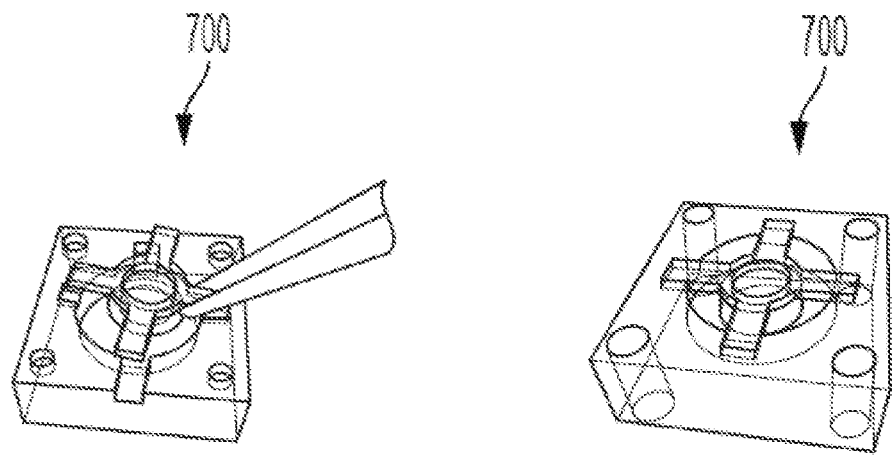
FIG. 39
FIG. 40

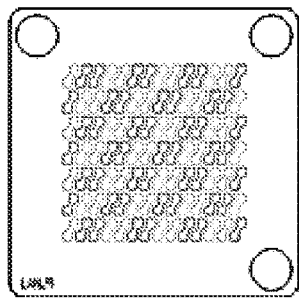 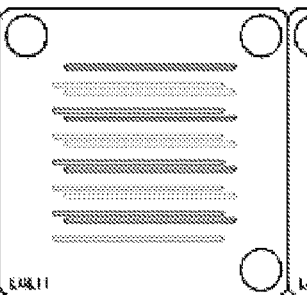 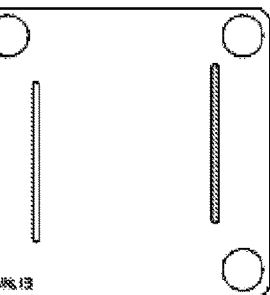 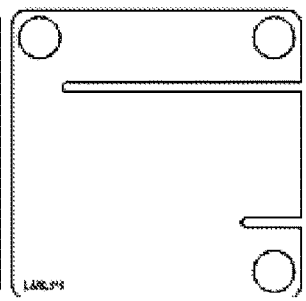
FIG. 60A     FIG. 60B     FIG. 60C     FIG. 60D
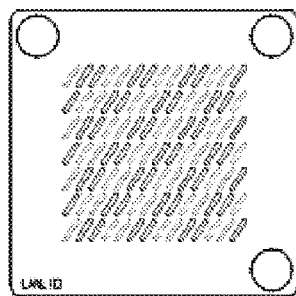 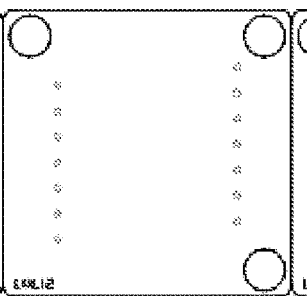 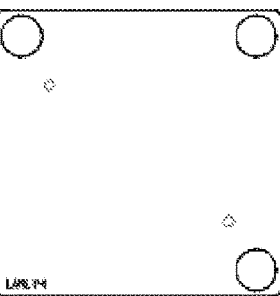 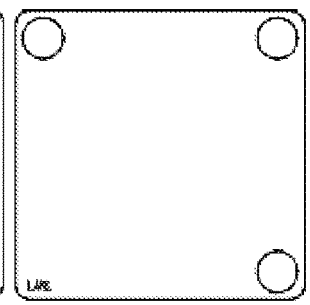
FIG. 60E     FIG. 60F     FIG. 60G     FIG. 60H

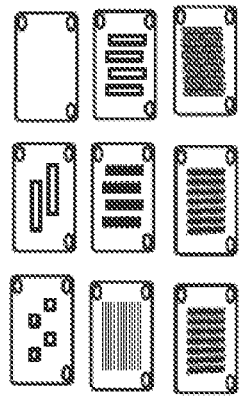
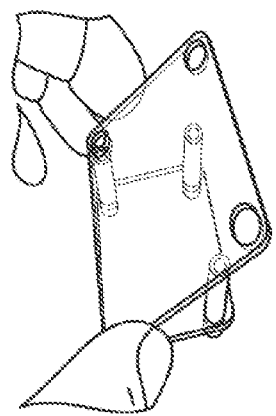
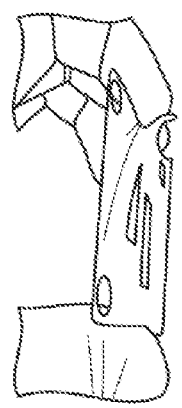
FIG. 78A          FIG. 78B          FIG. 78C
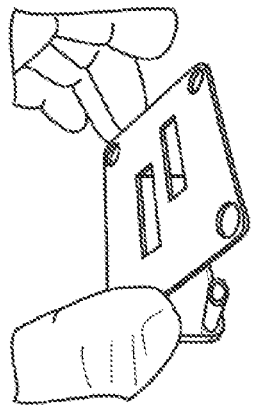
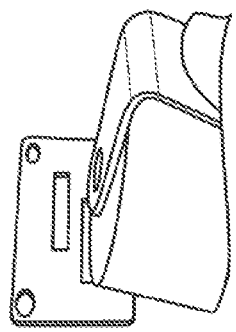
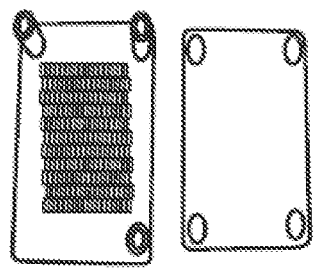
FIG. 78D          FIG. 78E          FIG. 78F
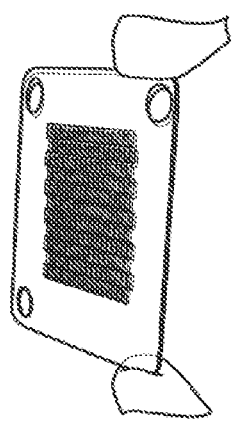
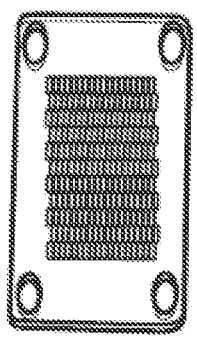
FIG. 78G          FIG. 78H

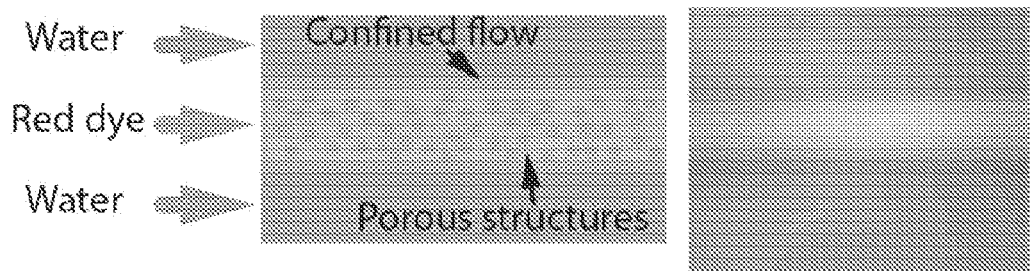
FIG. 85
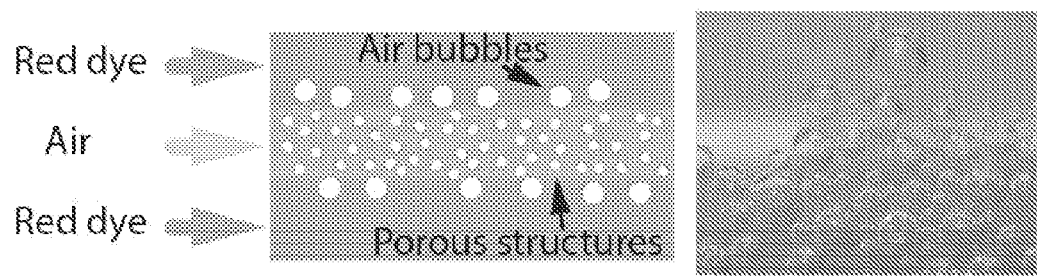
FIG. 86
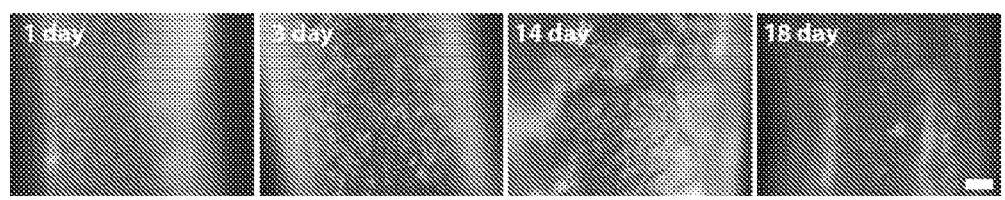
FIG. 87A  FIG. 87B  FIG. 87C  FIG. 87D
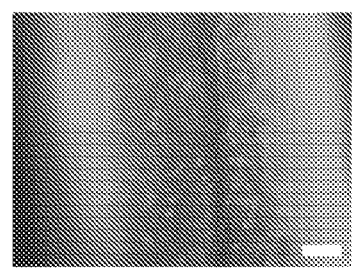
FIG. 87E

BIO-ASSESSMENT DEVICE AND METHOD OF MAKING THE DEVICE

CROSS REFERENCE TO RELATED APPLICATIONS

This application is the U.S. National Stage of International Application No. PCT/US2015/052039, filed on Sep. 24, 2015, which was published in English under PCT Article 21(2), which in turn claims the benefit of U.S. Provisional Application No. 62/054,843, filed Sep. 24, 2014; U.S. Provisional Application No. 62/160,510, filed May 12, 2015; and U.S. Provisional Application No. 62/212,268, filed Aug. 31, 2015, all of which are incorporated herein by reference in their entirety.

ACKNOWLEDGMENT OF GOVERNMENT SUPPORT

This invention was made with government support under Contract No. DE-AC52-06NA25396, awarded by the U.S. Department of Energy; and grant number R-00284-12-0, awarded by the Defense Threat Reduction Agency (DTRA). The government has certain rights in the invention.

FIELD

The present disclosure concerns embodiments of a device, which can be used to mimic lung function for testing and biological analysis.

BACKGROUND

Coupled systems of in vitro microfabricated organs-on-a-chip containing small populations of human cells are being developed to address the pharmacological and physiological gaps between monolayer cell cultures, animal models, and humans. These gaps present challenges not only in tissue and microfluidic engineering, but also in systems biology. For example, it must be determined how to model, test, and learn about the communication and control of biological systems at the scale of individual organs on chips. Allometric scaling provides some guidance, but appropriate biochemical and functional scaling of multiple organs and a universal cell-culture medium are also important to proper systems function and valid pharmacological interpretation.

Organ-on-a-chip technologies have advanced considerably in the past decade; however, understanding of biological scaling laws and how they apply to multiple, coupled organ devices has been largely ignored. To replicate human physiology and drug response with interconnected human organs-on-a-chip and larger human-like organ devices, each construct should have the correct relative size. Extensive literature describes differences in organ size between animal species whose body mass, M, spans 6 orders of magnitude. Organ size does not scale proportionally (isometrically) with M, but instead obeys a number of different allometric power laws that describe, for example, how as the animal's linear dimension L increases, its mass increases as $L^3$, and hence the cross-sectional area of the bones must increase out of linear proportion. Metabolic rates scale as $M^{3/4}$, blood circulation time scales as $M^{1/4}$, and pulmonary and vascular networks exhibit $M^{3/4}$ scaling (West et al., Science 276:122, 1997).

As organ devices are made smaller, scaling will ultimately fail, since individual cells have a fixed size, and immune cells, for example, function in isolation and at low densities. It is difficult to replicate the diameter of microcapillaries in tissue. The circulating volume of perfusate of an organ construct system must match organ size, lest metabolites, hormones, and paracrine signals be diluted to the point that each organ operates in a large reservoir independent of the other organs. Cellular heterogeneity, important to cellular signaling pathways in vivo, can be hard to maintain for long times in vitro. A universal media/blood surrogate is also needed to maintain multiple cell types, since most human cells are grown in media specific to the cell type and desired phenotype. Furthermore, devices should be mechanically and/or fluidly coupled and include sensing devices that can be used to evaluate the effects of compounds as they pass through each device.

The lung serves several physiological functions, and while its primary function is to enable optimal gas exchange, it is also involved in metabolic and immunological regulation. This functional complexity is reflected in its unique architecture that, to date has been difficult to simulate. A primary challenge in simulating the lung is the development of a scaffold that supports tissue growth while also simulating the structural characteristics of the lung. Although advances have been made in the art, the final goal of engineering and forming an in vitro lung organ mimic has not yet been realized.

Several limitations to traditional lung organ platforms include, but are not limited to, the inability to simulate the orientation or expansion of alveoli, the inability to develop a comprehensive lung organ platform (e.g., rather than just a small scale alveolar unit), the inability to incorporate pulmonary cells and microvascular cells into the device, the inability to temporarily support in vitro pulmonary gas exchange, the inability to restore pulmonary function for suitable periods of time (e.g., after implantation into an animal), uneven cell differentiation, poor vascular endothelial coverage efficiency, inefficient transport of dissolved oxygen and nutrients through the interior of organ tissue, and circulation leakage. Additionally, current approaches for determining drug toxicity in the art have only been tested on animal models, and data derived from human cell-based pulmonary organ is extremely limited.

Another challenge in the development of the lung organ is the differentiation of cells into the correct population dynamics to emulate lung diversity. Current techniques used in the art to achieve this goal produce low yields of pulmonary cells on three-dimensional (3D) synthetic scaffolds and also lack functional assembly of alveolar-like structures.

SUMMARY

A need exists in the art for a device that can more accurately mimic lung function and also provide an environment similar to that of a lung for test purposes, such as for drug toxicology screening, disease modeling, and the like. Disclosed herein are devices that can more accurately mimic lung function and also provide an environment similar to that of a lung for test purposes, such as for drug toxicology screening, disease modeling, and the like. In some embodiments, the device comprises a bronchiolar device and at least one alveolar device, wherein the bronchiolar device and the at least one alveolar device are fluidly coupled together.

In some embodiments, the lung organ device comprises a first substrate comprising a first plurality of channels and a second substrate comprising a second plurality of channels, wherein the first plurality of channels and the second plurality of channels are fluidly coupled, and further comprising a bronchiolar membrane positioned between the first substrate and the second substrate; and at least one alveolar device, wherein the bronchiolar device and the at least one alveolar device are fluidly coupled together.

In any or all of the above embodiments, the bronchiolar device comprises the following components: a first substrate configured to comprise a first inlet; a second inlet; at least one channel fluidly coupled to the first inlet; a first outlet fluidly coupled to the first inlet; a second outlet fluidly coupled to the second inlet; at least two fluid ports; and at least one channel fluidly coupled to one of the at least two fluid ports.

In any or all of the above embodiments, the bronchiolar device can further comprise a second substrate configured to comprise the following components: a first port fluidly coupled to the first inlet of the first substrate through at least one port of the first substrate; a second fluid port fluidly coupled to the second inlet of the first substrate; at least one channel fluidly coupled to the second fluid port; a third fluid port fluidly coupled to the first outlet of the first substrate; and a fourth fluid port fluidly coupled to the second outlet of the first substrate.

In some embodiments, the bronchiolar device can comprise a tube platform comprising at least one hollow tube fluidly coupled to the first inlet and at least one fluid port of the first substrate rather than a bronchiolar membrane. In any or all of the above embodiments, the first substrate comprises a first fluid port and a second fluid port. In any or all of the above embodiments, the first substrate can further comprise an incubation chamber fluidly coupled to the second inlet and the second fluid port. The second fluid port is fluidly coupled to the at least one channel fluidly coupled to the first inlet. In any or all of the above embodiments, the first substrate is positioned on top of the bronchiolar membrane and the second substrate is placed below the bronchiolar membrane. In any or all of the above embodiments, the membrane comprises a porous material, such as poly-L-lactic acid. In any or all of the above embodiments, the bronchiolar membrane can comprise an endothelial side that is or can be associated with endothelial cells and an epithelial side that is or can be associated with epithelial cells. In any or all of the above embodiments, the endothelial cells can be lung microvascular endothelial cells selected from HLMVE cells and wherein the epithelial cells are selected from BEAS-2B bronchial epithelial cells. In any or all of the above embodiments, the bronchiolar membrane includes a plurality of fluid ports that align with one or more of the at least two fluid ports of the first substrate of the bronchiolar device.

In some embodiments, the bronchiolar device comprises a first plurality of channels in the first substrate that are arranged in a branching configuration. In some embodiments, the bronchiolar device comprises a second plurality of channels in the second substrate that are arranged in a branching configuration.

In some embodiments using a tube platform, the hollow tubes of the tube platform comprise a central lumen having a diameter of 0.6 mm to 1 mm and an elongated body having an outer diameter ranging from 1 mm to 1.2 mm. The hollow tubes also comprise one or more pores capable of allowing fluids, or components contained therein, to pass between the central lumen and an environment exterior to the elongated body. In any or all of the above embodiments, the central lumen is associated with a first population of cells and the elongated body is associated with a second population of cells. The first population of cells and the second population of cells are different in some embodiments. In particular disclosed embodiments, the first population of cells comprises bronchial epithelial cells and the second population of cells comprises lung microvascular endothelial cells.

The alveolar device can comprise a fluid-compatible component comprising a plurality of substrates coupled together, a first fluid inlet fluidly coupled to the first inlet of the first substrate, and a first fluid outlet fluidly coupled to the first outlet of the first substrate; a medium-compatible component comprising a plurality of substrates coupled together, a second fluid inlet fluidly coupled to the second inlet of the first substrate, and a second fluid outlet fluidly coupled to the second outlet of the first substrate; and a alveolar membrane component positioned between and fluidly coupled to the fluid-compatible component and the medium-compatible component, wherein the alveolar membrane component comprises a membrane material coupled to a substrate comprising a plurality of apertures. In some embodiments, the plurality of substrates of the fluid-compatible component and the medium-compatible component comprises substrates comprising one or more channels. Each of the one or more channels can be microchannels or nanochannels. In some embodiments, the membrane material of the alveolar membrane component is selected to resiliently deform and reform and can be a material that allows gas exchange between the fluid-compatible component and the medium-compatible component. In particular disclosed embodiments, the membrane material comprises poly-L-lactic acid or a polydimethylsiloxane.

In some embodiments, one side of the alveolar membrane material is associated with a first population of cells and the other side of the membrane material is associated with a second population of cells. The first population of cells is associated with a side of the membrane material that is fluidly coupled with the fluid-compatible component and the second population of cells is associated with a side of the membrane material that is fluidly coupled with the medium-compatible component. For example, the first population of cells can comprise immune responsive cells, surfactant-producing cells, or a combination thereof and the second population of cells can comprise pulmonary microvascular cells. In exemplary embodiments, the first population of cells comprises AT1 cells, AT2 cells, or a combination thereof and the second population of cells comprises human lung microvascular endothelial cells, human lung smooth muscle cells, human lung fibroblast cells, monocytes, dendritic cells, or a combination thereof.

Also disclosed herein are embodiments of a platform device, comprising an air source fluidly coupled to a lung organ device as described herein; an organ perfusion system in fluid communication with a fresh media circuit (e.g., an arterial system) and a recirculation circuit (e.g., a venous system), wherein the fresh media circuit is fluidly coupled to the device and the recirculation circuit is fluidly coupled to the lung organ device; one or more rotary peristaltic pumps capable of pumping fluid to one or more rotary planar valves; a perfusion controller in communication with the organ perfusion system; and optionally an analyzer, a sensor, or a combination thereof in communication with the perfusion controller.

In some embodiments, the platform device further comprises a heart device, a liver device, a kidney device, or a combination thereof. In any or all of the above embodiments, the heart device comprises a single heart device or a right heart device and a left heart device. In any or all of the above embodiments, the lung organ device is serially and fluidly coupled to the heart device. In any or all of the above embodiments, the lung organ device is positioned serially between the left heart device and the right heart device. In any or all of the above embodiments, the fresh media circuit and the recirculation circuit are fluidly coupled to the heart device, the liver device, the kidney device, or a combination thereof. In any or all of the above embodiments, the platform device can further comprise one or more microformulators fluidly coupled to the fresh media circuit and the recirculation circuit. In any or all of the above embodiments, the microformulator is a missing organ microformulator, a gut microformulator, or a combination thereof. In some embodiments, the gut microformulator is fluidly coupled to the fresh media circuit directly and is fluidly coupled to the recirculation circuit indirectly through the liver device. In any or all of the above embodiments, the platform device comprises one or more multichannel potentiostats.

Also disclosed herein are embodiments of a method comprising introducing a compound, or composition thereof, into a device as disclosed herein and analyzing a response generated by the device after the compound, or composition thereof, has been introduced into the device. In some embodiments, the compound, or composition containing a compound, is introduced into a bronchiolar device of the device, wherein the bronchiolar device is fluidly coupled to an alveolar device. In some embodiments, analyzing the response generated by the lung organ device comprises determining whether fluid leakage occurs in the device. In other embodiments, analyzing the response generated by the device comprises detecting an immune response produced by one or more cell populations associated with the membrane or hollow tube of the device. The method embodiments disclosed herein also can further comprise extracting a sample from the device and the extracted sample is analyzed to determine the presence or amount of at least one compound in some embodiments. The sample can be a fluid that passes through the bronchiolar device, the alveolar device, or both. The sample also can be a cell sample or a tissue sample from the device. In another embodiment, the method further comprises introducing the sample into a chromatograph, a mass spectrometer, or a combination thereof to detect the compounds within the sample.

The foregoing and other objects, features, and advantages of the disclosure will become more apparent from the following detailed description, which proceeds with reference to the accompanying figures.

BRIEF DESCRIPTION OF THE DRAWINGS

FIG. 8 is a schematic diagram illustrating fluid flow through a hollow tube embodiment and further illustrating activity that can occur between fluid in the central lumen of the hollow tube and fluid flowing past an elongated body of the hollow tube.

FIG. 9A shows cell seeding (at 25× magnification) on a basolateral side of a hollow tube using HLMVE cells and live/dead staining; FIG. 9B shows the cells of FIG. 9A at 100× magnification; FIG. 9C shows cell seeding (at 25× magnification) on an apical side of a hollow tube using BEAS-2B cells and live/dead staining; FIG. 9D shows the cells of FIG. 9C at 100× magnification; FIG. 9E shows cell cultures (after 6 days) of HLMVE cells on a basolateral side of a hollow tube using nucleus staining; FIG. 9F shows cell cultures (after 6 days) of HLMVE cells on a basolateral side of a hollow tube using live/dead staining; FIG. 9G shows cell cultures (after 6 days) of NHBE cells on an apical side of a hollow tube using nucleus staining; and FIG. 9H shows cell cultures (after 6 days) of NHBE cells on an apical side of a hollow tube using live/dead staining.

FIG. 10A shows NHBE cells seeded on a transwell membrane using alcian blue staining; FIG. 10B shows NHBE cells seeded on a transwell membrane using β-tubulin staining; FIG. 10C shows NHBE cells seeded on a transwell membrane using tight junction staining; and FIG. 10D NHBE cells seeded on a transwell membrane using H&E staining.

FIG. 30 illustrates an embodiment of a bronchiolar device comprising inlets and outlets that are positioned in a parallel orientation.

FIG. 31 shows a working example of the bronchiolar device illustrated in FIG. 30.

FIG. 32 shows another working example of the bronchiolar device illustrated in FIG. 30.

FIG. 33 show a working example of a bronchiolar device similar to that illustrated in FIG. 30, but further comprising a plurality of hollow tubes.

FIG. 34 illustrates another exemplary bronchiolar device comprising a membrane component coupled to an air chamber and a medium chamber.

FIG. 35 is a top view of the bronchiolar device illustrated in FIG. 34.

FIG. 36 is a cross-sectional view of the bronchiolar device taken along axis B-B, as illustrated in FIG. 35.

FIG. 37 shows a working example of the bronchiolar device illustrated in FIG. 34.

FIG. 38 illustrates another example of a bronchiolar device disclosed herein comprising a transwell portion and a well portion comprising a membrane component.

FIG. 39 shows a working example of the well portion and the transwell portion of the bronchiolar device illustrated in FIG. 38.

FIG. 40 shows a working example of an assembled bronchiolar device as illustrated in FIG. 38.

FIGS. 60A-60H illustrate embodiments of substrates that can be used to make a medium-compatible component of an alveolar device.

FIG. 61A illustrates a membrane material in a resting state and FIG. 61B illustrates the membrane material as it is influenced by air delivered into and out of the device.

FIGS. 78A-78H illustrate certain embodiments of the progression of steps used to make an alveolar device.

FIG. 84A is a graph of seeding flow rate (mL/min) vs. cell number (cells); FIGS. 84B and 84C are digital images of cells grown on a hollow tube after 1 day (FIG. 84B) and 3 days (FIG. 84C); FIGS. 84D and 84E are TEM images of cells grown on a hollow tube after 1 day (FIG. 84D) and 3 days (FIG. 84E); FIGS. 84F and 84G are digital images of cells grown on a hollow tube after 34 days.

FIG. 85 illustrates liquid flow between a porous hollow tube central lumen and the surrounding environment.

FIG. 86 illustrates air flow between a porous hollow tube central lumen and the surrounding environment.

FIGS. 87A-87E shows images of cells grown within a central lumen of a hollow tube after a time period of 1 day (FIG. 87A), 3 days (FIG. 87B), 14 days (FIG. 87C), and 18 days (FIG. 87D); FIG. 87E illustrates a central lumen prior to cell culture.

FIGS. 95-95D show drug toxicity results obtained from using a bronchiolar device embodiment described herein; FIGS. 95A-95D show images of fluorescent microbead deposition on a central lumen associated with cells.

DETAILED DESCRIPTION

I. Introduction

Figure 1:
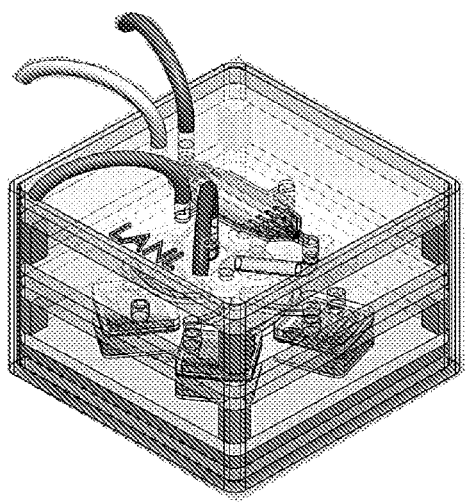
FIG. 1 illustrates an exemplary embodiment of a lung organ device comprising a plurality of alveolar devices in combination with a single bronchiolar device.

Embodiments of an in vitro lung organ device (also referred to as a lung bio-assessment device or a lung organ bio-assessment device) are disclosed herein, as well as methods of making and using the device. In some embodiments, the in vitro lung organ device can be a human lung organ bio-assessment device. In some embodiments, the lung organ device is incorporated in a platform device disclosed herein, such as a device including two or more fluidly coupled bio-assessment devices, including a lung bio-assessment device and at least one other organ device. The disclosed device embodiments disclosed herein can at least partially be used to replace expensive and time-consuming animal testing models for biomedical research, drug discovery, and threat agent analysis (e.g., drug toxicology) and thereby may reduce or even eliminate the need to extrapolate from animal models to human response, which often can be inaccurate.

A challenge to developing a lung organ construct (e.g., a lung bio-assessment device) is to reconstitute physiologically realistic microenvironments that are capable of maintaining cell differentiation and tissue-specific function. For example, in tissue culture experiments, primary human bronchiolar and alveolar epithelial cells do not differentiate into respiratory epithelium when submerged in culture medium. The disclosed lung bio-assessment devices, however, can overcome these limitations by integrating an air-liquid interface using, for example, a biocompatible material (e.g., porous hollow tubes, porous membranes, and/or elastic membranes) to mimic the physiological complexity associated with the lung bronchioles and alveoli. The two phase flow system embodiments disclosed herein can simulate a dynamic liquid layer at surfaces of the biocompatible materials (e.g., the surfaces of the hollow tubes (or membranes) used in the bronchiolar devices disclosed herein, and the apical side of membrane materials used in alveolar devices disclosed herein) by alternatively changing air and liquid flow rate. This capability can be harnessed to develop well-differentiated bronchiolar and alveolar lung tissue in the platform.

In some embodiments, the disclosed lung bio-assessment devices comprise a design that is physiologically similar to a lung, which can be fabricated using efficient methods, thereby making the disclosed devices more compatible than devices currently existing in the art. The disclosed devices can be scaled for use in small-scale applications and large-scale applications. Additionally, both bronchiolar and alveolar devices can be joined together to provide a complete lung organ platform. In some embodiments, an air-liquid interface can be integrated with the artificial lung bronchiole and alveoli devices using biocompatible porous hollow tubes and membrane components to mimic the physiological complexity for the growth of the lung bronchiole and alveoli devices.

Also disclosed herein are embodiments of a platform device that is used to couple the lung organ device to other bio-assessment devices mimicking other organs, such as a kidney, liver, heart, or the like. The platform device comprises a plurality of components that help facilitate fluid communication between each bio-assessment device and that can be used to deliver and monitor various drugs and/or toxins as they pass through each bio-assessment device thereby providing the ability to evaluate the efficacy of new drugs and/or the deleterious effects of toxins on the organs.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise. All references cited herein are incorporated by reference in their entirety.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

II. Lung Bio-Assessment Devices

Disclosed herein are embodiments of devices that can be used to mimic an in vivo lung organ (such as a human or other animal lung). In particular disclosed embodiments, the device can be an in vitro fluidic device (e.g., a microfluidic device) through which one or more types of fluid can flow. In particular disclosed embodiments, the device includes a bronchiolar device, an alveolar device, and combinations thereof, and can further include additional components that facilitate coupling and uses of these components. The bronchiolar device and the alveolar device can be assembled together to form a lung organ construct that simulates the function of a lung (such as a human or other animal lung organ). In particular disclosed embodiments, the device is capable of supporting growth, cultivation, differentiation, and/or function of one or more types of cells and/or tissue. In some embodiments, the lung organ devices disclosed herein can comprise a means for performing a bronchiolar function and a means for performing an alveolar function, wherein the means for performing a bronchiolar function is fluidly coupled to the means for performing an alveolar function.

The lung organ devices disclosed herein more accurately (that is, provide a response similar to that produced by a live lung organ) represent organ level responses, normal physiological activity (e.g., dynamic process of gas-exchange), and innate and adaptive immune responses as compared to devices previously used in the art or animal models used to assess such responses or activity.

The device embodiments disclosed herein are useful for toxicity testing of pharmaceutical compounds, disease state analysis, and other biomedical applications. Device embodiments disclosed herein therefore can in some instances be used to replace traditional devices used in the art and/or animal models typically relied on for in vitro and/or in vivo assays. The disclosed devices also provide benefits in comparison to other devices or lung models traditionally used in the art, such as low sample volume usage, fast response time, flexible design, the ability to integrate the device with other devices that mimic other parts of the a mammal's (e.g., a human's) anatomy, the ability to grow three-dimensional cultures, and the ability to create cellular microenvironments. Exemplary embodiments of the lung organ devices are illustrated in FIGS. 1-4 and are further described herein.

A. Bronchiole Devices

Disclosed herein are embodiments of a bronchiole device component that can be used in lung organ devices (e.g., in combination with an alveolar device component, such as those described herein). The bronchiole device component can be used to provide a biomimetic system that mimics lung function, particularly functions associated with bronchioles. For example, embodiments of the disclosed bronchiole device component can be used to mimic a bronchiole airway system of a lung to test for toxicity and/or efficacy of particular drugs, as well as to investigate various diseases, such as pulmonary disease.

Disclosed embodiments of the bronchiole device include cells, for example, cells that are grown, maintained, differentiated, and/or regenerated into tissue on the bronchiole device. In some embodiments, cells can be grown to form tissue that has a branched structure that mimics the shape and geometry of bronchioles of a lung in vivo. The bronchiole device embodiments also can be used in the disclosed lung organ device to provide a biological environment that mimics the bronchiole environment of a lung in vivo, such as by providing cells that can produce mucin and/or cells with cilia.

Some embodiments of the disclosed bronchiolar devices include a plurality of substrates, which are understood herein to refer to a surface having a top face and a bottom face and can include one or more channels, fluid ports, inlets, outlets, or chambers. The substrates can be made of any suitable polymeric material capable of being fabricated to include the particular components of the bronchiolar device, such as channels, inlets, outlets, and chambers. In particular disclosed embodiments, the substrates include a polymer material, such as polydimethylsiloxane (PDMS), and/or acrylic or polycarbonate materials. Each substrate can be made of the same or different material as each other substrates used in the device.

In some embodiments of the bronchiolar device, two or more substrates can be used. Exemplary embodiments include two substrates; however, more than two substrates (such as 3, 4, 5, or more substrates) can be used. In some embodiments, at least one substrate can be configured to include one or more inlets, outlets, ports, or a combination thereof that can be used to deliver or remove one or more fluids to the device. At least one of the substrates also includes an incubation chamber that can be fluidly coupled to the one or more inlets, outlets, fluid ports, or a combination thereof.

The term "incubation chamber," as used herein, is understood to encompass an opening or channel formed within a substrate that is fabricated to have dimensions ranging from 3 mm to 20 mm wide, 10 mm to 30 mm long, and 3 mm to 10 mm deep and is capable of accepting and containing a fluid within its boundaries. In some embodiments, however, the dimension of the chamber can be increased or decreased depending on the required application. The term "inlet," as used herein, refers to an opening in a substrate, or a connector attached to a substrate, that is used to introduce a fluid into any one or more of the devices disclosed herein. In some embodiments, the inlet may be a separate connector component that is coupled to an opening in a top or bottom substrate. The term "outlet," as used herein, refers to an opening in a substrate, or a connector attached to a substrate, that is used to expel or remove a fluid from any one or more of the devices disclosed herein. In some embodiments, the outlet can be a separate connector component that is coupled to an opening in a top or bottom substrate. The term "fluid ports," as used herein, is understood to refer to an opening formed in and through a substrate that is used to facilitate delivery of a fluid between substrates and/or between a bronchiolar device and an alveolar device.

In some embodiments, the device includes a second substrate that can be coupled to the first substrate. The second substrate includes one or more fluid ports that are fluidly coupled to the inlets, outlets, fluid ports, or a combination thereof, of the first substrate. In some embodiments, the second substrate includes one or more channels that can couple two or more fluid ports of the second substrate. In some embodiments, the channels can be microchannels or nanochannels. The term "microchannels," as used herein, is understood to refer to channels having dimensions less than 1 mm and greater than or equal to 1 µm. The term "nanochannels," as used herein, is understood to refer to channels having dimensions less than 1 µm and greater than or equal to 1 nm. In yet other embodiments, the channels can have dimensions less than 10 mm and greater than or equal to 1 mm. The fluid ports can be configured to align with one or more fluid ports of an alveolar device that can be coupled to the bronchiolar device. The bronchiolar devices also can include a tube platform comprising one or more hollow tubes that can facilitate fluid flow and cell growth. The term "tube platform," as used herein, is understood to mean a component that includes at least two substrates that hold in place a hollow tube or plurality of hollow tubes. The term "hollow tube," as used herein, is understood to mean an elongated body that includes at least a central lumen.

Figure 5:
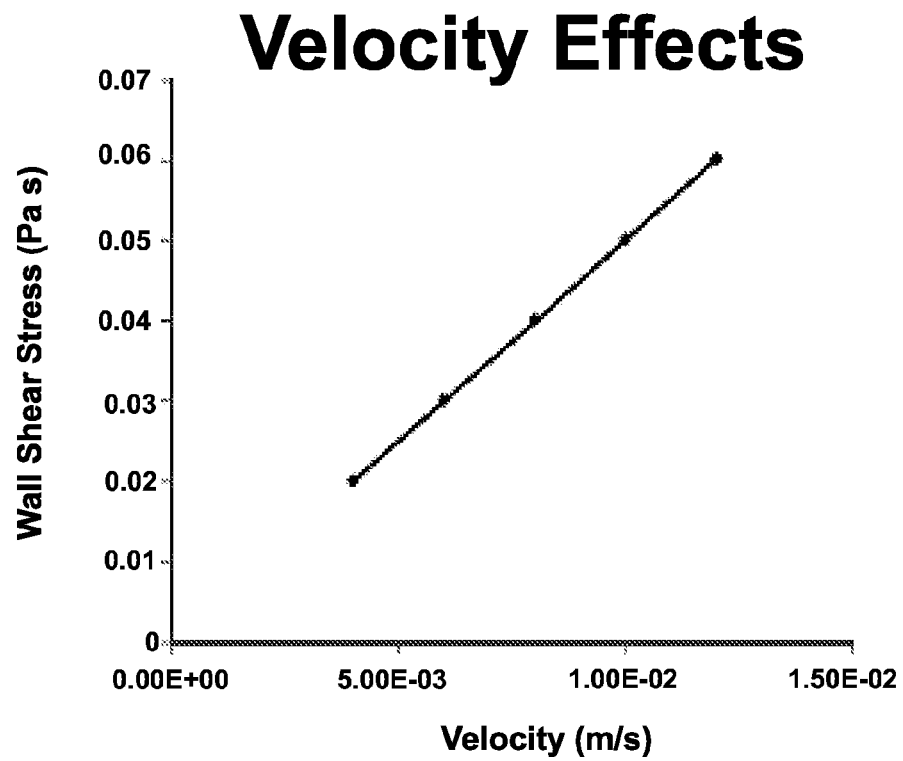
FIG. 5 is a graph of velocity (m/s) versus wall shear stress (Pa·s) illustrating velocity effects obtained from using embodiments of the hollow tubes disclosed herein.
Figure 6:
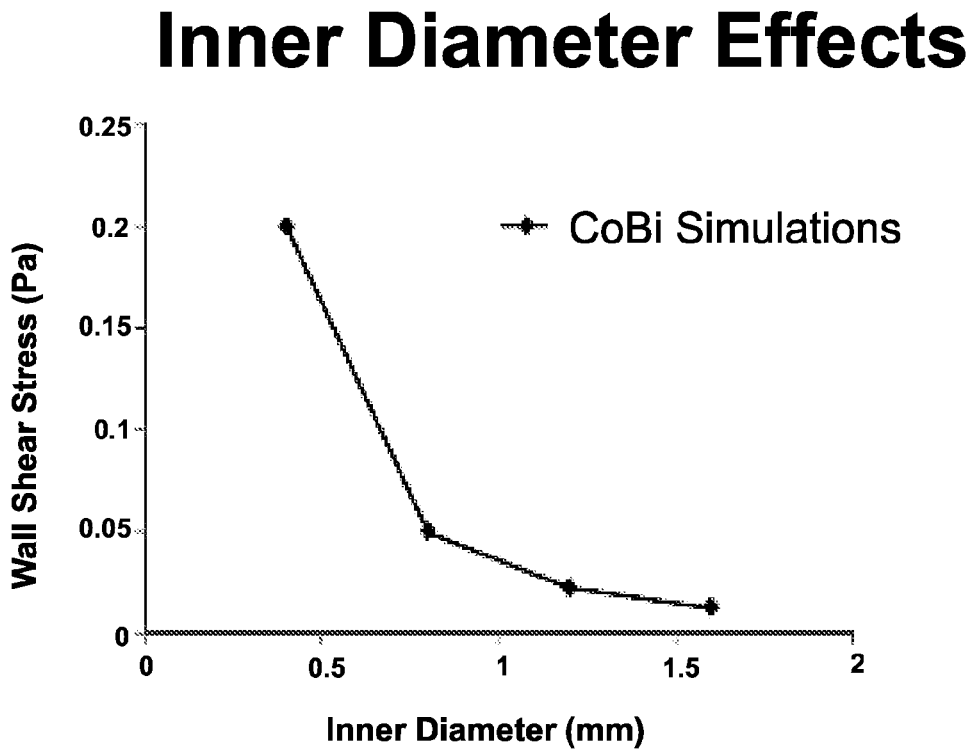
FIG. 6 is a graph of inner diameter (mm) versus wall shear stress (Pa) illustrating inner diameter effects of hollow tube embodiments disclosed herein.
Figure 7:
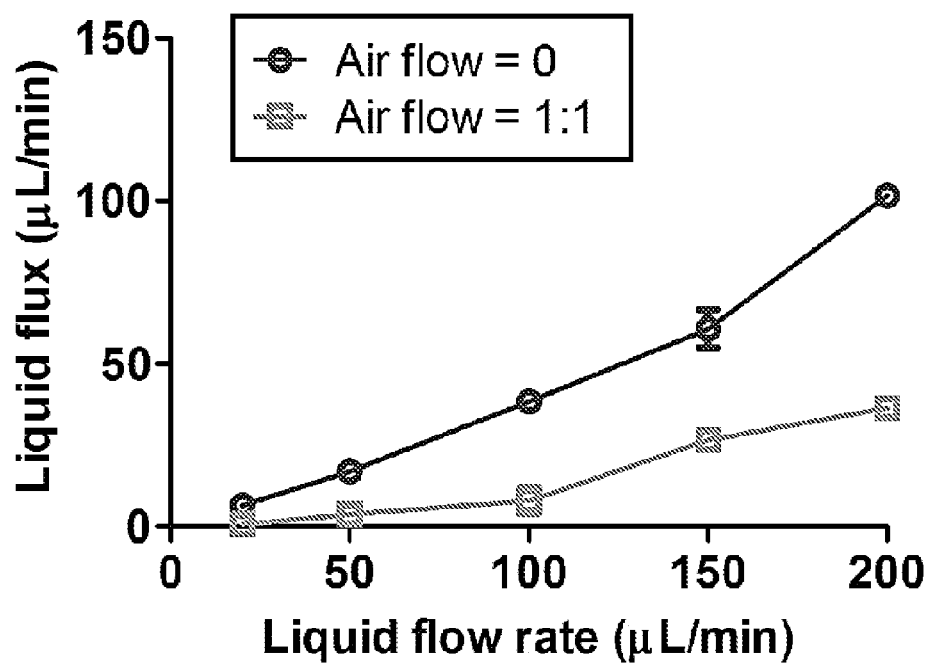
FIG. 7 is a graph of liquid flow rate (µL/min) versus liquid flux (µL/min) illustrating fluid flow characteristics of hollow tube embodiments disclosed herein.
Figure 9A:
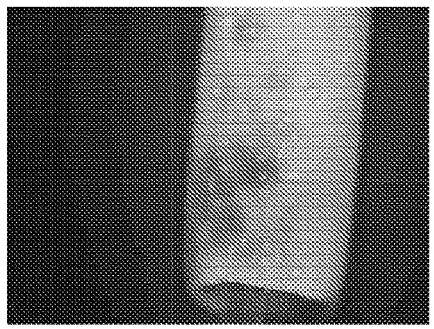
FIGS. 9A-9H are images of exemplary cell populations present on and within hollow tubes of a bronchiolar device embodiment.
Figure 9B:
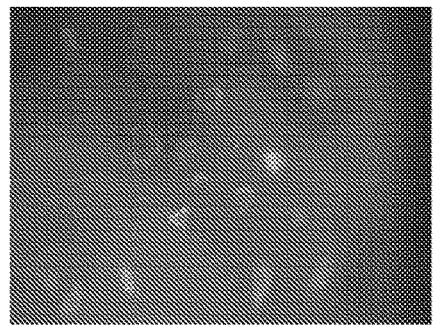
Figure 9C:
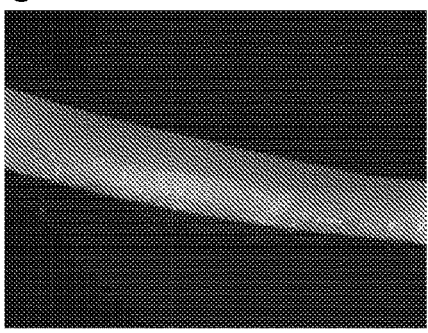
Figure 9D:
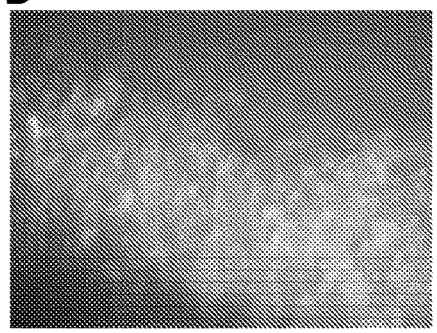
Figure 9E:
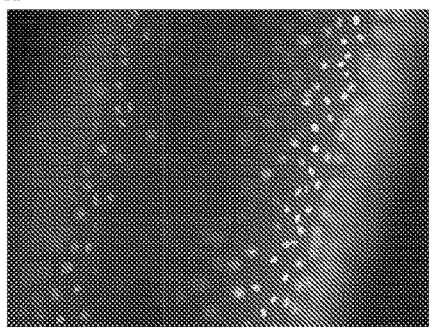
Figure 9F:
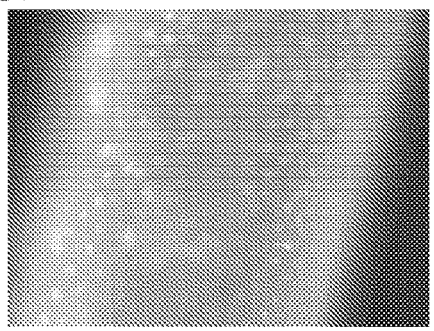
Figure 9G:
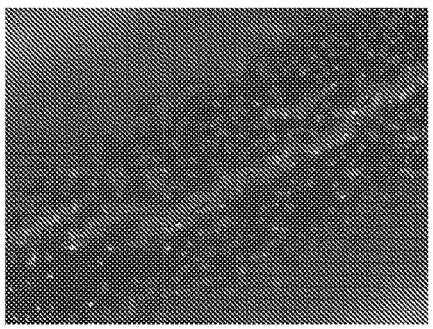
Figure 9H:
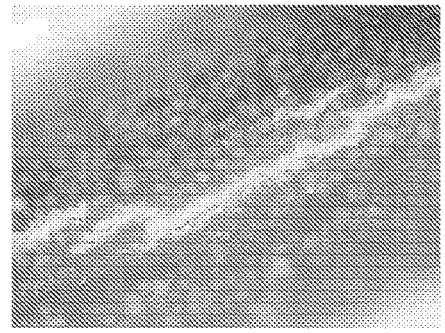

The hollow tubes of the tube platform can be used to provide a cellular environment that mimics the bronchiolar environment existing in an organism (such as a human). In some embodiments, the hollow tubes are capable of transporting fluids through a bronchiolar device. In some examples, the hollow tubes include cells (for example cells attached to the central lumen and/or exterior of the elongated body). The hollow tubes also can provide an environment for cell and/or tissue growth. In particular disclosed embodiments, the hollow tubes can be configured to tolerate various levels of wall shear stress caused by the fluid flowing there through. Exemplary embodiments can exhibit the behaviors summarized in the graphs provided by FIGS. 5-7. FIGS. 5 and 6 show model-simulated parameter effects of flow velocity and inner diameters on wall shear stress. Such information can be used to determine an optimal shear stress for bronchial cell growth, which can aid in determining particular operation parameters based on the modeling analyses. FIG. 7 shows results obtained from the evaluation of liquid flux using different liquid flow rates with and without air flow. To grow cells in air-liquid interface in the particular embodiments illustrated in FIG. 7, moistened air with a 10 µL/min flow rate was injected through apical side of hollow fiber while medium flow rate was maintained at 10 µL/min to prevent the formation of liquid plugs.

In some embodiments, the hollow tubes can be made of a polymeric material, such as polyethersulphone, mixed cellulose ester, cellulose, polysulfone, polypropylene, polyvinylidene fluoride, and other biocompatible polymeric materials. Exemplary embodiments of the hollow tubes include a mixed cellulous ester coating comprising collagen, such as collagen type I. In some embodiments, the collagen can be coated onto the tube, with exemplary embodiments being coated with collagen for four hours at 37° C. The elongated body can have any length suitable to facilitate passage of fluids into and out of the device. In some embodiments, the length of the elongated body can be varied (e.g., increased or decreased) to simulate various different generations of the type of bronchiole branching that can be present in a lung. In particular disclosed embodiments, the length of the elongated body can range from 5 mm to 30 mm (or higher), such as 10 mm to 20 mm, or 10 mm to 15 mm. In exemplary embodiments, the elongated body has a length of 10 mm.

The elongated body also can have an outer diameter that ranges from 0.38 mm to 1.4 mm (or higher), such as 0.5 to 1.2 mm, or 1 to 1.2 mm. In exemplary embodiments, the elongated body can have an outer diameter of 1 mm. Hollow tubes also can have a central lumen that can have any diameter capable of conducting a sufficient amount of fluid into and out of the device. In some embodiments, the central lumen can have a diameter ranging from 0.2 mm to 1 mm (or higher), such as 0.3 to 0.6 mm, or 0.5 to 0.6 mm. In exemplary embodiments, the central lumen can have a diameter of 0.6 mm to 1 mm. In some embodiments, the central lumen can extend throughout the entire length of the elongated body.

In some embodiments, the hollow tubes include a plurality of pores passing from the exterior diameter of the central lumen through the exterior of the elongated body. The pores can have any shape and size sufficient for allowing passage of fluids, cells, chemical compounds, and/or gases into and/or out of the tubes. In particular disclosed embodiments, the pore size can range from 0.01 to 3 µm (or higher), such as 0.1 to 1 µm, or 0.2 to 0.4 µm. In exemplary embodiments, the pore size can be 0.2 µm. The pores can have the same or different shape and/or size and any number of pores can be included in each tube. In particular disclosed embodiments, the pores can allow fluid communication between an air-liquid interface, as illustrated in FIG. 8.

FIG. 8 is a schematic diagram illustrating an air-liquid interface present in a hollow tube component of a bronchiolar device. According to FIG. 8, a first fluid, such as air, gas, or a combination thereof, (represented by arrow 10), can flow through the central lumen 12 of a hollow tube 14 and a second fluid, such as a biological medium (represented by arrows 16) can flow past the exterior of the hollow tube.

Hollow tube 14 includes a plurality of pores 18 formed through elongated body 40, which allow the first fluid 10 and second fluid 16 to pass in and out of the central lumen 12. Drugs and other stimuli (20) also can pass through central lumen 12, which can be coated with epithelial cells 22 and an extracellular matrix 24. Gases 26 and liquid 28 also can be exchanged into and out of the hollow tube 14. The exterior of the hollow tube 14 includes endothelial cells 30 as well as an extracellular matrix 32. Secreted signals 34 can be produced by the endothelial cells 30, for example, upon stimulus from components present within the hollow tube 14.

A plurality of hollow tubes can be used to make the tube platform, with some embodiments comprising 1 hollow tube to 100 hollow tubes, such as 1 hollow tube to 75 hollow tubes, or 1 hollow tube to 50 hollow tubes. In exemplary embodiments, one, two, three, four, five, six, or more hollow tubes can be included. In some embodiments, the plurality of hollow tubes can be arranged in a parallel orientation to one another and each hollow tube can be separated from other hollow tubes by a distance of 0.1 mm to 10 mm (or higher), such as 0.5 to 2 mm, or 1 to 2 mm. The hollow tubes can be arranged in a planar or non-planar arrangement.

In some embodiments, a membrane, rather than a tube platform, can be used to facilitate cell and/or tissue growth within the device as well as provide an air-liquid interface to allow for gas exchange. The membranes can comprise a first side that corresponds to the central lumen of a hollow tube embodiment and a second side that corresponds to the exterior of the elongated body of a hollow tube embodiment. In some embodiments, membranes are used in bronchiolar devices comprising two fluid chambers and can facilitate fluid communication between the two fluid chambers. In some other embodiments, membranes can be used in embodiments of a bronchiolar device comprising a transwell portion and a well portion, as disclosed herein.

Membranes used in the disclosed devices can be made of any material capable of coupling cells or tissue. In exemplary embodiments, the membrane includes a material selected from poly-L-lactic acid, polydimethylsiloxane (PDMS), polycprolactone (PCL), PLLA-PCL copolymer, polyester, polycarbonate, or a combination thereof. The membrane can also comprise pores to facilitate transport of components of the fluids used in the bronchiolar device through the membrane. In some embodiments, the membrane can be a transwell membrane comprising a polyester material with thicknesses ranging from 1 to 100 μm, such as 1 to 50 μm, or 1 to 10 μm. In exemplary embodiments, the membrane can be 10 μm. Pores of the membrane can have diameters ranging from 0.4 to 12 μm, such as 0.4 to 3 μm, or 0.4 to 11 μm, with pore densities ranging from $1\times10^5$ to $1\times10^8$ pores/cm$^2$, such as $4\times10^5$ to $4\times10^6$ pores/cm$^2$, or $2\times10^6$ to $4\times10^6$ pores/cm$^2$. In exemplary embodiments, the pores can have a diameter of 0.4 μm and the density of the pores can be $4\times10^6$ pores/cm'.

In particular disclosed embodiments, the hollow tubes and/or the membrane discussed above can be associated with one or more cell populations. In some embodiments, cell populations that are associated with the hollow tubes and/or membranes discussed above can be coupled or adhered to such components. In other embodiments, cell populations can be associated with the hollow tubes and/or membranes but need not be coupled or adhered to such components. In some embodiments, the hollow tubes include cells present on the exterior of the elongated body and on the surface of the central lumen of the hollow tube. The cell populations present on the exterior of the elongated body can be the same or different from the cell population present on the surface of the central lumen. In particular disclosed embodiments, the cell populations can be cultivated to form a cell layer or tissues that coat, or substantially coat, the surface of the central lumen and/or the exterior of the elongated body. Both sides of a membrane also can be associated with one or more cell populations. In some embodiments, a first cell population can be associated with one side of the membrane and a second cell population can be associated with the other side of the membrane.

In particular disclosed embodiments, the exterior of the elongated body of a hollow tube disclosed herein (or an "endothelial side" of a membrane) includes (or is associated with) endothelial cells, such as lung microvascular endothelial cells (e.g., HLMVE cells) that can produce an endothelium that coats, or substantially coats, the exterior of the elongated body (or the endothelial side of the membrane). The surface of the central lumen (or "epithelial side" of a membrane) includes (or is associated with) epithelial cells, such as bronchial epithelial cells (e.g., BEAS-2B) that can produce an epithelium that coats, or substantially coats the surface of the central lumen (or epithelial side of the membrane).

Figure 10A:
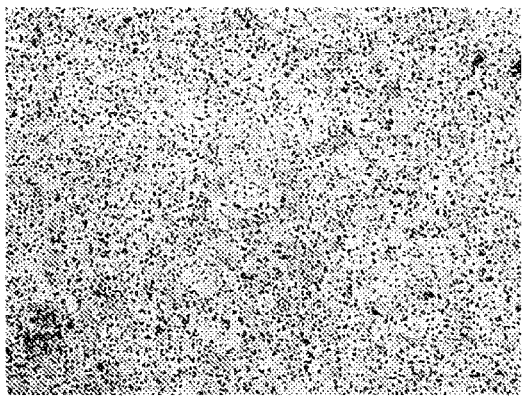
FIGS. 10A-10D are morphological images of exemplary tissue embodiments that were grown on bronchiolar device embodiments disclosed herein.
Figure 10B:
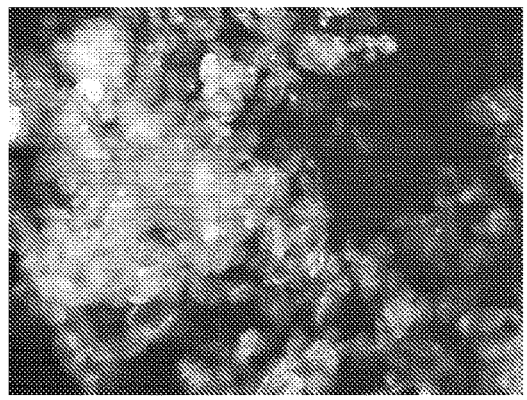
Figure 10C:
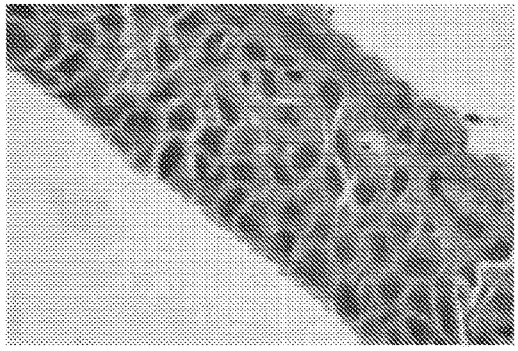
Figure 10D:

Exemplary embodiments including different cell populations grown on a hollow tube or membrane are illustrated in FIGS. 9A-9H. FIGS. 9A, 9B, 9E, and 9F show endothelial cells present on the exterior of the elongated body of exemplary hollow tube embodiments and FIGS. 9C, 9D, 9G, and 9H show epithelial cells present on the interior of a central lumen of an exemplary tube. Bronchial epithelial tissue includes mucin-producing cells, cilia cells, and combinations thereof. FIGS. 10A-10D illustrate embodiments of normal human bronchial epithelial cells seeded on a transwell membrane and detected using suitable stains. Alcian blue staining was used for detecting mucin (FIG. 10A), β-tubulin staining was used to detect cilia (FIG. 10B), H&E staining was used to detect differentiated cells (FIG. 10C) and tight junction staining was used to detect the epithelium barrier (FIG. 10D).

In exemplary embodiments, the first substrate can be configured to include a first inlet and a first outlet that can be used to deliver a first fluid, such as air, gas, or a combination thereof, to and from the bronchiolar device, and a second inlet and a second outlet that can be used to deliver a second fluid, such as a biological medium (for example, a lung-specific medium or a "universal" cell or organ medium) to and from the bronchiolar device. The first substrate can further include a first fluid port and a second fluid port that can be used to deliver the first fluid and the second fluid (respectively) to an alveolar device as disclosed herein. The first fluid port and the second fluid port should be positioned within the first substrate so that they are in fluid communication with a flow path of the first fluid and second fluid, respectively. In some embodiments, the first fluid port is positioned opposite the first inlet and in a position to facilitate deliver of the first fluid after it has exited a hollow tube. In some embodiments, the second fluid port is positioned within the incubation chamber of the first substrate.

In some embodiments, the first substrate can further include one or more fluid chambers that are fluidly coupled to the first inlet, the first outlet, the first fluid port, or a combination thereof. The fluid chambers are reservoirs, or reservoirs further including one or more channels, that can store a fluid and that are formed within a substrate so that at least one reservoir is located on both ends of a tube platform or both sides of a membrane of a bronchiolar device. In some embodiments, the fluid chambers can be fluidly coupled to the first inlet and/or the first fluid port.

In some embodiments, the bronchiolar devices disclosed herein also include an incubation chamber that is formed within the first substrate. The incubation chamber can be fluidly coupled to one or more inlets, outlets, or fluid ports of the device. In particular disclosed embodiments, the incubation chamber is configured to accept a tube platform comprising a plurality of hollow tubes that can be fluidly coupled to the one or more fluid chambers, one or more channels, or a combination thereof. In other disclosed embodiments, the incubation chamber can be configured to accept a membrane. The membrane can have a "fluid side," which in some embodiments can correspond to the epithelial side of the membrane and a "biological medium side," which in some embodiments can correspond to the endothelial side of the membrane. A "fluid side" of the membrane, as used herein, is understood to refer to the side of a membrane that faces a first fluid passing through the bronchiolar device, such as air, gas, or a combination thereof. A "biological medium side" of the membrane, as used herein, is understood to refer to the side of the membrane that faces a second fluid passing through the bronchiolar device, such as a biological medium. The incubation chamber is used to accept the second fluid introduced into the device and therefore provide a fluid environment that surrounds the hollow tubes of the tube platform so that cells associated with the exterior of the hollow tube can be exposed to a fluid environment different from the central lumen of the hollow tube.

In exemplary embodiments, a second substrate can be included, which includes a plurality of fluid ports that are configured to align with the inlet, outlets, ports, or a combination thereof, of the first substrate and can be further aligned with one or more inlets, outlets, or fluid ports of an alveolar device. In some embodiments, the fluid ports of the bottom substrate (or second substrate) can be configured to align with a plurality of connectors that can be used to fluidly couple the bronchiolar device to a plurality of alveolar devices. In some embodiments, the second substrate can be placed under the first substrate thereby forming a top (e.g., first) and bottom (e.g., second) substrate. In some embodiments, the top and bottom substrate may be further coupled to additional substrates that can be placed above the top substrate and/or below the bottom substrate.

Figure 11:
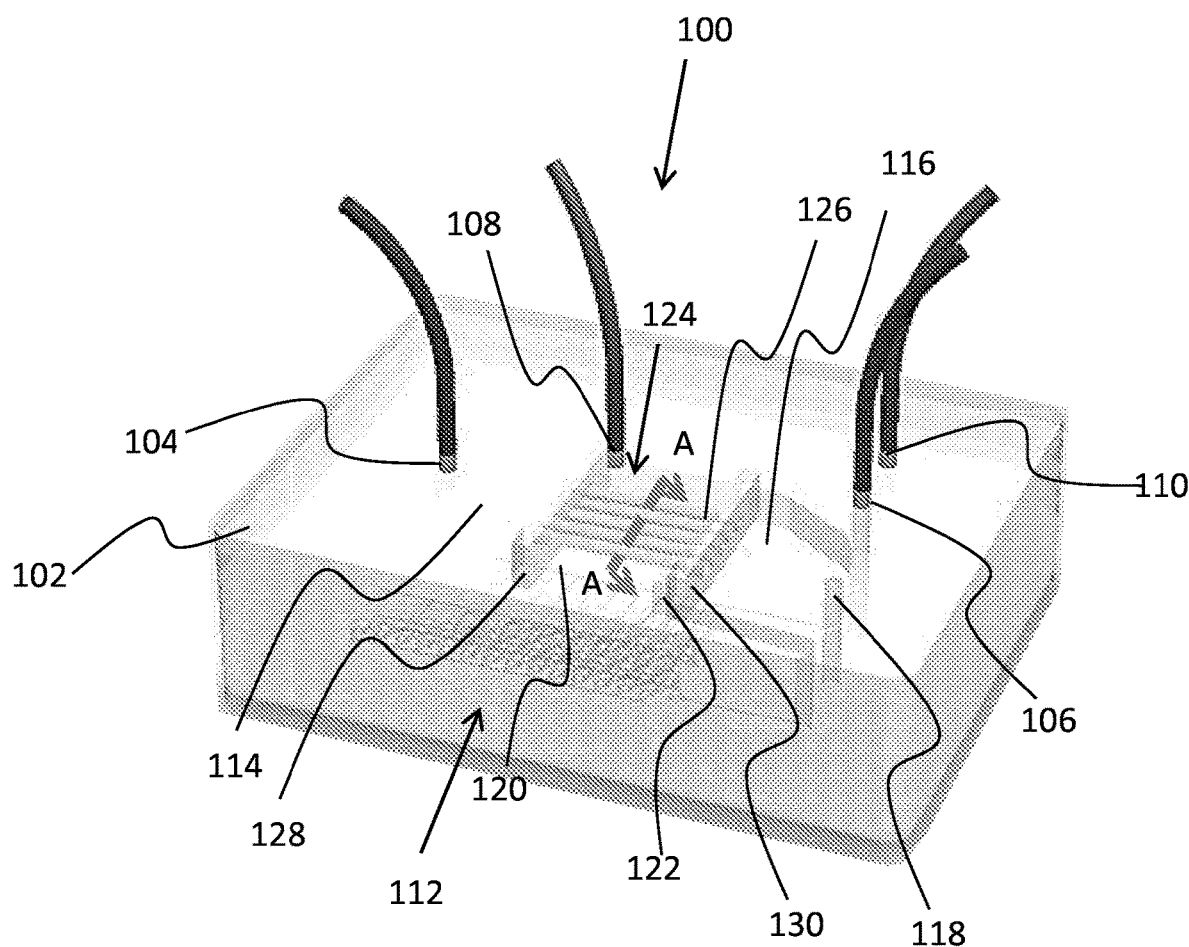
FIG. 11 illustrates an exemplary bronchiolar device embodiment comprising a tube platform.
Figure 12:
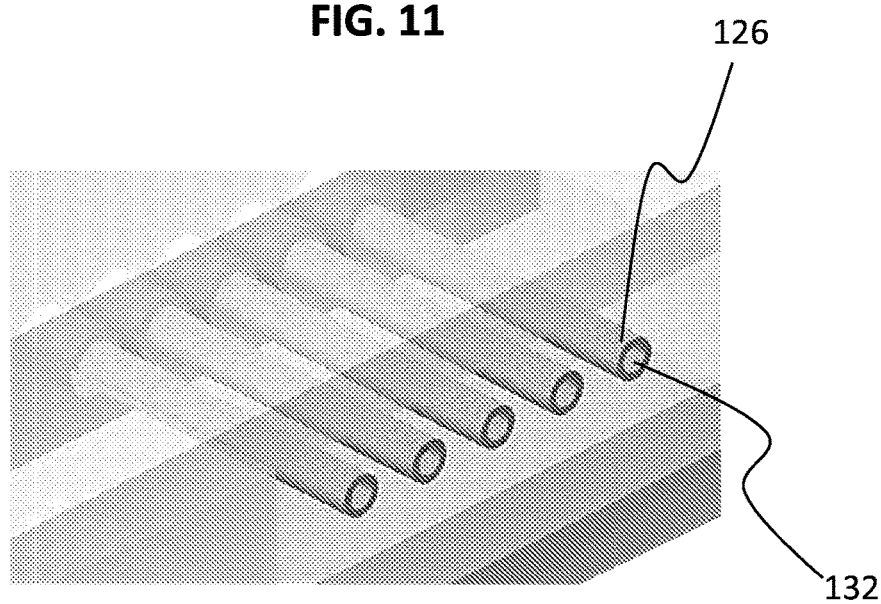
FIG. 12 is an expanded cross-sectional view of the device illustrated in FIG. 11 further illustrating a cross section of exemplary hollow tubes used in a tube platform.
Figure 13:
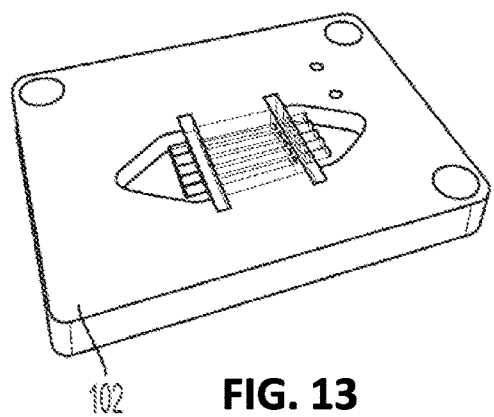
FIG. 13 shows an exemplary embodiment of a substrate of a bronchiolar device comprising an incubation chamber and inlets and outlets that can be used to deliver fluids to and from the bronchiolar device.

FIGS. 11 and 12 illustrate an exemplary embodiment of a bronchiolar device 100. As illustrated in FIG. 11, first substrate 102 can be configured to include two inlets 104 and 106 through which a first and second fluid can be delivered into device 100. First substrate 102 can further include two outlets 108 and 110 through which the first and second fluids can be delivered from (e.g., exit) the device after having passed through a fluidly coupled alveolar device portion 112. Two fluid chambers 114 and 116 can be included in the first substrate 102 and can be fluidly coupled to inlet 104 and fluid port 118. Additionally, incubation chamber 120 can be included, which can be fluidly coupled to inlet 106 and fluid port 122. While FIG. 11 illustrates a particular configuration of these inlets and outlets, any suitable configuration can be used.

Bronchiolar device 100 can further include tube platform 124, which includes a plurality of hollow tubes 126 that can deliver a first fluid from fluid chamber 114 to fluid chamber 116. Tube platform 124 can further include two solid substrates 128 and 130 that separate a first fluid present in fluid chambers 114 and 116 from a second fluid present in incubation chamber 120. FIG. 12 is a cross-sectional view taken along axis A-A of FIG. 11 and further illustrates central lumens 132 of hollow tubes 126 through which a first fluid can flow.

Figure 14:
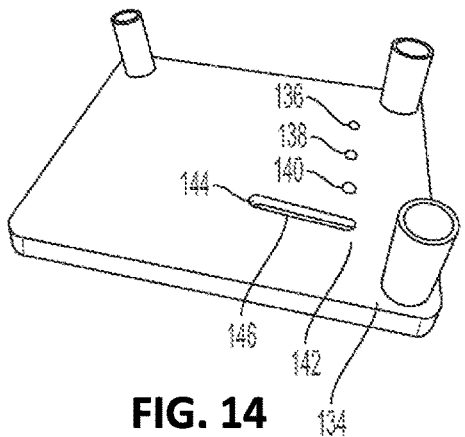
FIG. 14 shows an exemplary embodiment of a substrate of a bronchiolar device on an alignment stage wherein the substrate comprises fluid ports and at least one channel that can be fluidly coupled to the substrate shown in FIG. 13.
Figure 15:
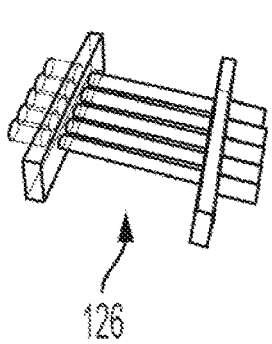
FIG. 15 shows an exemplary tube platform comprising a plurality of parallel hollow tubes.
Figure 16:
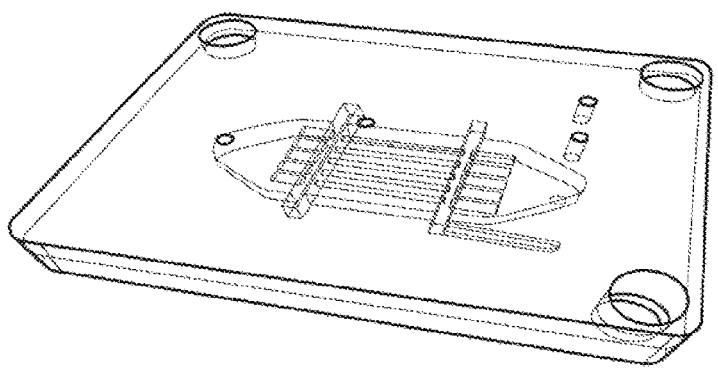
FIG. 16 shows an exemplary bronchiolar device made using the components shown in FIGS. 13-15.
Figure 17:
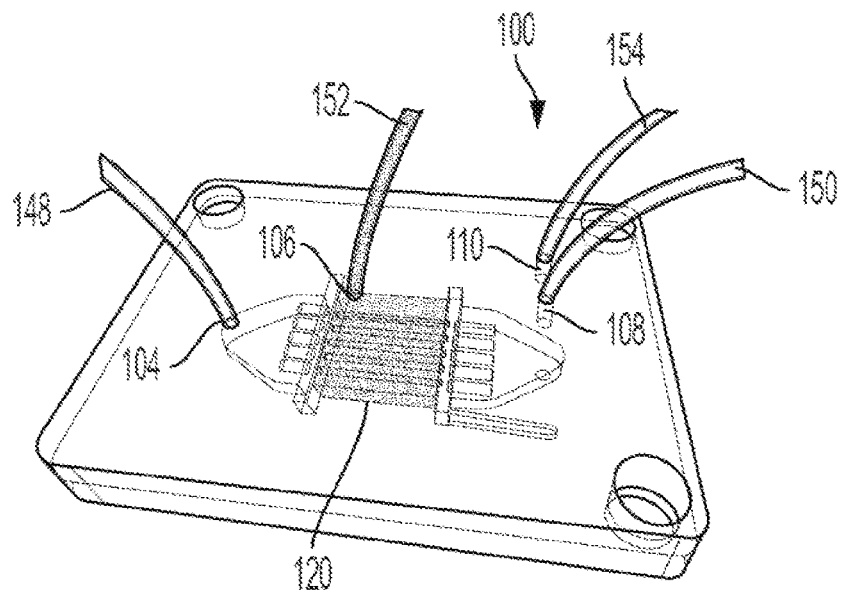
FIG. 17 shows the bronchiolar device of FIG. 16 and further shows how a plurality of tube lines can be connected to the inlets and outlets of the device to deliver fluids to and from the device.

FIGS. 13-16 show exemplary embodiments of a first substrate 102 (FIG. 13), a second substrate 134 (FIG. 14), tube platform 126 (FIG. 15), and an assembled bronchiolar device 100, wherein the first substrate, second substrate, and tube platform are combined (FIG. 16). FIG. 14 illustrates an exemplary embodiment of a second substrate 104 that includes fluid ports 136, 138, 140, 142, and 144 that facilitate delivery of one or more fluids from the first substrate 102 to alveolar device 112. As illustrated in FIG. 14, a channel 146 can be provided to fluidly couple fluid ports 142 and 144. FIG. 17 shows another view of bronchiolar device 100. In FIG. 17, bronchiolar device 100 is connected to a plurality of tube lines 148, 150, 152 and 154. Tube 148 can be used to introduce a first fluid, such as air, gas, or a combination thereof, to inlet 104 and tube 150 can be used to extract the first fluid from outlet 108 after it has passed through an alveolar device (not illustrated). Tube 152 can be used to introduce a second fluid, such as a biological medium into incubation chamber 120 through inlet 106 and tube 154 can be used to remove the second fluid from outlet 110.

Figure 18:
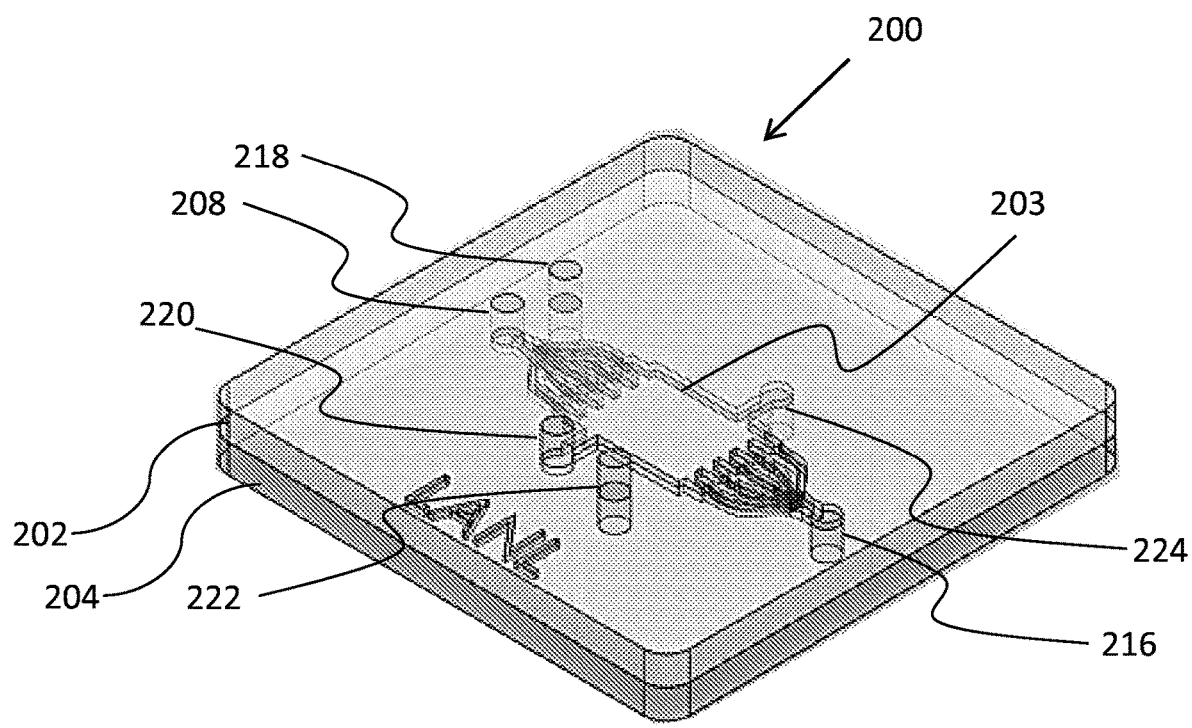
FIG. 18 illustrates an exemplary embodiment of a bronchiolar device comprising an alternative configuration of inlets and outlets.
Figure 19:
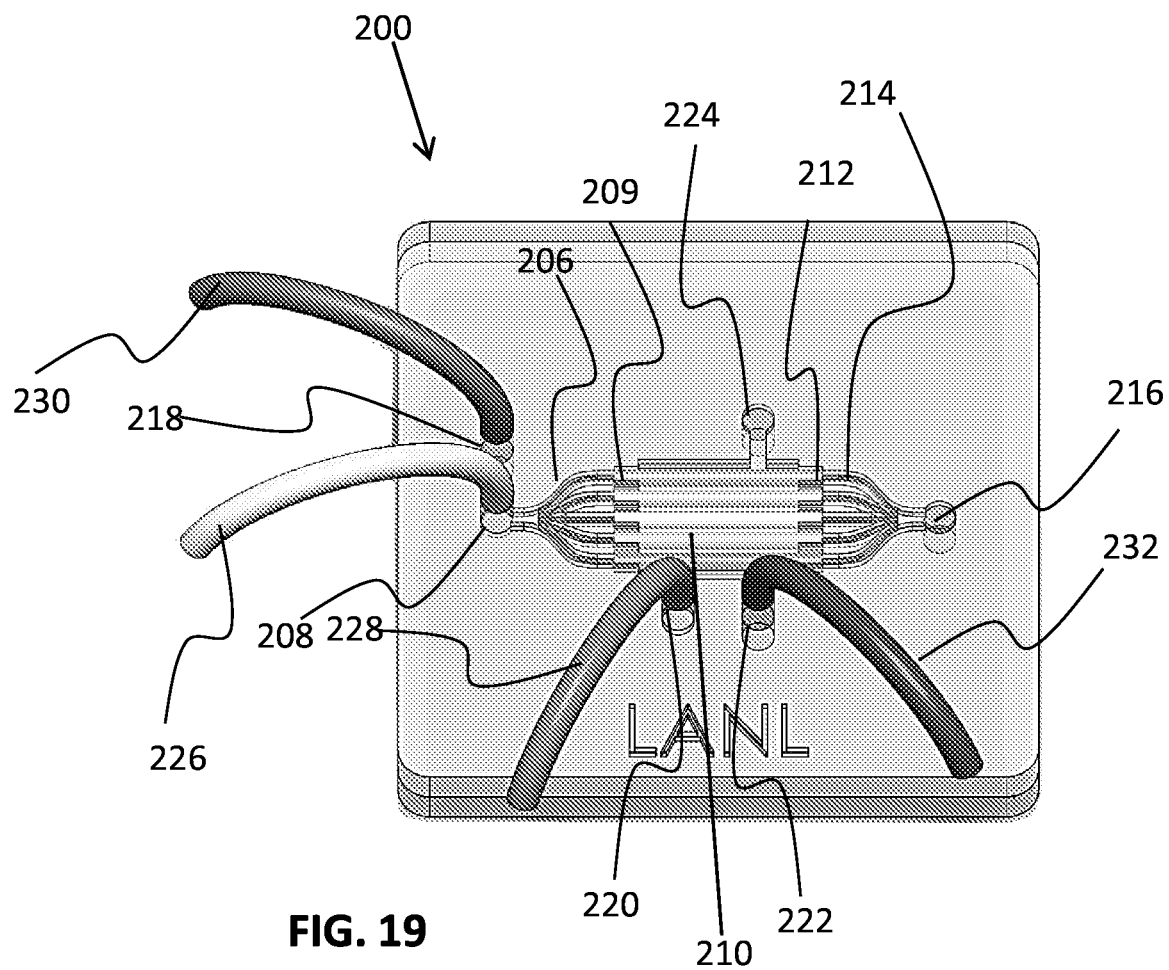
FIG. 19 illustrates the bronchiolar device illustrated in FIG. 18 and further illustrates tube lines connected to various inlets and outlets of the device as well as a plurality of hollow tubes within an incubation chamber.

Another exemplary embodiment of a bronchiolar device 200 is illustrated in FIGS. 18 and 19. As illustrated in FIG. 18, bronchiolar device 200 includes a first substrate 202 connected to a second substrate 204. As further illustrated in FIG. 19, the first substrate 202 includes an incubation chamber 203 and a plurality of channels 206 that extend from inlet 208 to a first end 209 of hollow tube 210. As illustrated in FIG. 19, each channel 206 can be aligned and fluidly coupled with a central lumen (not illustrated) of hollow tubes 210 to deliver a fluid from the inlet 208 into the central lumen of each tube. Hollow tube 210 further includes a second end 212 which is also fluidly coupled to a plurality of channels 214 that extend from second end 212 to a fluid port 216 that can be connected to an alveolar device disclosed herein. Device 200 can further include an outlet 218, which can be positioned adjacent to the inlet 208, through which fluid can be delivered from the device once delivered from the alveolar device. Device 200 also includes an additional inlet 220, outlet 222, and fluid port 224 through which a second fluid can be introduced into and expelled from the device.

In the embodiment illustrated in FIGS. 18 and 19, inlets 208 and 220 can be positioned adjacent to outlets 218 and 222, respectively; however, any suitable configuration can be used. As further illustrated in FIGS. 18 and 19, device 200 also can further include fluid ports 216 and 224 that can be fluidly coupled to an alveolar device to facilitate delivery of the first and second fluids (respectively) to the alveolar device. A plurality of exterior tube lines 226, 228, 230, and 232 can be fluidly coupled to the inlets 208 and 220 and outlets 218 and 222, respectively. Tube lines 226 and 230 can be used to deliver and remove fluid (e.g., air or gas) to inlet 208 and outlet 220 (respectively), and tube lines 228 and 232 can be used to deliver and remove a second fluid (e.g., biological media or blood surrogate) to inlet 220 and outlet 222.

Figure 20:
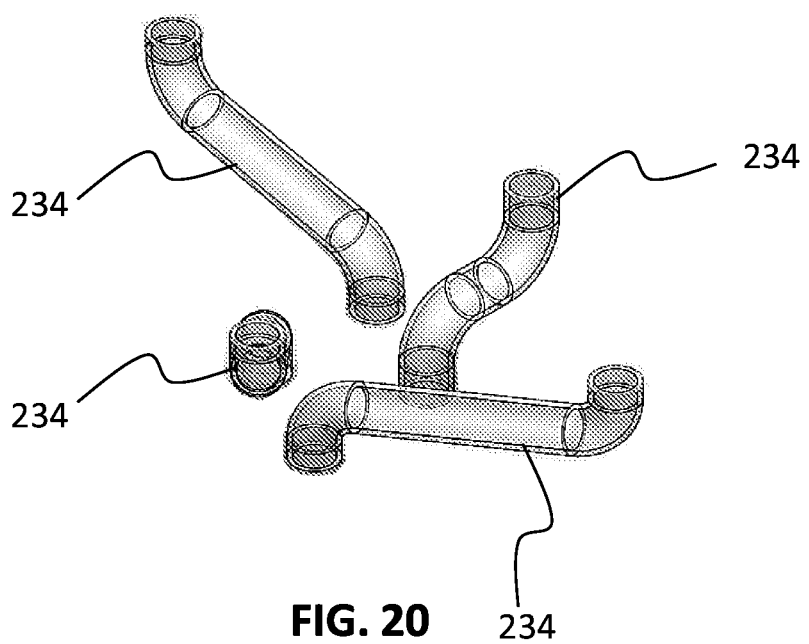
FIG. 20 illustrates a plurality of connecting tubes that can be used to fluidly couple a bronchiolar device embodiment to an alveolar device embodiment.

As illustrated in FIG. 20, a plurality of connecting tubes 234 can be configured to deliver a first and second fluid to and from the bronchiolar device 200 and an alveolar device. Any suitable configuration, size, and shape of connecting tubes can be used.

Figure 21:
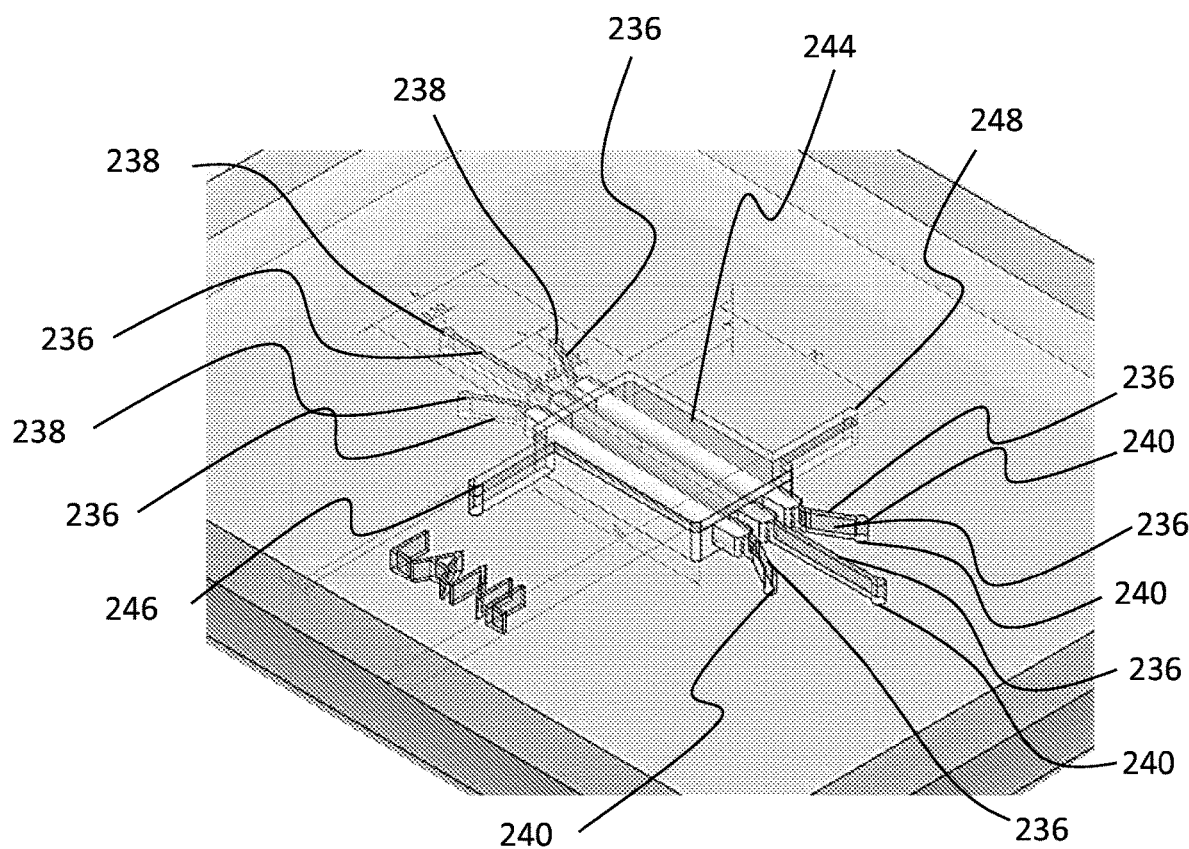
FIG. 21 illustrates another embodiment of a bronchiolar device.
Figure 22:
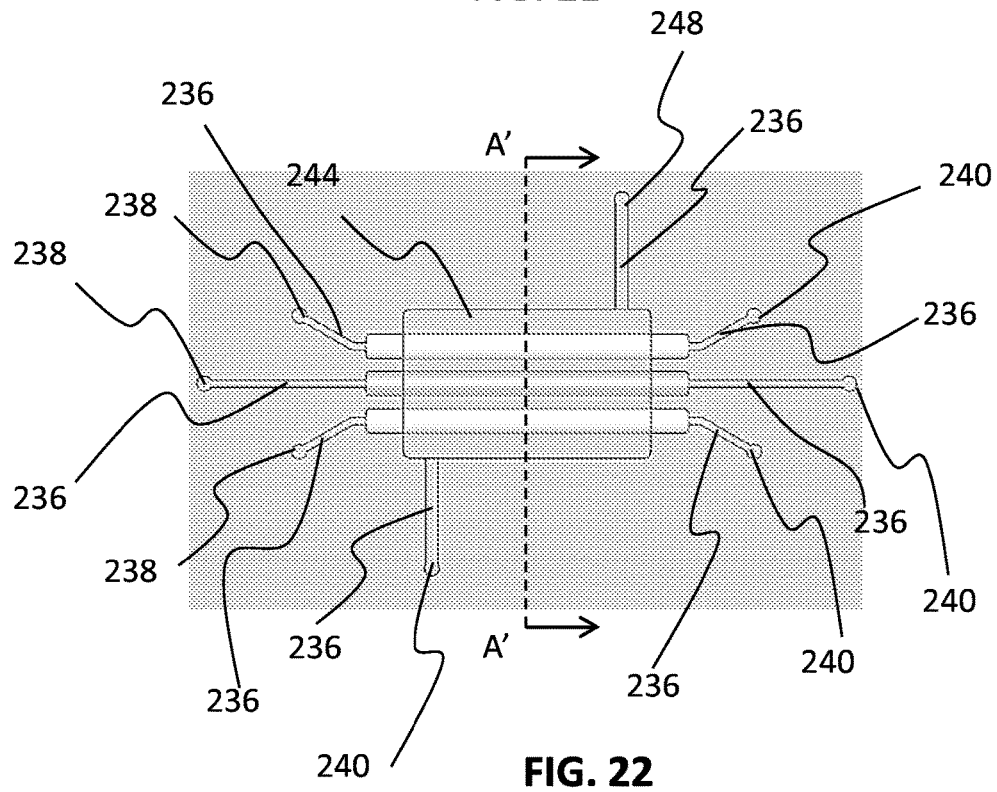
FIG. 22 is a top view of the bronchiolar device illustrated in FIG. 21.
Figure 23:
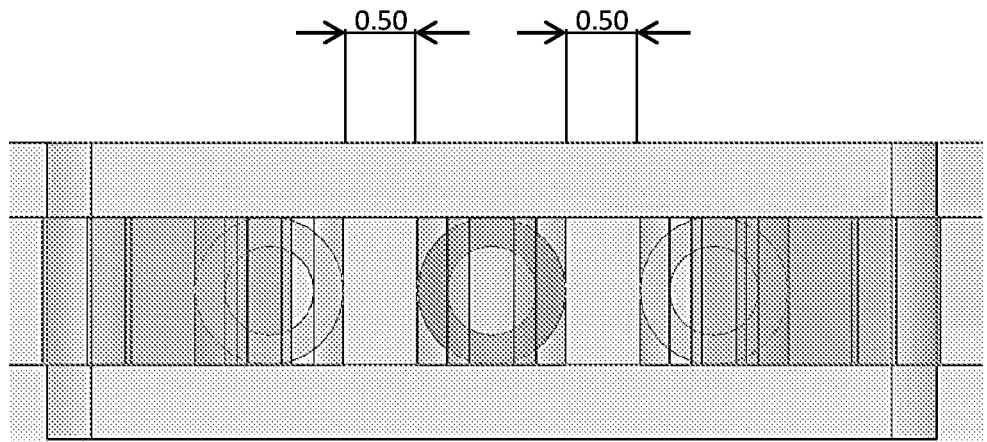
FIG. 23 is a cross-sectional view of the bronchiolar device illustrated in FIG. 22, taken along line A'-A'.
Figure 24:
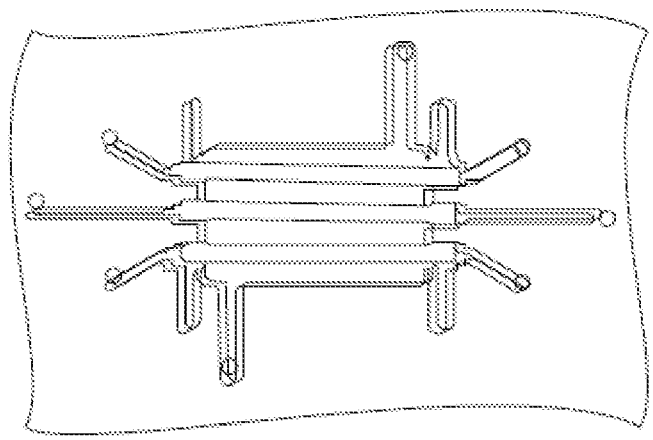
FIG. 24 shows a working example of the bronchiolar device illustrated in FIG. 21.

Another exemplary bronchiolar device is illustrated in FIGS. 21-24. As illustrated in FIG. 21, individual channels 236 can lead to individual fluid ports 238 and 240 in bronchiolar device 242. Incubation chamber 244 can be fluidly coupled to fluid ports 246 and 248. FIG. 22 illustrates a top view of device 242 and FIG. 23 illustrates a cross-sectional view taken along line A'-A' (FIG. 22). FIG. 24 shows an exemplary embodiment of device 242.

Bronchiolar device embodiments described above can be configured to be stacked vertically with an alveolar device as disclosed herein; however, alternative coupling configurations also can be used. In some embodiments, the bronchiolar device and the alveolar device can be coupled serially through tubing that couples the bronchiolar device to one or more alveolar devices. In such embodiments, the bronchiolar device can have any one of the configurations illustrated in FIG. 25-33. Each of these embodiments is described below.

Figure 25:
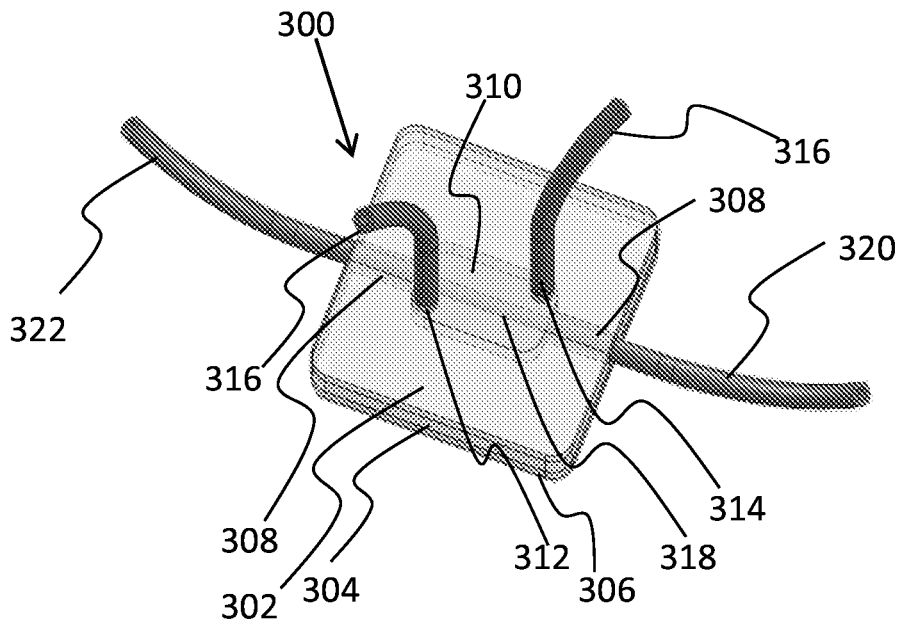
FIG. 25 illustrates an additional embodiment of a bronchiolar device.
Figure 26:
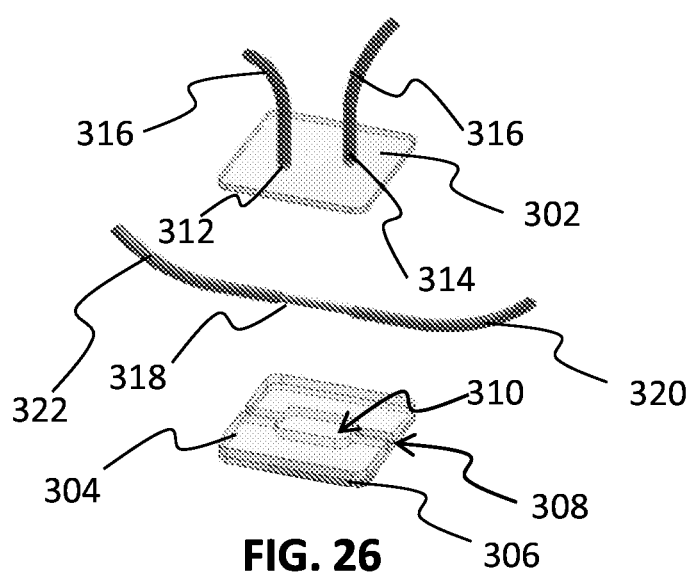
FIG. 26 illustrates an exploded perspective view of the bronchiolar device illustrated in FIG. 25.

An exemplary bronchiolar device 300 that can be serially coupled to an alveolar device is illustrated in FIGS. 25 and 26. Device 300 (FIG. 25) includes a first substrate 302, a second substrate 304, and a third substrate 306 that can be placed between the first and second substrates, as illustrated in FIGS. 25 and 26. As further shown in FIG. 26, the third substrate 306 can be fabricated to include at least one channel 308 that can be fluidly coupled with incubation chamber 310. First substrate 302 includes inlet 312 and outlet 314, which can be fluidly coupled to incubation chamber 310. Inlet 312 and outlet 314 can be coupled to tube lines 316, which can be oriented perpendicular to the incubation chamber 310. Third substrate 306 can be configured to accept a hollow tube 318, which can be fluidly coupled to tube lines 320 and 322, which can be used to deliver a fluid through hollow tube 318. An exemplary embodiment of device 300 is shown in FIG. 27.

Figure 27:
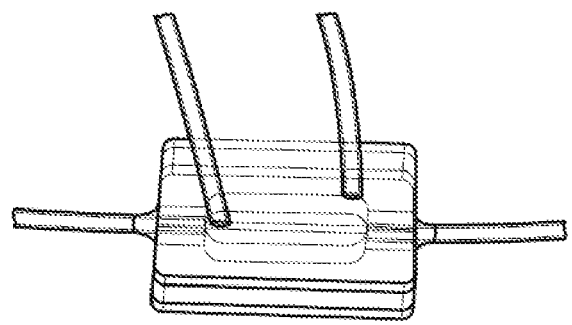
FIG. 27 shows a working example of the bronchiolar device illustrated in FIG. 25.
Figure 28:
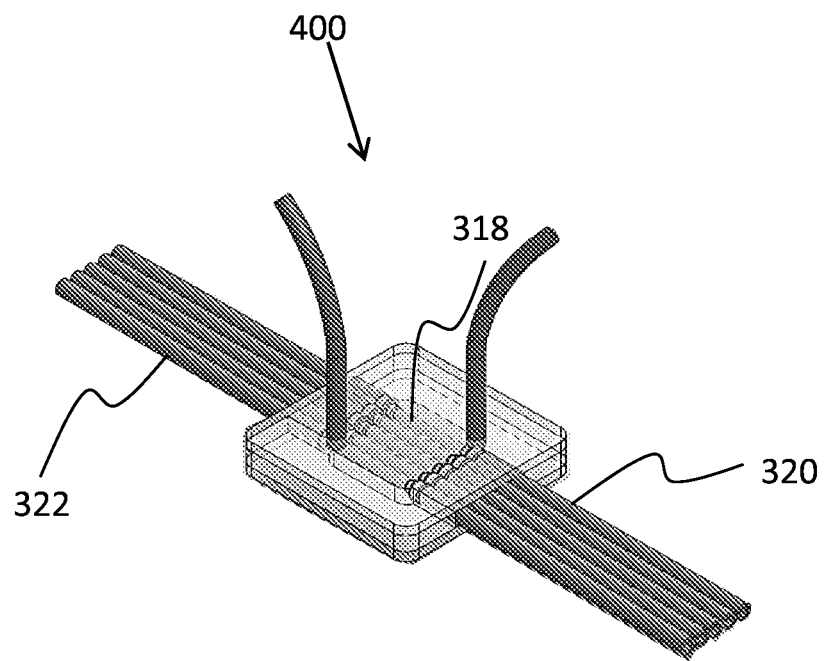
FIG. 28 illustrates an additional embodiment of a bronchiolar device similar to the device illustrated in FIG. 25 and further comprising a plurality of hollow tubes within an incubation chamber.
Figure 29:
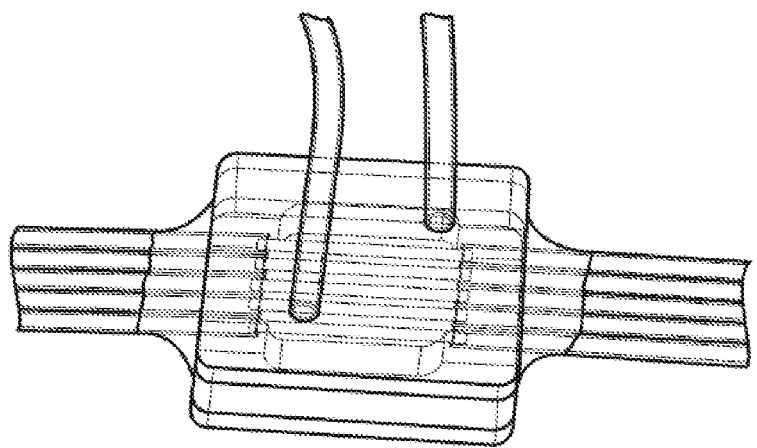
FIG. 29 shows a working example of the bronchiolar device illustrated in FIG. 28.

In another embodiment, the bronchiolar device illustrated in FIGS. 25-27 can be configured to include a plurality of hollow tubes. An exemplary embodiment is shown in FIG. 28. Device 400 includes components similar to that of device 300. The embodiment illustrated in FIG. 28, however, is modified to include a plurality of hollow tubes 318. The plurality of hollow tubes 318 can be fluidly coupled to a plurality of tube lines 320 and 322. An exemplary embodiment of device 400 is shown in FIG. 29.

Additional bronchiolar device configurations are contemplated by the present disclosure. In some embodiments, a first and second fluid may be delivered to and from the bronchiolar and alveolar devices disclosed herein through inlets and outlets of sequentially arranged bronchiolar and alveolar devices. In some embodiments, the first and second fluids introduced into the bronchiolar device can flow through fluidly coupled inlets, outlets, and channels that cause the fluids to flow in a direction parallel to hollow tubes or membranes used in particular embodiments of the bronchiolar device. By allowing the fluids to flow in this parallel direction, liquid shear stress on the cell populations coupled to the hollow tubes or membranes of the device can be prevented, or substantially prevented, and therefore the impact of liquid shear force on cell differentiation can be minimized.

FIG. 30 illustrates a device 500, which includes parallel inlets 502 and 504 through which a first fluid and second fluid can be independently introduced into the device through tube lines 506 and 508, respectively. Device 500 can further include outlets 510 and 512, which are parallel to one another and coupled to tube lines 514 and 516, respectively. FIGS. 31-33 show exemplary embodiments of device 500, wherein one hollow tube can be used (FIGS. 31 and 32) or device 500A wherein a plurality of hollow tubes can be used (FIG. 33).

Another exemplary embodiment of a bronchiolar device is illustrated in FIGS. 34-36. As illustrated in FIGS. 34 and 35, device 600 includes a plurality of substrates, such as a first substrate 602, a second substrate 604, a third substrate 606, a fourth substrate 608, and a fifth substrate 610. The first substrate 602 includes inlet 612 and an outlet 614 (FIG. 34) that allow fluid to flow from the first substrate to a fluid chamber 616 present in second substrate 604. The third substrate 606 can be placed below the second substrate 604 and can further include a channel 618 (FIG. 36) having a diameter similar to the fluid chamber 616. The fourth substrate 608 includes an incubation chamber 620 into which a second fluid can be delivered through channels 622 and 624 (FIG. 34). Device 600 can further include a membrane 626 that can be placed between second substrate 604 and third substrate 606. Membrane 626 can be used to grow cells within the device. In some embodiments, a particular cell population can be grown on the side of membrane 626 that contacts fluid present in the fluid chamber 616 and a different cell population can be grown on the other side of membrane 626 that contacts fluid present in incubation chamber 620. An exemplary embodiment of device 600 is shown in FIG. 37.

Yet another exemplary configuration of a bronchiolar device is illustrated in FIG. 38, which is an exploded perspective view of device 700. Device 700 includes well 702 comprising a membrane 704 within the bottom of the well. The well 702 can be configured to fit within a transwell portion 706, which includes a plurality of substrates, some of which are configured to include an incubation chamber 708 and designed to accept the well 702. At least one substrate of the transwell portion 706 can be configured to have an inlet 710 through which a fluid, such as a blood surrogate or other biological fluid, can flow into device 700. Device 700 also includes an outlet 712 through which the fluid can exit the device. An additional substrate similar to first substrate 602, as illustrated in FIG. 38, can be coupled to the transwell portion 706 after well 702 has been placed in the transwell portion. FIGS. 39 and 40 show an exemplary embodiment of device 700.

Figure 41:
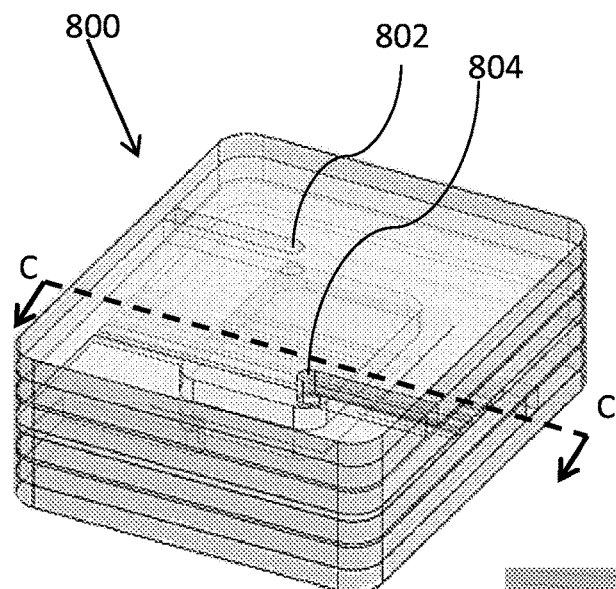
FIG. 41 illustrates an exemplary bronchiolar device comprising a fluid chamber and a medium chamber, and further comprising a membrane component placed between the two chambers.
Figure 42:
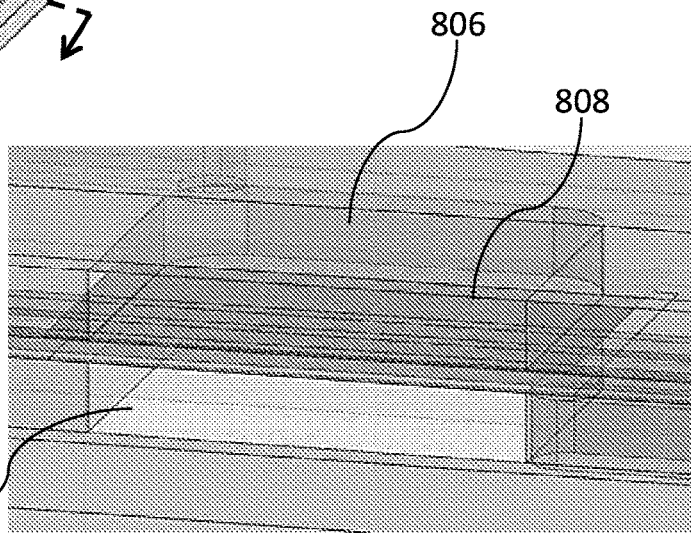
FIG. 42 is a cross-sectional view taken along axis C-C of the bronchiolar device illustrated in FIG. 41.
Figure 43:
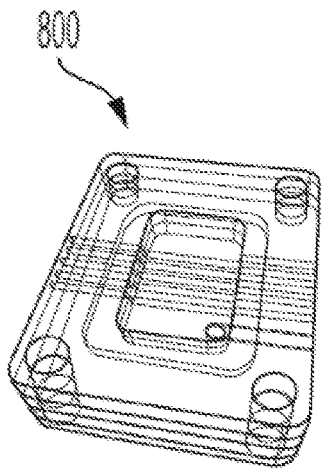
FIG. 43 shows a working example of the bronchiolar device illustrated in FIG. 41.
Figure 44:
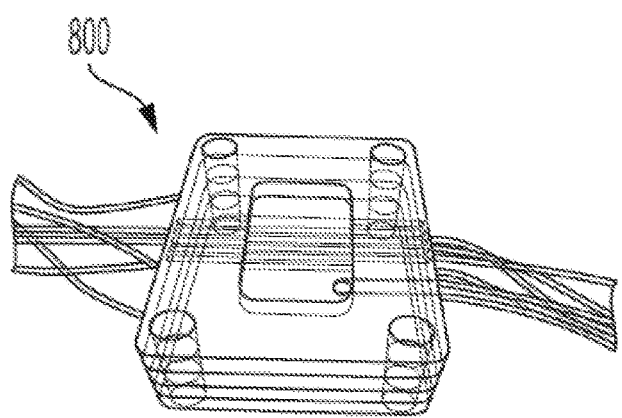
FIG. 44 shows the working example of FIG. 43 further comprising a plurality of tube lines connected to the channels formed in the bronchiolar device.

In some embodiments, the bronchiolar device can be a dual-sided bronchiolar device. An exemplary dual-sided bronchiolar device is illustrated in FIGS. 41-44. As illustrated in FIG. 41, device 800 includes a plurality of substrates stacked on top of one other. At least one of the substrates can be configured to accept a plurality of inlets and outlets connected to tube lines through which a first fluid (e.g., air or gas) can be delivered into the device. The plurality of inlets and outlets are fluidly coupled to a plurality of channels formed within a substrate. An additional inlet 802 and outlet 804 can be provided to deliver a second fluid into a first chamber 806 and second chamber 808 that are positioned above and below (respectively) the substrate comprising a plurality of microchannels or nanochannels. In some embodiments, the device can further include one or more thin layers of a membrane 808 that includes cells on each side, such as the "fluid side" or the "biological medium side" of each membrane. An exemplary device is illustrated in FIGS. 43 and 44.

Figure 45:
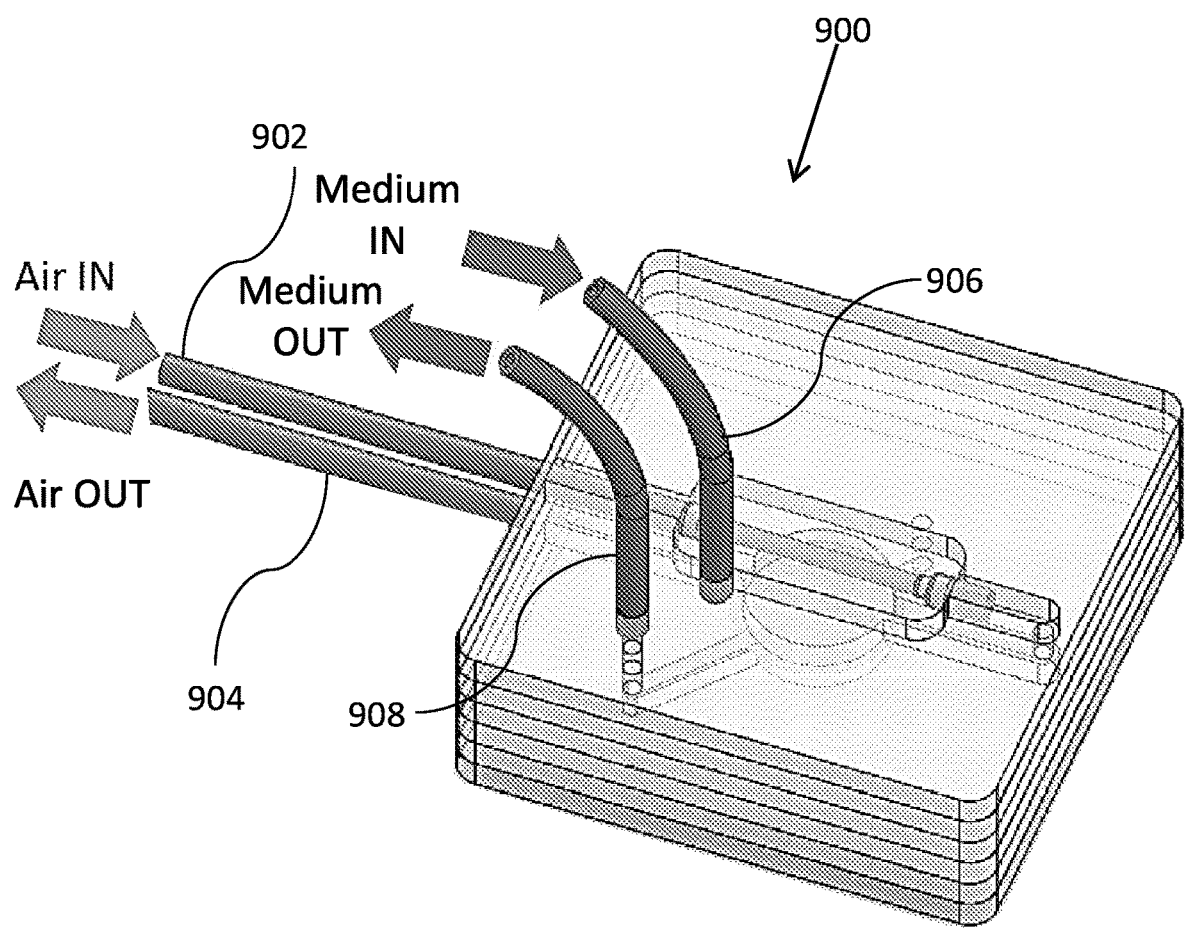
FIG. 45 illustrates another embodiment of a bronchiolar device comprising inlets and outlets positioned on the same end of the device.
Figure 46:
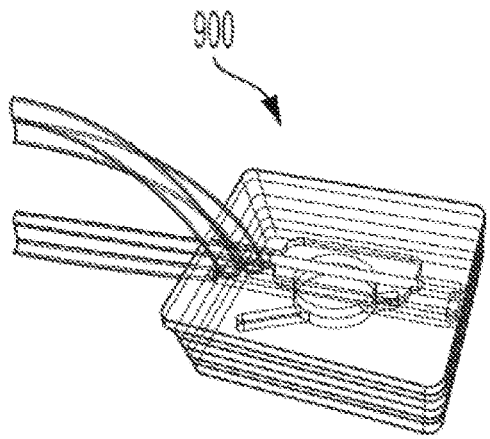
FIG. 46 shows a working example of the device illustrated in FIG. 45.
Figure 47:
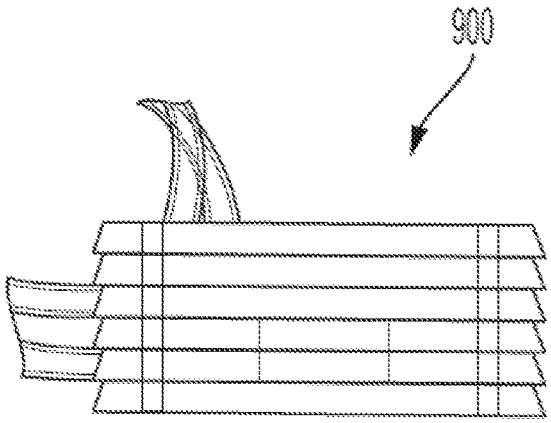
FIG. 47 shows a side view of the working example shown in FIG. 46.

Yet another embodiment of a bronchiolar device is illustrated in FIG. 45, which illustrates a bronchiolar device 900 comprising inlets and outlets positioned at the same end of the device. Device 900 includes inlet tube 902 and outlet tube 904, which can be used to deliver a first fluid to and from the bronchiolar device. As illustrated in FIG. 45, inlet tube 902 and outlet tube 904 can be positioned at the same end of device 900. Inlet tube 906 and outlet tube 908, which can be used to deliver and remove a second fluid from the device, also can be positioned at the same end of device 900 as inlet tube 902 and outlet tube 904. An exemplary embodiment of device 900 is shown in FIGS. 46 and 47.

Figure 48:
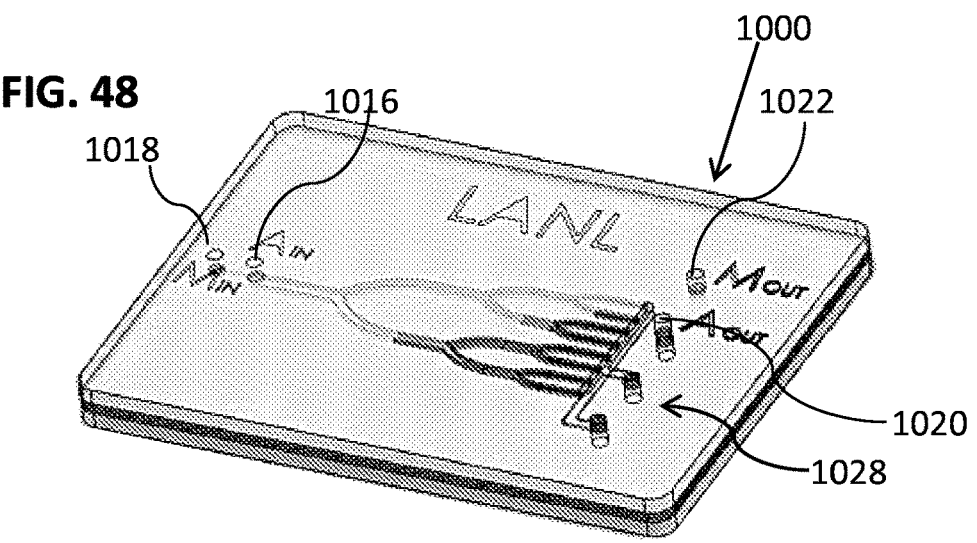
FIG. 48 illustrates an embodiment of a branching bronchiolar device.
Figure 49:
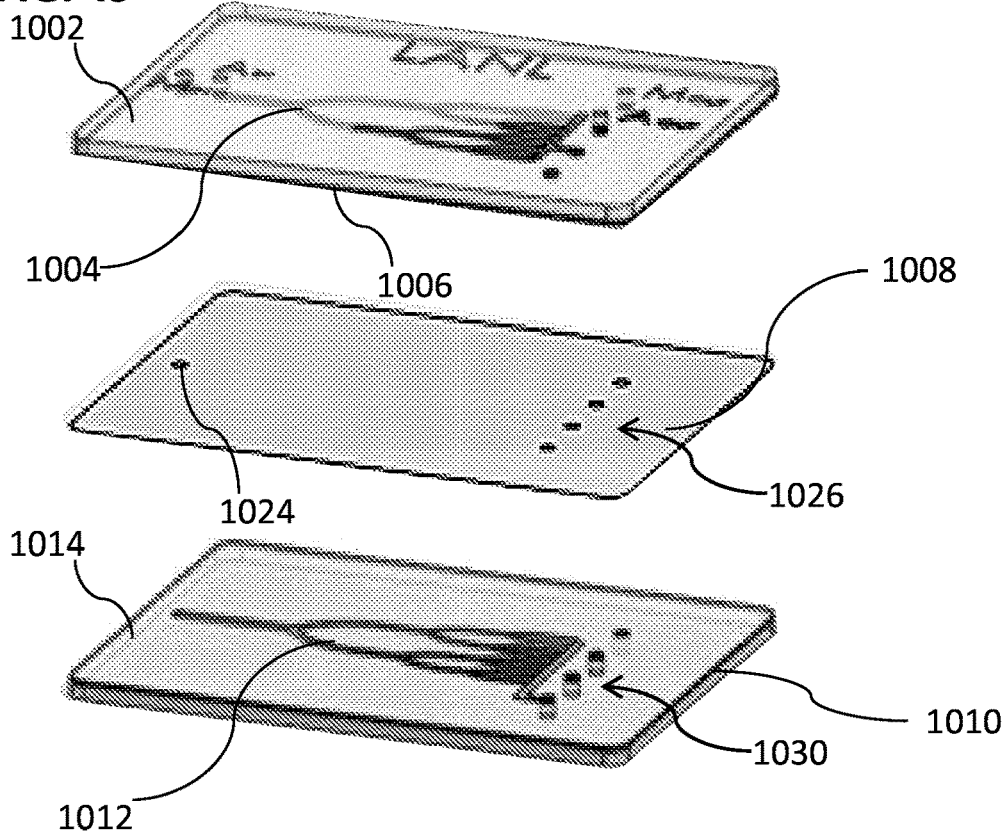
FIG. 49 illustrates certain components of the branching bronchiolar device illustrated in FIG. 48.
Figure 50:
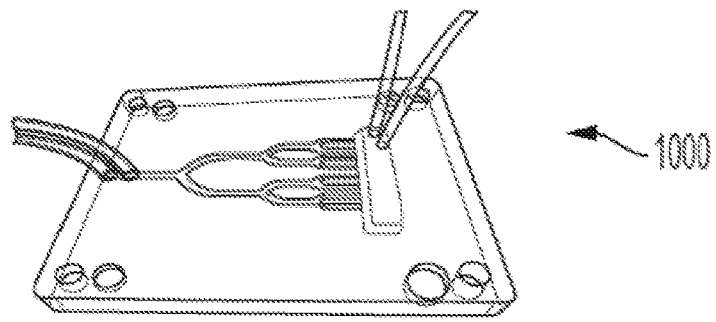
FIG. 50 shows a working embodiment of the branching bronchiolar device illustrated in FIG. 48.

In some embodiments, the bronchiolar device can be a branching bronchiolar device. An exemplary branching bronchiolar device embodiment 1000 is illustrated in FIG. 48. As illustrated in FIG. 48, the branching bronchiolar device 1000 includes a first substrate 1002 comprising a plurality of channels 1004 formed within the substrate that includes a branching pattern mimicking the bronchiolar geometry in a lung (such as a human lung). In particular disclosed embodiments, channels 1004 can be fabricated to be open on one side, such as the underside 1006, of first substrate 1002 so that the channels 1004 can be in fluid communication with membrane 1008. Device 1000 can further include a second substrate 1010 that also includes a plurality of channels 1012 having a similar branching pattern as the first substrate 1002. Similar to first substrate 1002, channels 1012 can be open on one side, such as the top side 1014, of second substrate 1010 so that they can be in fluid communication with membrane 1008. As illustrated in FIG. 49, membrane 1008 can be placed between the first substrate 1002 and the second substrate 1010. As illustrated in FIG. 49, first substrate 1002 can further include inlets 1016 and 1018, through which a first and second fluid can be introduced. Inlet 1016 can be fluidly coupled to channels 1004 of the first substrate 1002 and inlet 1018 can be fluidly coupled to channels 1012 of the second substrate 1010. Further illustrated in FIG. 49 are outlets 1020 and 1022, which can be provided within first substrate 1002 to allow the first and second fluids to exit the device. Outlet 1020 can be fluidly coupled to an alveolar device (not illustrated) so that a first fluid, which is delivered between the bronchiolar device 1000 and the alveolar device, can be removed. Outlet 1022 also can be fluidly coupled to an alveolar device (not illustrated) so that a second fluid, which is delivered between the bronchiolar device 1000 and the alveolar device, can be removed. Membrane 1008 includes fluid port 1024, which can be aligned with inlet 1018 of second substrate 1010. Membrane 1008 can also include fluid ports 1026, which can be fluidly coupled to fluid ports 1028 of first substrate 1002 and fluid ports 1030 of second substrate 1010. An exemplary embodiment of a branching bronchiolar device is illustrated in FIG. 50.

In some embodiments, the bronchiolar devices disclosed herein can be used to grow cells, tissue, or a combination thereof that can associate with one or more components of the bronchiolar device. In some embodiments, one or more cell populations can be introduced into the bronchiolar device using one or more of the inlets disclosed herein. For example, populations of cells can be introduced into the device so that the cells come into contact with one or more hollow tubes or bronchiolar membrane included within the bronchiolar device. For example, in some embodiments, cells can be introduced as a solution or suspension, into an inlet that is fluidly coupled to one or more hollow tubes or a bronchiolar membrane positioned within the device. In some embodiments, a first population of cells can be introduced into an inlet that is fluidly coupled to a central lumen of a hollow tube or a first side of a bronchiolar membrane and a second population of cells can be introduced into an inlet that is fluidly coupled to an incubation chamber through which the hollow tube passes or to a second side of a bronchiolar membrane. Accordingly, in such embodiments, a first population of cells can be associated with (e.g., attached to) to the surface of the central lumen of the hollow tube or a first side of the bronchiolar membrane, and a second population of cells can be coupled to the exterior of the elongated body of the hollow tube or a second side of the bronchiolar membrane. Cells that are coupled to the perimeter of the central lumen or a first side of the bronchiolar membrane can be exposed to a first fluid introduced into the device, such as air, gas, or a combination thereof, and cells that are coupled to the exterior of the elongated body or a second side of the bronchiolar device can be exposed to a second fluid introduced into the device, such as a biological medium. In other embodiments, the cells can be associated with the exterior of the central lumen, the exterior of the elongated body, or the second side of the bronchiolar membrane prior to assembly of the device.

B. Alveolar Devices

Also disclosed herein are embodiments of alveolar devices that can be used in combination with the disclosed bronchiolar devices to make a lung organ device. Embodiments of the disclosed alveolar devices can be used to mimic the physical expansion and contraction of alveolar sacs present in a lung. The disclosed alveolar devices also can provide a biological environment similar to that which exists in a lung organ, such as the alveolar-capillary wall.

In some embodiments, the alveolar devices disclosed herein include at least two components that can be used to mimic alveolar sacs present in a lung organ. The at least two components include a first portion that is capable of being fluidly coupled with a first fluid that passes from a bronchiolar device embodiment to the alveolar device, and a second portion that is capable of being fluidly coupled with a second fluid that passes through the bronchiolar device. In particular disclosed embodiments, the first portion can be a fluid-compatible component that is used to facilitate delivery of a fluid (e.g., air, gas, or a combination thereof) through the alveolar device and the second portion can be a medium-compatible component that is used to facilitate deliver of a fluid different from that in the fluid-compatible component (e.g., a biological medium, such as a blood surrogate) through the alveolar device. The device also can further include a membrane component. In some embodiments, the fluid-compatible component and the medium-compatible component can be coupled together through the membrane component. For example, the membrane component can be positioned between the fluid-compatible component and the medium-compatible component. The membrane component typically includes an airway side, which is understood herein as referring to the side of the membrane that faces the fluid-compatible component, and a vascular side, which is understood herein as referring to the side of the membrane that faces the medium-compatible component.

In some embodiments, the fluid-compatible component of embodiments of the alveolar device can be configured to be in fluid communication with fluid from the bronchiolar device, such as air or gas that passes through the bronchiolar devices via one or more connecting tubes. The medium-compatible component can be configured to be in fluid communication with medium that is delivered from the bronchiolar device to the alveolar device via one or more tube lines or connecting tubes as disclosed herein.

In some embodiments, the fluid-compatible component includes a plurality of substrates that can be coupled together. The medium-compatible component also includes a plurality of substrates that can be coupled together. Both the fluid-compatible component and the medium-compatible component can be configured to include at least one channel. In some embodiments, the fluid-compatible component includes at least one air chamber fluidly coupled to at least one channel and the medium-compatible component includes at least one medium chamber fluidly coupled to at least one channel.

Figure 51:
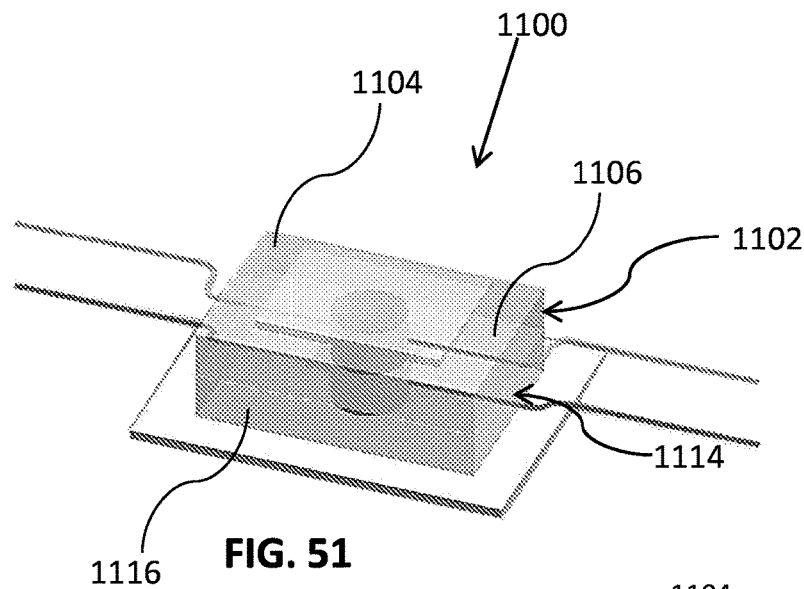
FIG. 51 illustrates an embodiment of an alveolar device as disclosed herein.
Figure 52:
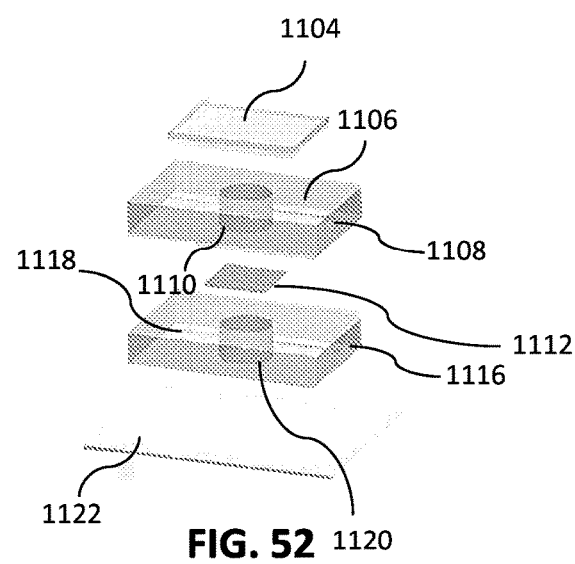
FIG. 52 is an exploded perspective view of the alveolar device embodiment illustrated in FIG. 51, further illustrating various components of the device.

Some embodiments of the fluid-compatible component include a first substrate (such as a bottom substrate) having at least one channel that is fluidly coupled to at least one air chamber and a second substrate (such as a top substrate) configured to cover the one or more air chambers. Such embodiments can be coupled with a medium-compatible component that includes a first substrate (such as a top substrate) having at least one channel fluidly coupled to at least one medium chamber and a second substrate (such as a bottom substrate) coupled to the first substrate. The medium-compatible component can further include one or more medium chambers. In some embodiments, the fluid-compatible component and the medium-compatible component can have the same or different number of air and medium chambers. An exemplary embodiment of an alveolar device comprising such air- and medium-compatible components is illustrated in FIGS. 51-54. As illustrated in FIGS. 51 and 52, alveolar device 1100 includes a fluid-compatible component 1102, comprising a second (or top) substrate 1104, and a first (or bottom) substrate 1106. As illustrated in FIG. 52, the first (or bottom) substrate 1106 includes channel 1108 and air chamber 1110 through which fluid, such as air, gas, or a combination thereof, can flow from a bronchiolar device embodiment into and out of alveolar device 1100.

Figure 53:
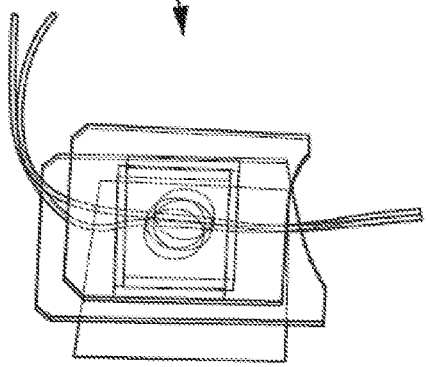
FIG. 53 shows a top view of a working example of the alveolar device illustrated in FIG. 51.
Figure 54:
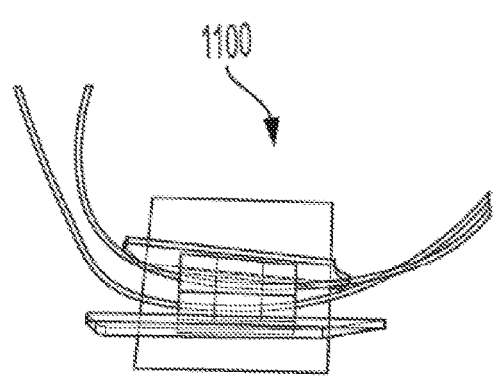
FIG. 54 shows a side view of the working example shown in FIG. 53.

A membrane component 1112 can be included in device 1100, and can be positioned between fluid-compatible component 1102 and a medium-compatible component 1114. Medium-compatible component 1114 includes a first (or top) substrate 1116, which includes channel 1118 and medium chamber 1120 through which fluid, such as a biological medium, can flow from a bronchiolar device embodiment into and out of alveolar device 1100. A second (or bottom) substrate 1122 can also be included and positioned below first (or top) substrate 1116. An exemplary embodiment of device 1100 is shown in FIGS. 53 and 54. FIG. 53 is a top view of device 1100 and FIG. 54 is a side view of device 1100.

Figure 55:
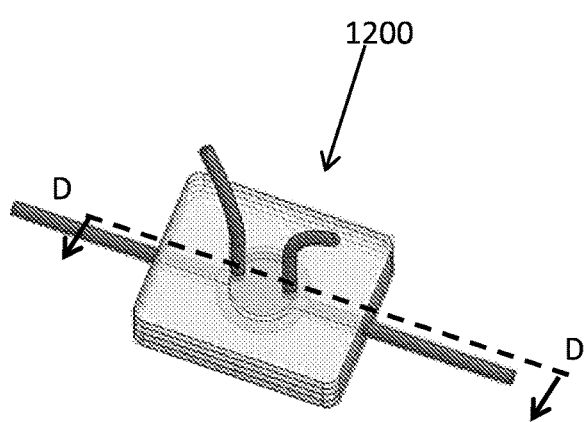
FIG. 55 illustrates another exemplary alveolar device.
Figure 56:
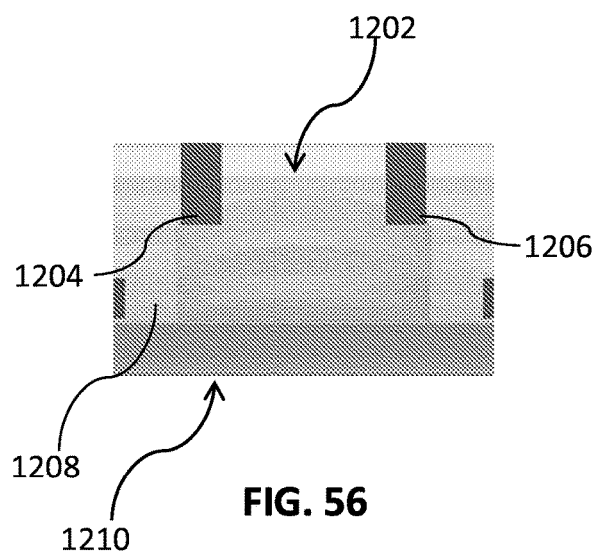
FIG. 56 is a cross-sectional view taken along axis D-D of the alveolar device illustrated in FIG. 55.
Figure 57:
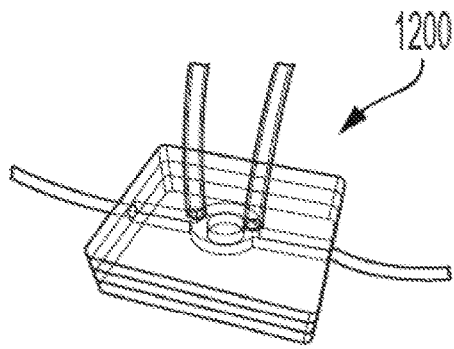
FIG. 57 show a working example of the bronchiolar device illustrated in FIG. 55.
Figure 58:
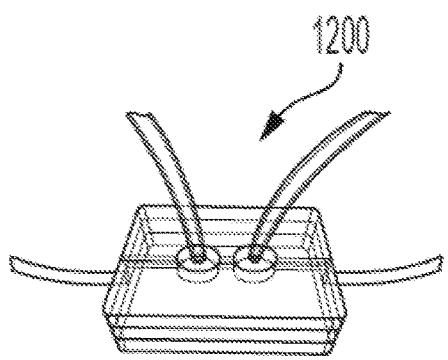
FIG. 58 show a working example of the bronchiolar device illustrated in FIG. 55, wherein two fluid chambers are provided.

In some embodiments, the alveolar device includes alternative configurations of the various components described above. For example, FIGS. 55-58 illustrate alternative configurations of the fluid-compatible component. FIG. 55 illustrates a top view of device 1200. As further illustrated in FIG. 56, device 1200 includes a fluid-compatible component 1202 comprising an inlet 1204 and an outlet 1206 that are positioned perpendicularly to channel 1208 of medium-compatible component 1210. An exemplary embodiment of device 1200 is shown in FIG. 57. In some embodiments, more than one medium chamber and air chamber can be provided in an alveolar device, as shown in FIG. 58.

In yet other embodiments, the alveolar device includes a fluid-compatible component and a medium-compatible component, each of which includes a plurality of substrates having a plurality of channels in fluid communication with one another. In some embodiments, the substrates of the fluid-compatible component and the medium-compatible component include a polymeric material selected from, but not limited to polydimethylsiloxane (PDMS), and/or acrylic or polycarbonate materials. The number of substrates that are used can range 1 to 2500 substrates, such as 100 to 1024 substrates, or 100 to 400 substrates. In some embodiments, the substrates can have the same thickness, or progressively increasing thicknesses. Substrate thicknesses can range from 1 μm to 2 mm, such as 1 μm to 1 mm, or 1 μm to 0.5 mm. In exemplary embodiments, the substrate thickness can be selected from 1 μm, 100 μm, 200 μm, 0.2 mm, 0.5 mm, and 1 mm.

Figure 59A:
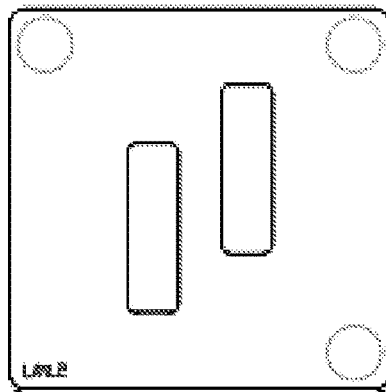
FIGS. 59A-59I illustrate embodiments of substrates that can be used to make a fluid-compatible component of an alveolar device.
Figure 59B:
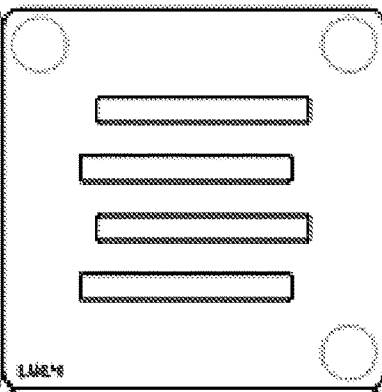
Figure 59C:
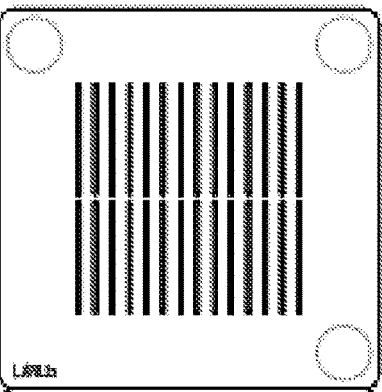
Figure 59D:
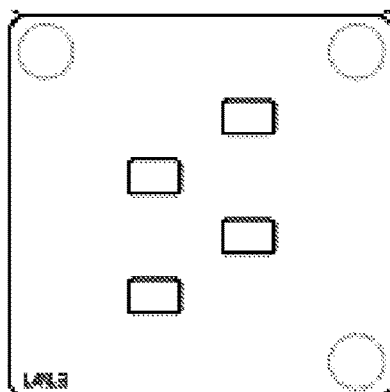
Figure 59E:
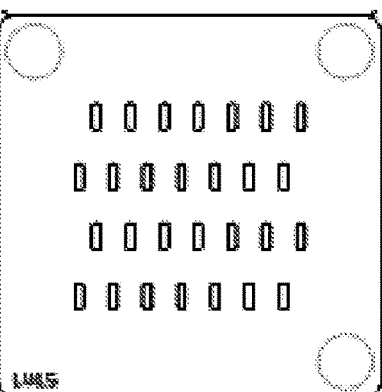
Figure 59F:
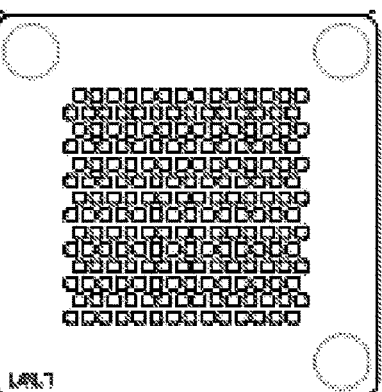
Figure 59G:
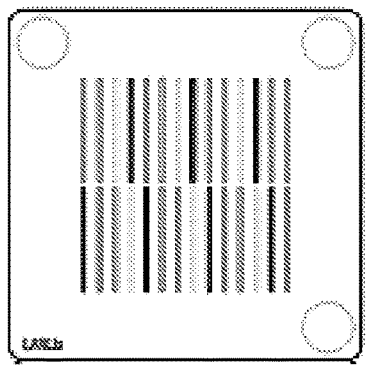
Figure 59H:
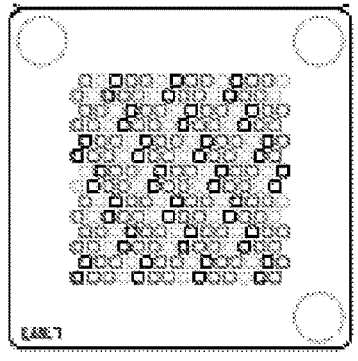
Figure 59I:
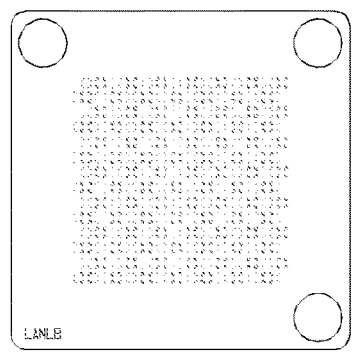

In some embodiments, the substrates include a plurality of channels that can be fluidly coupled to one another when the device is assembled by stacking substrates on top of each other. In some embodiments, the channels can have configurations that differ with each substrate. Exemplary substrates having a variety of channel configurations suitable for use as substrates for the fluid-compatible component are illustrated in FIGS. 59A-59I. FIGS. 59G-59I further illustrate the various flow paths created by each substrate and the channels formed therein. FIGS. 60A-60H illustrate exemplary channel shapes and configurations of the substrates that can be used for the medium-compatible component.

A membrane component can be coupled with such fluid-compatible and medium-compatible components. In some embodiments, the membrane can be a single membrane, or a plurality of membranes, which can be suspended on and bonded to apertures present on a polymeric support. In some embodiments, a substrate comprising a plurality of apertures can be covered with a single membrane layer that covers each aperture. In some embodiments, each aperture present in the substrate can individually be covered with a membrane segment. Embodiments comprising a plurality of apertures can be used to mimic the activity of a lung alveolar sac. In exemplary embodiments, the membrane component comprising a plurality of apertures can be used to form an alveolar sac mimetic having a surface area of 98 mm$^2$, thus providing a total alveolar sac surface area of 500 mm$^2$.

Any suitable material may be used to make the membrane material of the membrane component. In some embodiments, the membrane material can be an elastic, polymeric material capable of resilient deformation and reformation (e.g., such as expanding to form a semi-sphere and contracting back to its original shape, or resting state, such as the shape it retains when no external force is exerted on the material to force it to expand). The material, however, should not be so elastic as to lose its shape over an extended period of time (e.g., time periods ranging from hours to days to weeks to months). In exemplary embodiments, the membrane material can tolerate up to 170 cm H$_2$O. The membrane material also should be permeable so as to allow for gas exchange to occur. In some embodiments, the membrane material includes a polyester material, such as poly-L-lactic acid, or a polysiloxane material, such as polydimethylsiloxane, polycaprolactone (PCL), PLLA-PCL copolymer, polyester, polycarbonate, or a combination thereof. In some embodiments, the membrane material can further include a collagen material, such as a collagen type I material. The membrane material can be associated with a substrate to form the membrane component using methods like spin coating, dip coating, or the like.

In particular disclosed embodiments, the apertures to which the membranes may be bonded can have diameters ranging from 0.1 to 10 mm, such as 0.5 to 5 mm, or 0.5 to 2 mm. In exemplary embodiments, the apertures can have a diameter of 0.4 mm. In some embodiments, each aperture can be separated by a distance of 0.1 to 10 mm, such as 0.5 to 5 mm, or 0.5 to 2 mm.

Figure 61A:
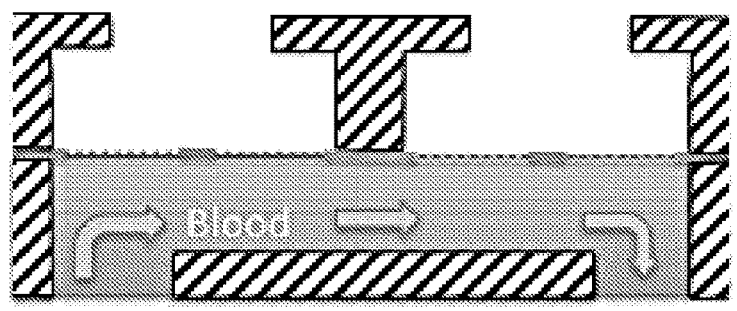
FIGS. 61A and 61B are schematic diagrams illustrating the behavior of the membrane component of alveolar device embodiments disclosed herein.
Figure 61B:
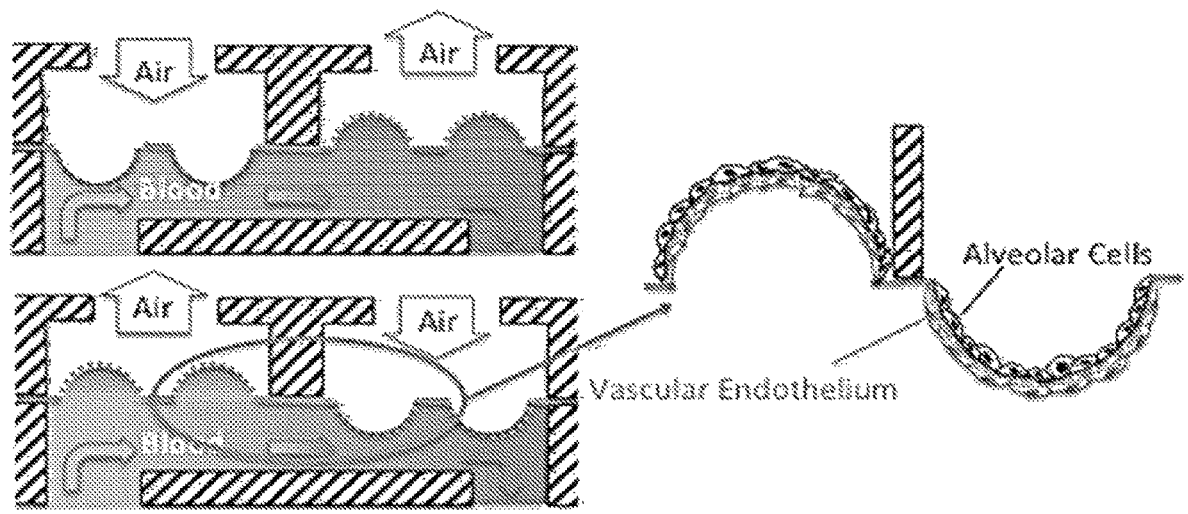
Figure 62A:
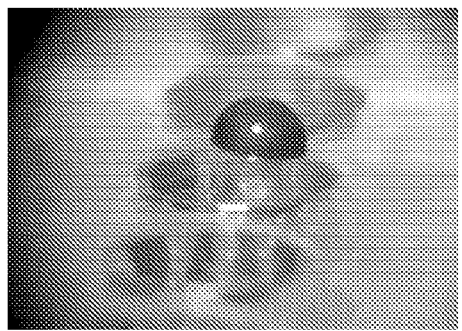
FIGS. 62A-62D show embodiments of the membrane component used in alveolar devices disclosed herein as air forces the membrane to expand or inflate (FIGS. 62A and 62C) and as air is expelled and the membrane is allowed to contract back to its resting state (FIGS. 62B and 62D).
Figure 62B:
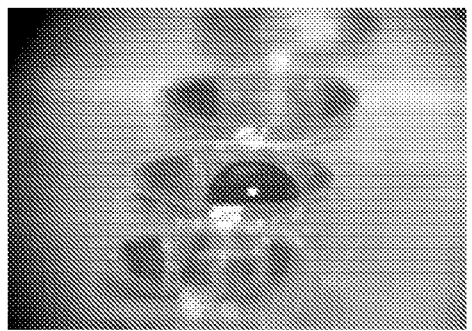
Figure 62C:
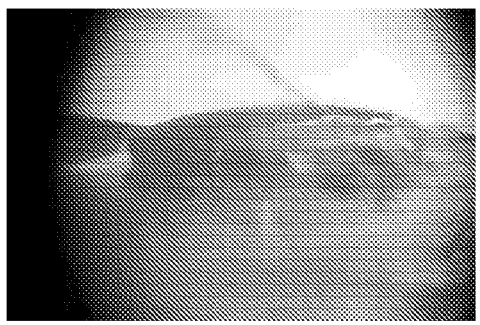
Figure 62D:
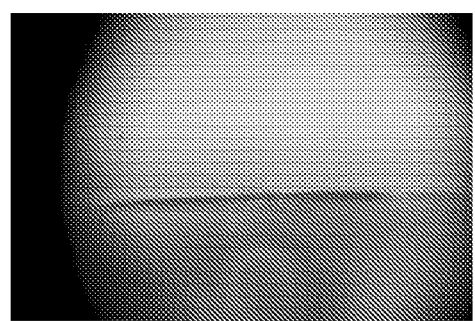

In particular disclosed embodiments, the polymeric supports include 1 to 2500 apertures, such as 100 to 1024 apertures, or 100 to 400 apertures. In exemplary embodiments, 700 to 800 apertures can be included in the substrate coupled to the membrane. The apertures present on the polymeric support can be used to mimic alveoli of a lung organ of a human or other mammal as the membrane can expand through the aperture and relax back to its original state as air enters and exits the alveolar device. FIGS. 61A, 61B, and 62A-62D illustrate exemplary embodiments of a membrane component and membrane material as it is inflated and deflated. FIGS. 61A and 61B are schematic illustrations of how the membrane material reacts to forces that cause the membrane to inflate and deflate; FIG. 61A illustrates the membrane component as it behaves in a steady state and FIG. 61B illustrates the membrane material as air enters and exits the alveolar device and acts upon the membrane material. FIGS. 62A-62D show exemplary embodiments of membrane materials as they inflate (FIGS. 62A and 62C) and deflate (FIGS. 62B and 62D).

As indicated above, the membrane can be positioned between the fluid-compatible and the medium compatible components. In some embodiments, the fluid-compatible component can be positioned on top of one side of the membrane component and the medium-compatible component can be positioned below and on the other side of the membrane components. In embodiments using such an arrangement, one side of the membrane can be in fluid contact with a medium (e.g., blood surrogate or biological medium) passing from the bronchiolar device and one side of the membrane can be in fluid contact with fluid (e.g., air or gas) passing from the bronchiolar device.

Figure 63:
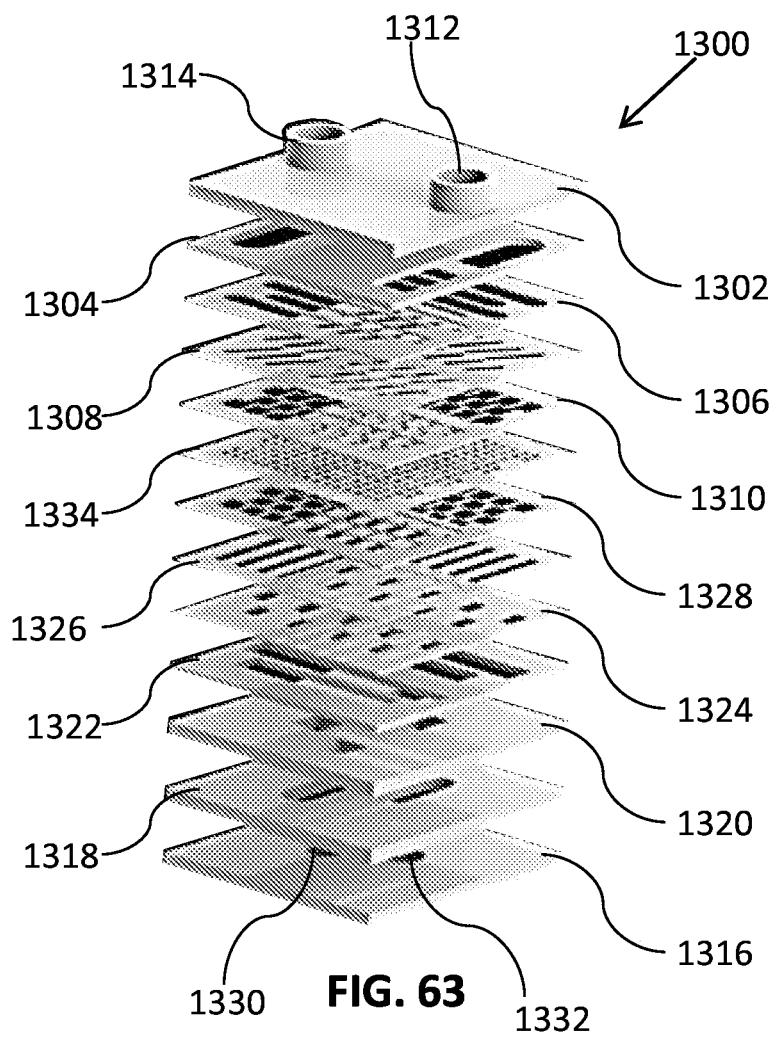
FIG. 63 shows an exploded perspective view of an exemplary alveolar device comprising a plurality of substrates that forms the fluid-compatible component, a membrane component, and a plurality of substrates that forms the medium-compatible component.
Figure 64:
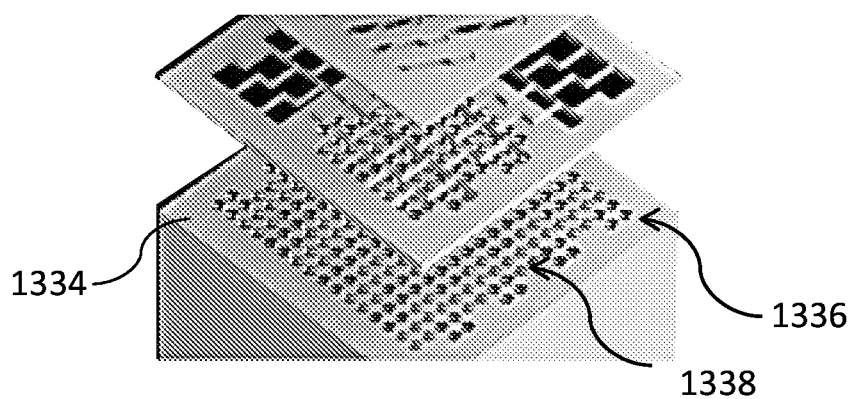
FIG. 64 shows an exploded expanded view of the membrane component shown in the device of FIG. 63.
Figure 65:
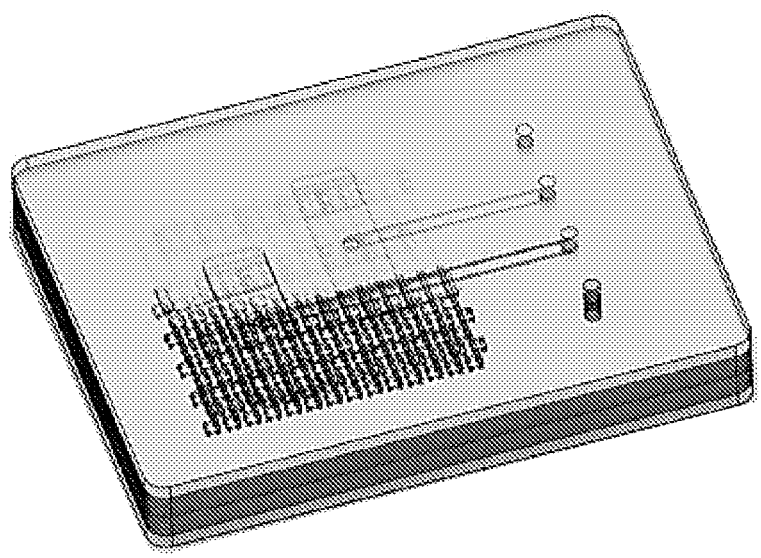
FIG. 65 illustrates an exemplary embodiment of a constructed alveolar device.
Figure 66:
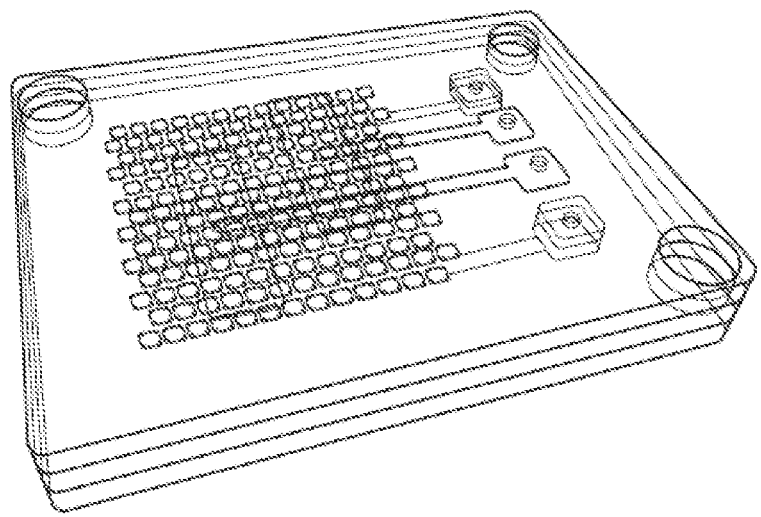
FIG. 66 shows a working example of the alveolar device illustrated in FIG. 65.

FIG. 63 provides an exploded perspective view of an alveolar device 1300. A first set of substrates 1302, 1304, 1306, 1308, and 1310 can be sequentially stacked to provide a fluid-compatible portion of alveolar device 1300. Substrate 1302 includes an inlet 1312 and an outlet 1314 through which a fluid, such as air, gas, or a combination thereof, can be introduced from a bronchiolar device. A second set of substrates 1316, 1318, 1320, 1322, 1324, 1326, and 1328 can be sequentially stacked to provide the medium-compatible portion of alveolar device 1300. Substrate 1316 can be configured to include fluid ports 1330 and 1332 through which a fluid, such as a biological medium, can be introduced from a bronchiolar device. Membrane component 1334 can be placed between the substrates forming the fluid-compatible component and the substrates forming the medium-compatible component. As illustrated in FIG. 64, a plurality of apertures can be provided in the membrane component 1334. Membrane component 1334, as illustrated in FIG. 64, can be configured to include a plurality of aperture subsets 1336 and 1338 that can be independently inflated or deflated as a fluid, such as air, gas, or a combination thereof, is introduced from the bronchiolar device and expelled through the alveolar device. FIGS. 65 and 66 illustrate exemplary constructed alveolar devices that can be used in the disclosed lung organ device.

Figure 67:
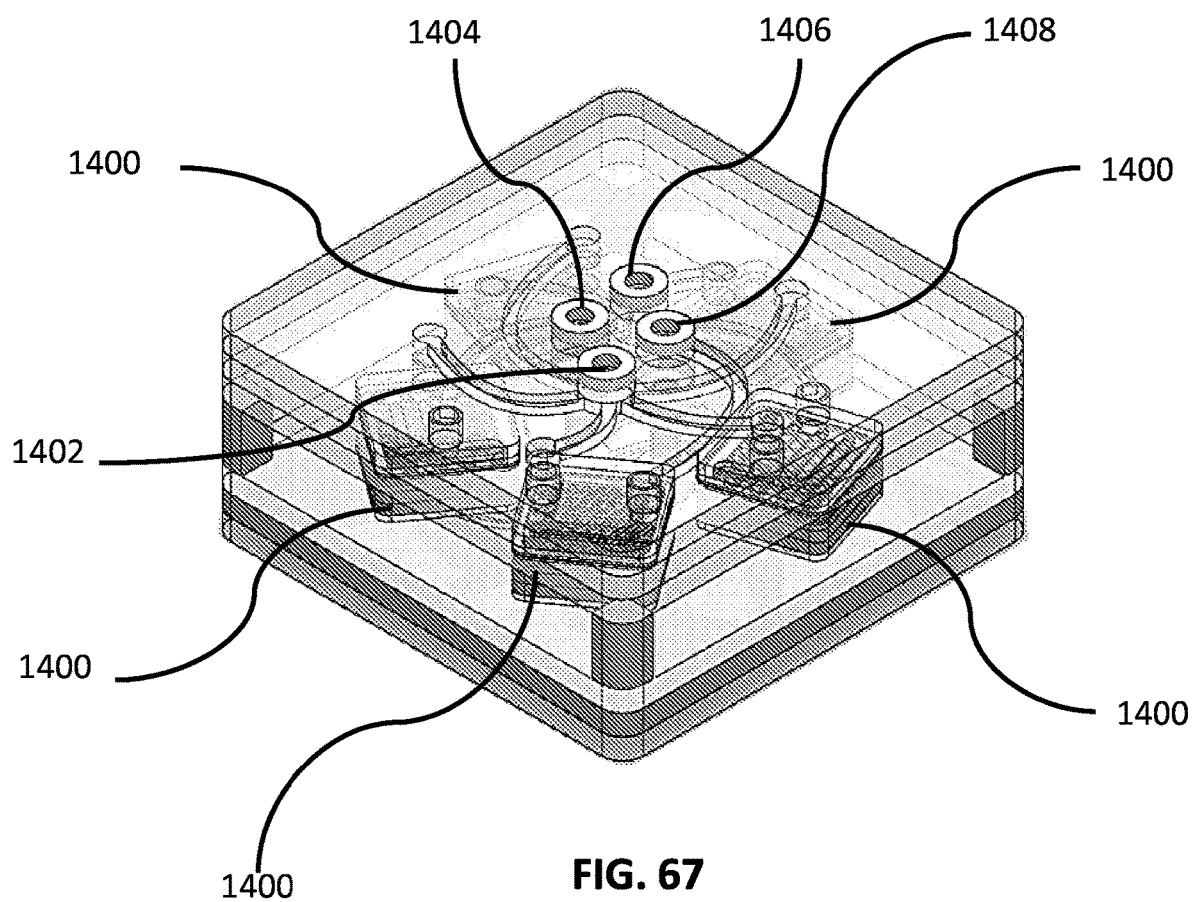
FIG. 67 illustrates another embodiment of a constructed alveolar device comprising a plurality of alveolar components.

In some embodiments, the alveolar device includes a plurality of coupled fluid-compatible and medium-compatible components disclosed above. This plurality of devices can be combined with a bronchiolar device. An exemplary embodiment of an alveolar device comprising is illustrated in FIG. 67. As illustrated in FIG. 67, a plurality of alveolar devices 1400 can be fluidly coupled to a bronchiolar device (not illustrated) through a common inlets 1402 and 1404, and common outlets 1406 and 1408. In some embodiments, a plurality of alveolar devices can be coupled to a branching bronchiolar device and/or a non-branching bronchiolar device.

Figure 68:
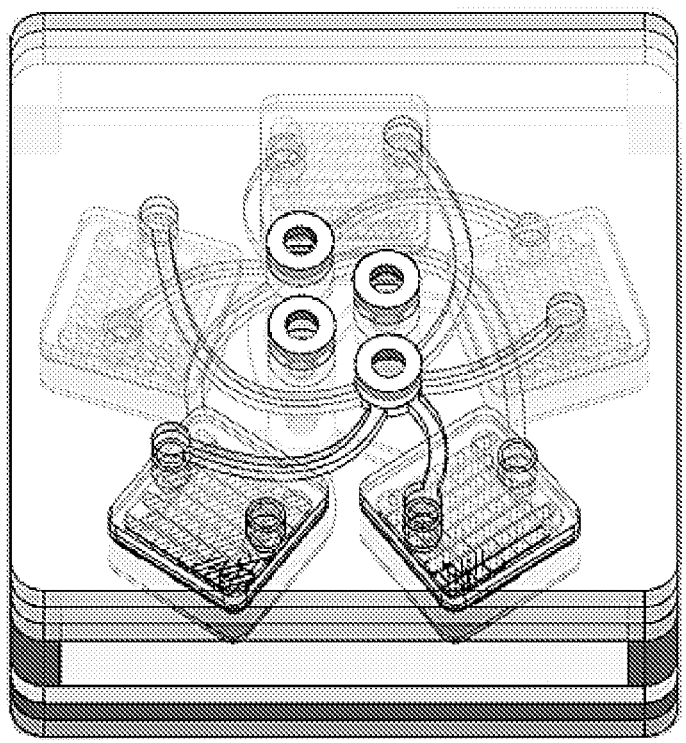
FIG. 68 is a top perspective view of the device embodiment illustrated in FIG. 67.
Figure 69:
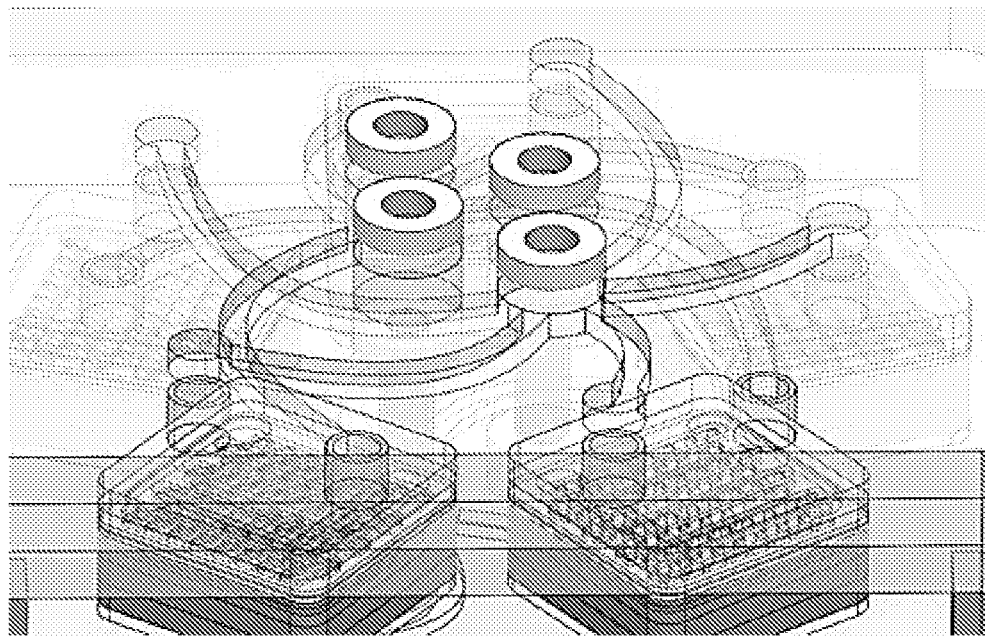
FIG. 69 is a side perspective view of the device embodiment illustrated in FIG. 67 and further illustrates common inlets and outlets connecting the plurality of alveolar components.

In some embodiments, an alveolar device includes a plurality of single alveolar units. In such embodiments, each single alveolar unit can be coupled to a first inlet and outlet fluidly coupled to a bronchiolar device, which deliver and remove a first fluid to and from the alveolar device, respectively. In such embodiments, a second inlet and outlet fluidly coupled to the bronchiolar device, which deliver and remove a second fluid to and from the alveolar device. FIGS. 68 (top view) and 69 (side view) illustrate one possible configuration of substrates 1500 and 1600 that can be used to couple a plurality of alveolar devices to a bronchiolar device.

Figure 70:
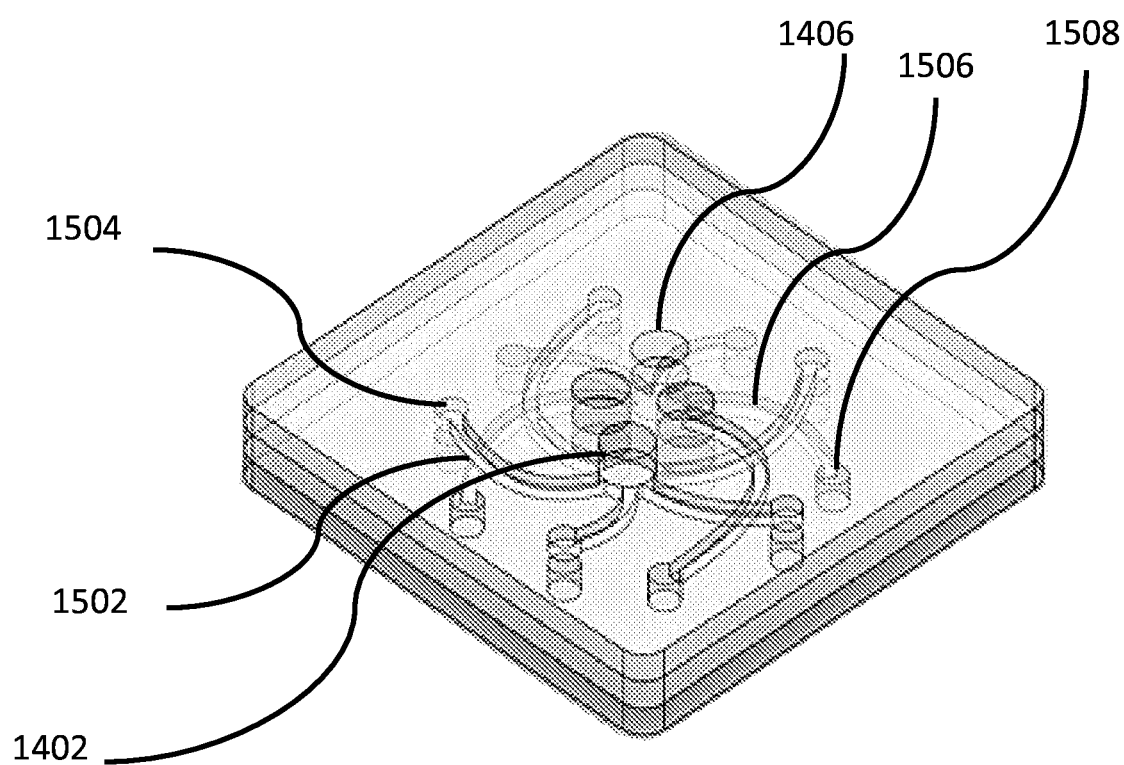
FIG. 70 illustrates an exemplary substrate that can be used to connect a plurality of alveolar components to a common fluid inlet and outlet used to deliver a first fluid to and from the alveolar device.
Figure 71:
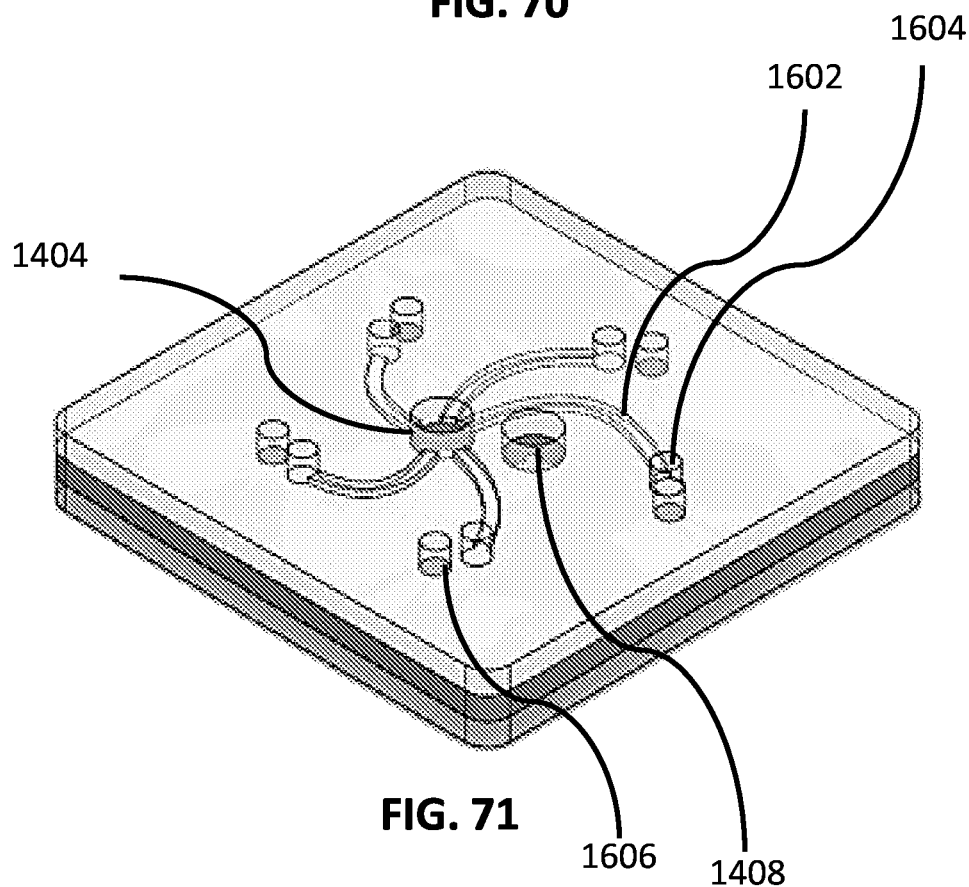
FIG. 71 illustrates an exemplary substrate that can be used to connect a plurality of alveolar components to a common fluid inlet and outlet used to deliver a second fluid to and from the alveolar device.

As illustrated in FIG. 70, substrate 1500 includes a plurality of channels 1502, which can extend from common inlet 1402 to inlets 1504 of each singular alveolar unit (1400, FIG. 67). Substrate 1500 can also include a common outlet 1406 that can be fluidly coupled to a plurality of channels 1506 that can provide fluid communication between common outlet 1406 and individual outlets 1508 of each singular alveolar unit. Inlets 1504 and outlet 1508 can be used to deliver a first fluid, such as air, gas, or a combination thereof, from the bronchiolar device to each alveolar unit 1400. Similarly, substrate 1600, illustrated in FIG. 71, includes a plurality of channels 1602, which can extend from a common inlet 1404 to inlets 1604 of each singular alveolar unit (1400, FIG. 67). Common outlet 1408 can be fluidly coupled to a plurality of channels (not illustrated) that direct a second fluid, such as a biological medium, from outlets 1606 to the common outlet 1408.

Figure 72:
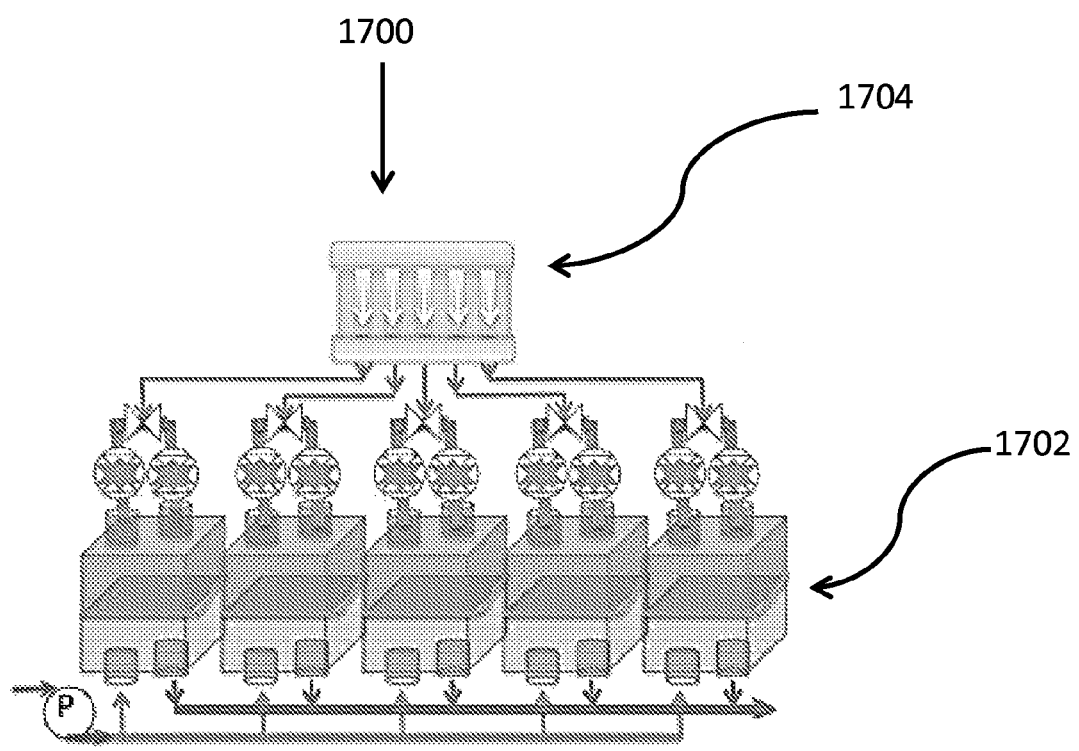
FIG. 72 illustrates an exemplary configuration of a lung organ device wherein a bronchiolar device is fluidly coupled to an alveolar device comprising a plurality of alveolar components.

While exemplary configurations of the plurality of alveolar units are illustrated in the above disclosed embodiments, any suitable configuration can be used. For example, the individual alveolar units can be arranged in any configuration and common inlets 1402, 1404 and common outlets 1406, 1408 can be arranged in any position relative to the individual alveolar units. For example, FIG. 72 provides an alternative arrangement of the components of a lung organ device 1700 comprising a plurality of individual alveolar units 1702 and a single bronchiolar device 1704. Any number of individual alveolar units can be used to make an alveolar device comprising a plurality of such units.

The alveolar device embodiments disclosed herein can be used to grow cells and/or tissue that can be used to mimic biological and physical responses experienced by cells and/or tissue within a lung organ. In some embodiments, one or more cell types can be introduced into the alveolar device so that the cells can attach to or associate with the membrane material of the membrane component of the alveolar device. In other embodiments, the cells can be attached to or associated with the membrane material prior to assembly of the device. In some embodiments, attachment of cells can occur through covalent or electrostatic interactions between the cells and the membrane material.

Figure 73A:
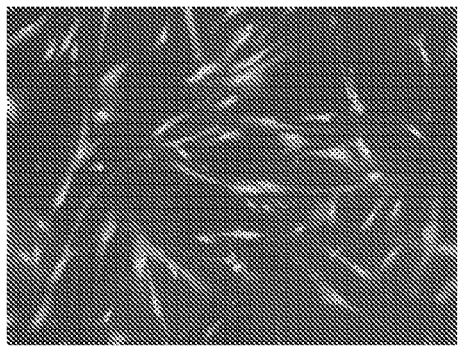
FIGS. 73A-73D show examples of cell populations that can be grown on the membrane component of the alveolar devices disclosed herein.
Figure 73B:
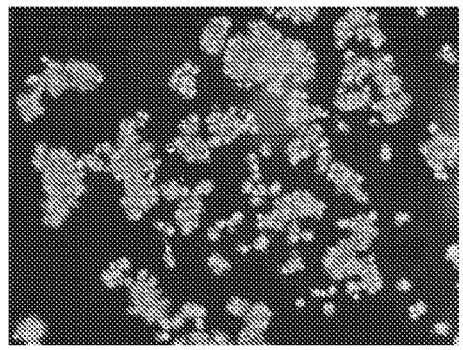
Figure 73C:
Figure 73D:
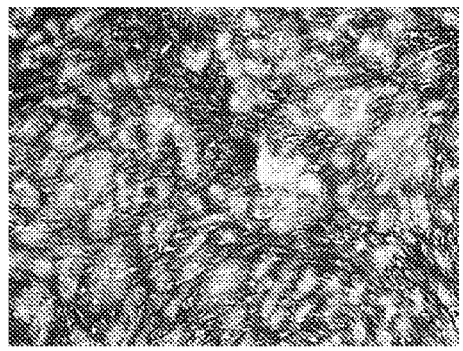

In some embodiments, a first population of cells can be associated with one side of the membrane material of a membrane component and a second population of cells can be associated with the opposite side of the membrane material. For example, a first population of immune responsive cells, surfactant-producing cells, or a combination thereof, can be associated with the side of the membrane material that is in fluid communication with the fluid-compatible component of the alveolar device (e.g., apical side), and a second population of cells, such as pulmonary microvascular cells, human lung microvascular endothelial cells, human lung smooth muscle cells, human lung fibroblast cells, monocytes, dendritic cells, or a combination thereof can be associated with the opposite side of the membrane that is in fluid communication with the medium-compatible component of the alveolar device (e.g., basolateral side). In exemplary embodiments, alveolar type 1 cells (AT1), alveolar type 2 cells (AT2), and combinations thereof can be used on the fluid-compatible side (or apical side) of the membrane and alveolar cells, such as A549 cells, H441 cells, AT1, and/or AT2 cells can be used on the medium-compatible side (or basolateral side) of the membrane. In some embodiments, the attachment or association of cell populations to different sides of the membrane material of the membrane component can facilitate gas exchange between the first and second fluids introduced into the alveolar device from the bronchiolar device. For example, in embodiments using air, gas, or a combination thereof, as a first fluid and a biological medium, such as a blood surrogate, as a second fluid, the cell populations can facilitate exchange of $CO_2$ and $O_2$ across the membrane. FIGS. 73A-73D illustrate exemplary embodiments of cells that can be associated with the membrane component. FIGS. 73A and 73B illustrate the effect of mechanical stretch on AT1 (FIG. 73A) and AT2 cells (FIG. 73B). FIGS. 73C and 73D illustrate the effect of air flow of HLMVE cells associated with the basolateral side (FIG. 73C) of a membrane component and AT1 cells associated with the apical side (FIG. 73D) of the membrane component.

In some embodiments, the surface area of the membrane material (either the entire membrane, or the portion that is present in each aperture of the membrane component) that is covered by a particular cell population can be controlled to provide a particular environment. For example, the cell populations present on the fluid-compatible side of the membrane can be controlled so that differentiation of one cell type into another cell type (e.g., AT2 to AT1 cells) can be prevented if so desired. Cell differentiation also can be controlled by manipulating the mechanical stress applied to the cell populations when the alveolar device is in use. For example, inhalation (in vivo and/or as simulated using a device embodiment disclosed herein) can cause distension and significant volume fluctuations with consequent mechanical stress on the membrane of the alveolar wall which is primarily composed of extracellular matrix (ECM) and collagen-producing fibroblasts. The mechanical stretch of the membrane can govern maintenance of the AT1 and AT2 phenotype and cellular function (both in vivo and/or ex vivo using a device embodiment disclosed herein). In some embodiments, mechanical stimuli produced using device embodiments disclosed herein can stimulate the secretion of lung surfactant lipids (such as can be shown in adult rat AT2 cells using explanted lungs). A decrease in surfactant production can result in high surface tension in the alveoli, which can decrease lung compliance, which is often seen in premature infants suffering from infant respiratory distress syndrome. Accordingly, the disclosed device embodiments can be used to evaluate the effects of mechanical stress and/or serve as a device that can be used to test particular disease models.

In some embodiments, the surface area of the membrane material can be made to include more AT1 cells than AT2 cells. For example, in some embodiments, 0% to 100% of the membrane can be covered, or partially covered, with AT1 cells, such as 30% to 90% of the membrane, or 80% to 90% of the membrane. In such embodiments, 0% to 100% of the membrane can be covered, or partially covered, with AT2 cells, such as 10% to 70% of the membrane, or 10% to 20% of the membrane.

C. Coupled Bronchiolar/Alveolar Device Embodiments

Figure 2:
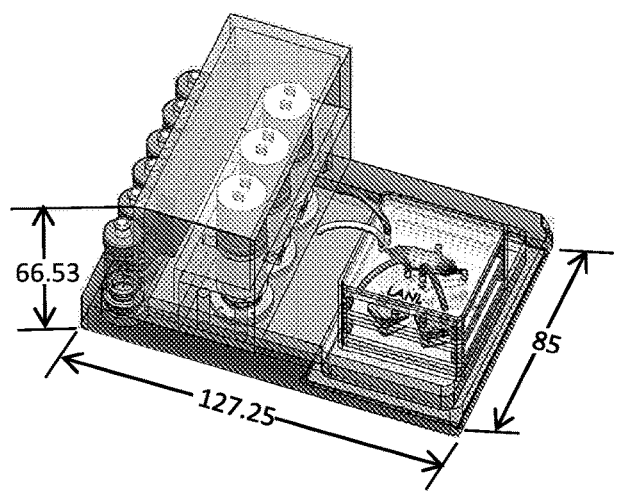
FIG. 2 illustrates an exemplary embodiment of the lung organ device of FIG. 1 and further illustrating an exemplary reservoir platform used with the device.

Bronchiolar device embodiments and alveolar device embodiments disclosed herein can be coupled together to make a lung organ device. In some embodiments, a bronchiolar device and an alveolar device can be mechanically coupled, fluidly coupled, or both. In some embodiments, a single bronchiolar device can be mechanically coupled, fluidly coupled, or both, to an alveolar device comprising a plurality of alveolar units. In some embodiments, one or more tube lines can be attached to the inlets and outlets of the bronchiolar device so as to deliver fluids to and from the alveolar device thereby mechanically and fluidly coupling such devices together. In some embodiments, the assembled lung organ device can be coupled (fluidly and/or mechanically) to a fluid management device as described above. The assembled lung organ devices also can be fluidly coupled to one or more reservoirs suitable for storing fluids that will be introduced into the device (e.g., reservoirs comprising biological media or cells (or compositions thereof)); one or more tanks comprising air and/or gas that will be introduced into the device; one or more pumps capable of recirculating fluids and/or feeding fluids into the device; a bubble trap; one or more waste reservoirs suitable for accepting waste fluid (e.g., biological medium) as it is expelled from the device; one or more sample ports through which samples can be withdrawn from the device for testing; a water trap; and combinations thereof. FIG. 2 provides an exemplary illustration of how such components can be arranged.

Figure 3:
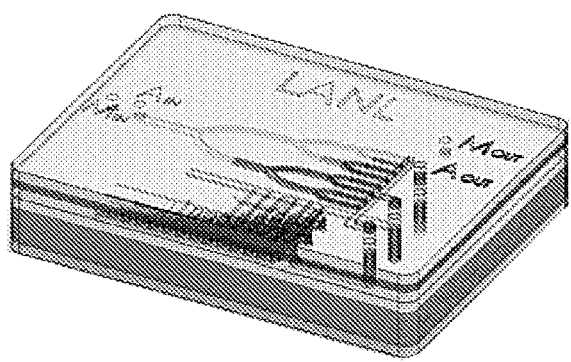
FIG. 3 illustrates an exemplary embodiment of a lung organ device wherein a branching bronchiolar device embodiment is coupled to an alveolar device embodiment.
Figure 4:
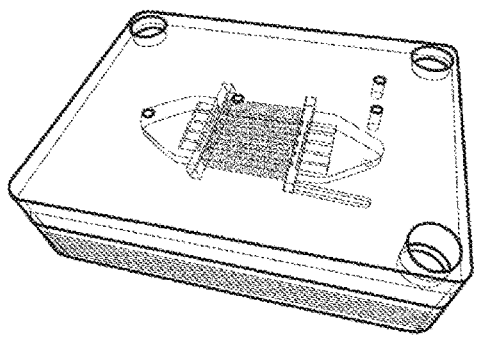
FIG. 4 shows a working example of an exemplary lung organ device embodiment.
Figure 74:
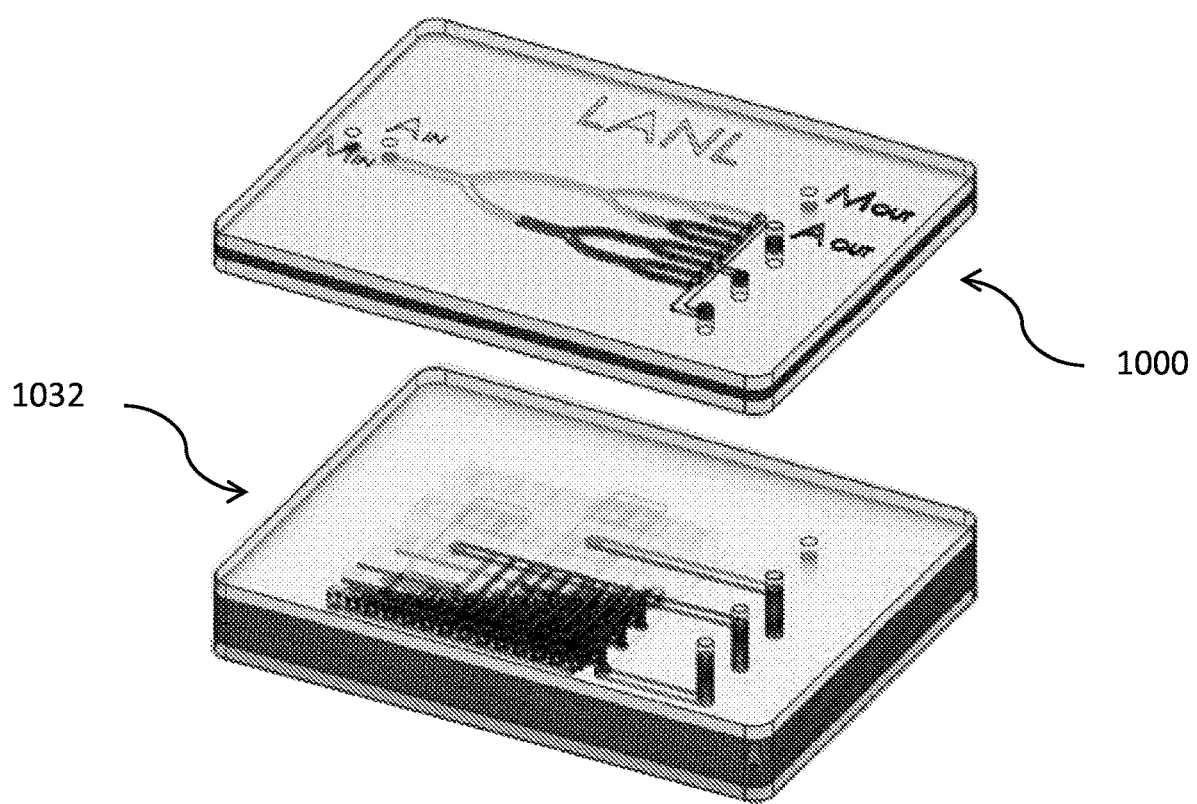
FIG. 74 illustrates the coupling of a branching bronchiolar device with an alveolar device.

In some embodiments, the bronchiolar device is fluidly coupled to the alveolar device so that the fluid ports of the bronchiolar device are aligned with the fluid ports of the alveolar device so that fluids can be transported to and from each device during use. In some embodiments, one or more connecting tubes can be used to fluidly couple the bronchiolar device fluid ports to the inlets and/or outlets (and, in some embodiments, a common inlet and common outlet) of the alveolar device. In an exemplary embodiment, such as that illustrated in FIG. 74, a bronchiolar device 1000 can be coupled to the top of alveolar device 1032 directly without any intervening connecting tubes or components. FIGS. 3 and 4 illustrate such an embodiment. In other exemplary embodiments, connecting tubes can be used to indirectly couple the bronchiolar device to the alveolar device. FIG. 1 illustrates such an embodiment.

Figure 75A:
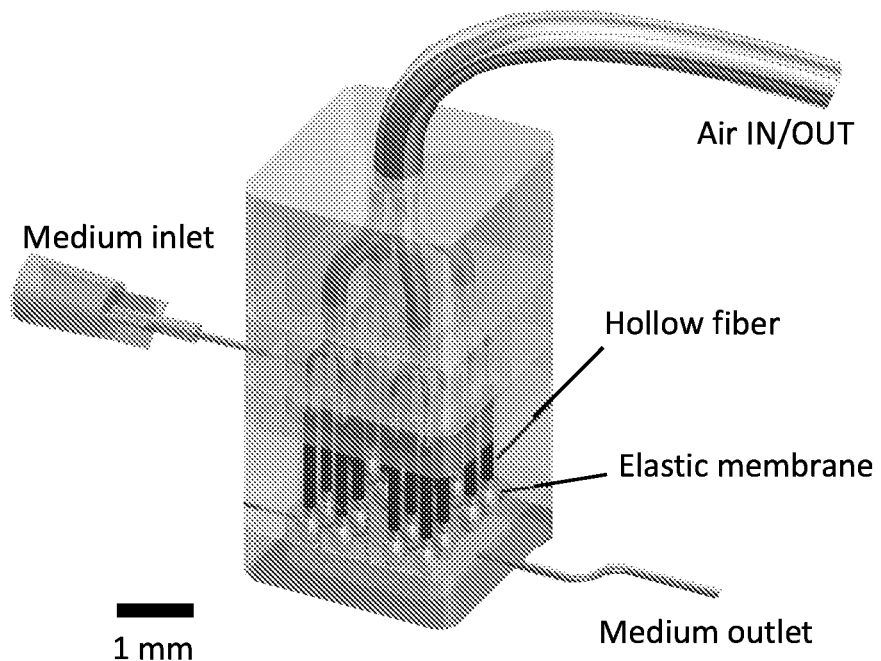
FIGS. 75A and 75B illustrate a constructed lung organ device illustrating how the various components of the device can be used to mimic the functions and geometry of a lung organ.
Figure 75B:
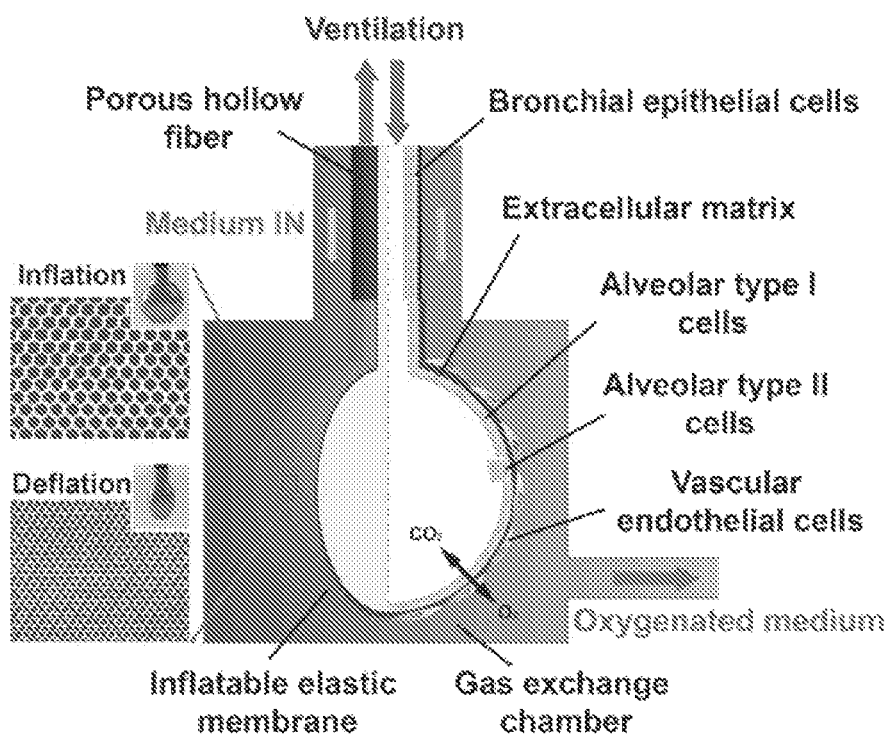

Exemplary embodiments of assembled lung organ devices are illustrated in FIGS. 1-4. A schematic illustrating how a device embodiment mimics the lung architecture of a lung organ is illustrated in FIGS. 75A and 75B.

III. Platform Devices

Disclosed herein are embodiments of a platform device that can be used to facilitate coupling and operation of a plurality of bio-assessment devices (such as 2, 3, 4, 5, or more bio-assessment devices) and their corresponding components. In some embodiments, the platform device can be used to control interactions between a plurality of bio-assessment devices and thereby couple such devices in a manner that allows fluid communication between the bio-assessment devices. In particular disclosed embodiments, the platform device is used to facilitate biological analysis using the plurality of bio-assessment devices and can thereby be used to evaluate the effects of biomedical drugs and/or toxic substances on particular organs of the body without having to administer the drugs in vivo. The platform device can be used in combination with a variety of different bio-assessment devices, each of which is a biomechanical construct of its corresponding human organ counterpart. For example, bio-assessment devices that can be used with the disclosed platform devices include, but are not limited to, lung devices, heart devices, liver devices, kidney devices, and the like.

In particular disclosed embodiments, the platform device comprises a plurality of components that together function to control each bio-assessment device, evaluate operation of each bio-assessment device, and/or control and evaluate the effects of various substances administered into the integrated system. The platform device can comprise a combination of organ sensing and control instrumentation, such as, but not limited to, one or more of an organ perfusion system, an air supply, a fresh media circuit, a recirculation circuit, a microformulator, rotary peristaltic pump(s), rotary planar valve(s), an integrated multi-organ perfusion controller and/or microclinical analyzer, multichannel potentiostat(s), electrode(s), and any combination of two or more thereof. Each of these components is discussed in more detail herein.

In some embodiments, the platform device is configured to fluidly couple the lung organ device to a plurality of bio-assessment devices by including certain of the components described above. In some embodiments, the plurality of bio-assessment devices to which the lung organ device can be coupled includes, but is not limited to, a heart device, a liver device, a kidney device, or other organ devices (such as a vascular device or a neuronal device). The organ devices may be connected in parallel, in series, or a in a configuration combining parallel and serial relationships between the organ devices. In one exemplary embodiment, a heart device (which may include left heart and right heart components) is fluidly coupled to a lung device, a liver device, and a kidney device. One or more of the heart, lung, liver, and kidney devices are fluidly coupled to a fluid transport system including one or more reservoirs, fluidly coupled to fluid inlets and outlets of the organ device(s). In some embodiments, the fluid transport system can comprise a perfusion system as described in more detail herein.

In one exemplary embodiment, a platform device comprises an air supply component (e.g., a ventilator, an air tank, or the like) coupled to a lung organ device, which in turn is fluidly coupled to a heart device, such as a single heart device or a left heart device and a right heart device. In some embodiments, a singular heart device (or a left heart device) is fluidly coupled to a fresh media circuit, which comprises a separate reservoir containing arterial system fluids and/or other nutrients. The fresh media circuit is further fluidly coupled (directly or indirectly) to the fluid inlets of the liver device and the lung organ device, as well as the fluid inlets of a gut microformulator, a kidney device, a multi-organ perfusion controller, a missing organ microformulator, or a combination thereof. The singular heart device (or a right heart device) can be fluidly coupled to a recirculation circuit. The recirculation circuit can comprise a reservoir suitable for accepting fluids delivered from the various bio-assessment devices of the platform device. The recirculation circuit is further fluidly coupled (directly or indirectly) to the lung organ device, a liver device, the kidney device, the multi-organ perfusion controller, a missing organ microformulator, or a combination thereof. Exemplary platform device configurations are provided in U.S. Patent Application Publication No. 2014/0356849, and International Application Publication No. WO 2014/081840, both of which are incorporated herein by reference. Any suitable configuration can be used to couple the bio-assessment devices of the platform device. For example, the bio-assessment devices, including the lung organ devices disclosed herein can be fluidly coupled in parallel, wherein fluid management devices, such as those disclosed in International Patent Application No. PCT/US2015/052043, entitled "DEVICES FOR FLUID MANAGEMENT AND METHODS OF MAKING AND USING THE SAME," filed on Sep. 24, 2015, which is incorporated herein by reference, provide the ability to control each of the bio-assessment devices present in the platform. In yet additional embodiments, one or more of the bio-assessment devices are fluidly connected in parallel, while one or more bio-assessment devices are connected in series. In such embodiments, the serially connected bio-assessment device(s) is coupled parallel to the bio-assessment devices that are connected in parallel. For example, a gastrointestinal organ device (or a missing organ microformulator) can be positioned upstream from a liver organ device, and both of these organ devices can be coupled in parallel to a kidney organ device and one or more of a lung organ device and a heart device. In another embodiment, a heart device can be fluidly coupled in series with a lung organ device, wherein the lung device is fluidly coupled in series to a single heart device, or fluidly coupled in series between both a right heart device and a left heart device. In some embodiments, the platform device provides the ability to bypass one or more bio-assessment devices within the platform device, for example for maintenance, sample collection, or to study the effects of removing one bio-assessment device from the system.

Figure 96:
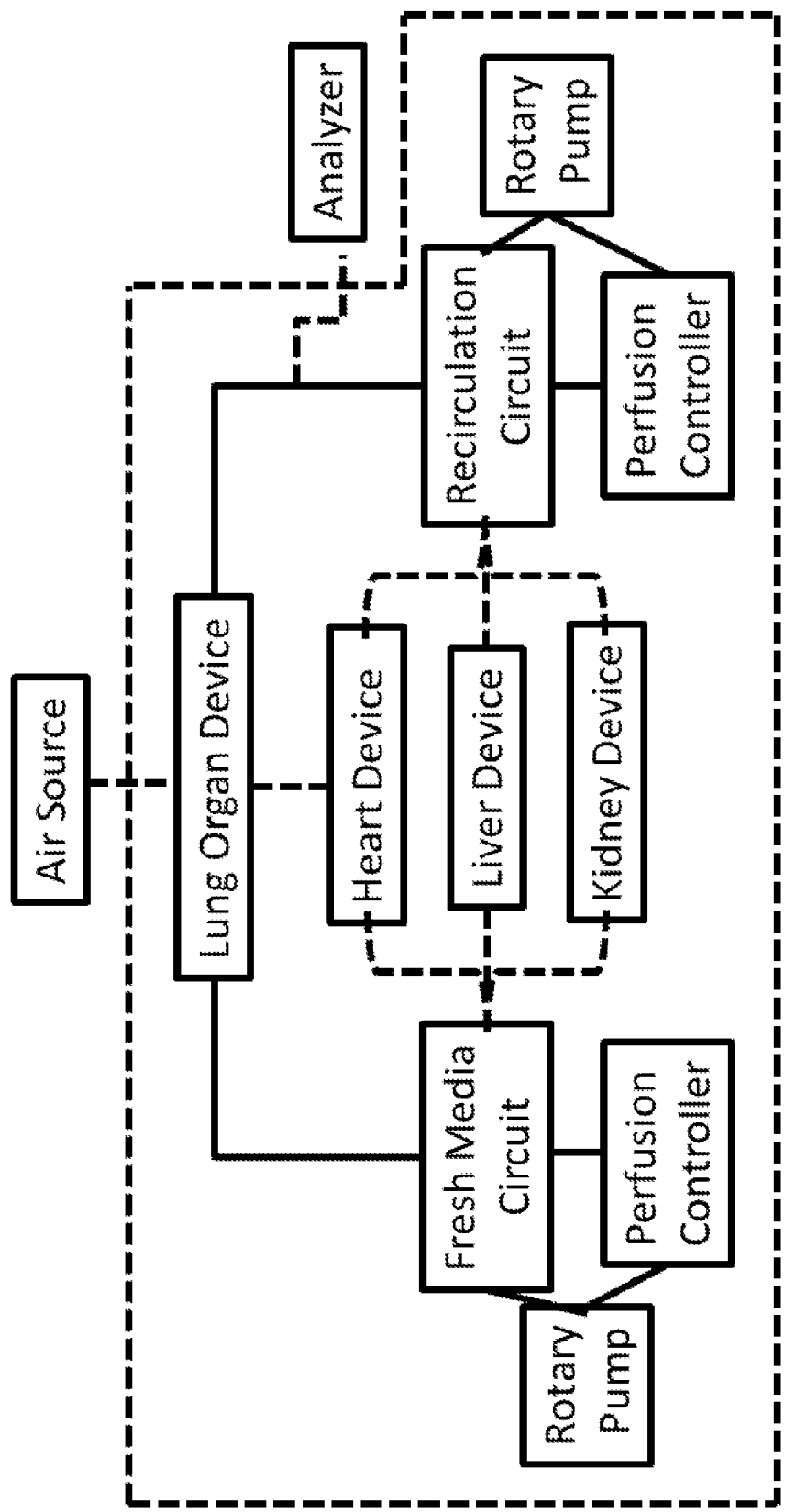
FIG. 96 is a schematic diagram of a representative embodiment of a platform device comprising a plurality of bio-assessment devices.

FIG. 96 is a schematic illustration of an exemplary platform device configuration comprising a lung organ device and a plurality of other optional bio-assessment devices. As illustrated in FIG. 96, an exemplary platform device embodiment can comprise an air source that can be coupled to a lung organ device, which in turn can be fluidly coupled to a heart device. The heart device and the lung organ device are coupled to a fresh media circuit, which can be further fluidly coupled to a liver device and a kidney device. The fresh media circuit also can be coupled to a multi-organ perfusion controller and one or more rotary pumps. As illustrated in FIG. 96, the lung organ device, and any other optional bio-assessment devices can be coupled to a recirculation circuit, which can also be coupled to a perfusion controller and one or more rotary pumps. The platform device can also optionally include an analyzer which can be in fluid communication with the recirculation circuit, the perfusion system, and/or any of the bio-assessment devices. The embodiment illustrated in FIG. 96 is not intended to be limiting, but instead is provided as a representative embodiment to illustrate one possible way in which the components can be arranged using embodiments of the disclosed platform.

In particular disclosed embodiments, an organ perfusion system is used to control fluid flow throughout the platform device and the bio-assessment devices used with the platform device. In some embodiments, the perfusion system comprises a perfusion controller comprising a fluid management system and one or more pumps capable of delivering perfusion fluids, nutrients, and/or biological media. In some embodiments, the organ perfusion system comprises a recirculation circuit (for example, a circuit that continuously circulates medium through the perfusion system) and a fresh media circulation circuit (for example, a circuit that introduces fresh medium into the perfusion system). The perfusion system can comprise one or more pumps that provide media recirculation (e.g., 3 to 300 mL/min) in the recirculation circuit, and fresh media (e.g., 0.5 mL to 50 mL/hr) from the fresh media circulation circuit to the bio-assessment devices. In some embodiments, the perfusion controller of the perfusion system can operate in different modes, such as a bypass control mode, a serial perfusion mode, and an organ replacement perfusion mode. In an embodiment of a bypass control mode, the perfusion controller is used to allow medium (such as blood surrogate or universal medium) to bypass a bio-assessment device, for example so that a different medium can be delivered to the bio-assessment device. In an embodiment of a serial perfusion mode, a bio-assessment device, which is in a serial configuration with one or more bio-assessment devices, is perfused in series with the other bio-assessment devices. In an embodiment of an organ replacement perfusion mode, a bio-assessment device is removed from the platform device and therefore isolated from other bio-assessment devices of the platform device. Flow through the platform device is maintained by utilizing fluid management devices of the bio-assessment devices. A component for analysis, such as a drug, toxin, or other compounds or agents, can then be introduced into the isolated bio-assessment device for evaluation and analysis. In this manner, the effect of one or more compounds on the particular bio-assessment device can be evaluated without exposing other bio-assessment devices to the compound(s). The perfusion system can be fluidly coupled to other components of the platform device and/or the bio-assessment devices or components of the bio-assessment devices. In some embodiments, the perfusion system is fluidly coupled to a recirculation circuit (e.g., a venous system) via one or more inlets and/or a fresh media circuit (e.g., an arterial system) via one or more outlets. In additional embodiments, the perfusion system is fluidly coupled directly to the lung organ device disclosed herein. The perfusion system also can be directly coupled to one or more of a heart device, a liver device, or a kidney device. In yet other embodiments, the perfusion system can be fluidly coupled to a fluid management device that is further fluidly coupled to a bio-assessment device. The perfusion system also can be fluidly coupled to one or more microformulators included in the platform device.

In some embodiments, a computer can be used with the organ perfusion system to regulate variables such as temperature, air, $O_2$, $CO_2$, fluid flow rate, and perfusion pressure. The on-board computer also records culture variables (e.g., pH and $O_2$), and can be used to externally control the perfusion controller and thereby fluid flow into and out of the platform device (and thereby the plurality of bio-assessment devices).

In some embodiments, the platform device can further comprise one or more microformulators. The microformulators can be used to prepare and facilitate precise delivery of desired amounts of perfusion media to the platform device. The microformulators can comprise a plurality of pneumatic microfluidic valves and solenoid valves to deliver perfusate to the bio-assessment devices from the organ perfusion system. In some embodiments, the microformulator is used to deliver nutrients, metabolites, hormones, paracrine signals, and/or drugs or agents to be analyzed using the platform device to one or more bio-assessment devices. In some embodiments, the microformulator is used to deliver nutrients, metabolites, hormones, paracrine signals, and/or drugs or agents being analyzed with the platform device that would be provided by organ devices not included for use in the platform (e.g., a device other than a heart device, lung device, kidney device, or liver device). In such embodiments, the microformulator can be referred to herein as a "missing organ" microformulator. Solely by way of example, a missing organ microformulator can be used in place of endocrine organs, the gut, and the brain and therefore can provide biological components, such as fatty acids and other biologically relevant molecular species. The microformulators can be used to provide controlled additions of nutrients, metabolites, hormones, paracrine signals, and/or drugs or agents to media passed through the platform device and the bio-assessment devices (e.g., fluids, such as blood surrogate, air, and other biological media). A combination of microformulators for use with a bio-assessment device and missing organ microformulators can be used in the platform device. In some embodiments, an individual microformulator can be positioned upstream of each bio-assessment device to provide media supplements specifically required by a particular bio-assessment device. If specific molecules produced by or introduced into a particular bio-assessment device are toxic to another bio-assessment device, a size exclusion filter or an antibody-based affinity separator can be used in conjunction with the microformulator and the bio-assessment device to remove the toxic molecules from the perfusion stream that is fluidly coupled to that bio-assessment device. In particular disclosed embodiments, a microformulator can be used in combination with a countercurrent dialysis system to reduce the local concentration of specific molecules in media passing through the platform device and bio-assessment devices. Representative embodiments of a microformulator are described in U.S. Patent Application Publication No. 2014/0356849 and WO 2014/081840.

The platform devices disclosed herein can comprise one or more peristaltic pumps that are used to facilitate flow of media through the platform device and the various bio-assessment devices used with the platform. The pumps can be miniaturized, such as micropumps or nanopumps. The pumps are optionally used in combination with one or more of the microformulators. In some examples, the pumps are rotary peristaltic pumps such as those described in PCT Publication No. WO/2012/048261, which is incorporated herein by reference, as well as U.S. Patent Application Publication No. 2014/0356849. The peristaltic pumps can be used in combination with rotary planar valves, which also are described in PCT Publication No. WO/2012/048261 and U.S. Patent Application Publication No. 2014/0356849. In additional embodiments, the platform devices can comprise fluid management devices capable of managing fluid flow into the bio-assessment devices disclosed herein. Such fluid management devices are disclosed in International Patent Application No. PCT/US2015/052043, entitled "DEVICES FOR FLUID MANAGEMENT AND METHODS OF MAKING AND USING THE SAME," filed on Sep. 24, 2015.

The platform devices disclosed herein also can optionally comprise analyzers or sensors capable of detecting properties and the chemical make-up of fluids passed through the platform device, such as effluent exiting a bio-assessment device or perfusate entering a bio-assessment device. In some embodiments, the analyzers or sensors are integrated with the perfusion controller to form one singular component, and in other embodiments they are separate components. In some embodiments, the analyzers, sensors, and perfusion controllers can be used to prevent issues associated with calibration and fouling of in-line electrochemical sensors, to isolate the bio-assessment devices of the platform for seeding, diagnosis, and/or treatment protocols, for inter-bio-assessment device media balancing and shunting, and to provide additional local perfusion or gas exchange. In other examples, the analyzers or sensors are used to determine the functioning of one or more of the bio-assessment devices or the effect of one or more introduced compounds, for example on metabolism, secretion, gene expression, and so on. Analyzers can include one or more of devices or instrumentation for liquid chromatography (for example, high performance liquid chromatography or ultra performance liquid chromatography), mass spectrometry (MS; such as MS-MS, gas chromatography-MS, ion mobility-MS), or a combination thereof. In one example, the analyzer includes instrumentation for ultra performance liquid chromatography-ion mobility-MS.

In some embodiments of the disclosed platform devices, multichannel potentiostats can be used to measure dynamic changes in glucose, lactate, oxygen, and pH in cells and media used in the bio-assessment devices. Embodiments of a multichannel potentiostat that can be used with the disclosed platform devices are described, for example, in U.S. Patent Application Publication No. 2014/0356849.

IV. Methods of Making the Lung Organ Devices

Disclosed herein are embodiments of methods for making the devices disclosed herein. In some embodiments, the methods concern making a lung organ device by combining one or more components disclosed herein. In some embodiments, the methods concern making each individual component that can be included in the lung organ device independently, such as the bronchiole device component and the alveolar device component. Suitable materials for making such components are discussed herein.

Embodiments of the bronchiolar device can be made by making a first substrate comprising one or more inlets, outlets, ports, or a combination thereof and further comprising at least one channel and incubation chamber fluidly coupled to the inlets, outlets, ports, or a combination thereof. The inlets, outlets, and fluid ports of the first substrate can be formed using a laser, as can the channels of the first substrate. In particular disclosed embodiments, one or more tube lines can be attached, such as by using an adhesive, to the inlets and outlets of the first substrate. The tube lines can be attached at any point of making the device. The first substrate can be coupled with a second substrate comprising one or more fluid ports and/or channels that also can be made using a laser cutting technique. The fluid ports of the second substrate can be aligned with the fluid ports and outlets of the first substrate so that one or more fluids can flow there through. The first substrate and the second substrate can be coupled using a suitable adhesive or adhesive tape (single-sided and/or double-sided) known to those of ordinary skill in the art, or they can be laminated together. A tube platform, as discussed herein, can then be placed within the incubation chamber of the first substrate. The hollow tubes of the tube platform can be positioned to align with the channels of the first substrate so the channels and the central lumens of the hollow tubes are fluidly coupled. In some embodiments, an additional substrate can be coupled to the first substrate so as to cover the entire surface area of the first substrate, or at least a portion thereof.

Alternative methods of making the bronchiolar device are also contemplated by the present disclosure. For example, in some embodiments, the bronchiolar device can be made by coupling a first substrate to a second substrate through a third substrate that includes one or more channels fluidly coupled to an incubation chamber. In some embodiments, the second and third substrate can be coupled together using an adhesive, adhesive tape (single-sided and/or double-sided), or lamination technique. One or more hollow tubes can be placed within the one or more channels so that the pores of the hollow tubes are substantially located within the incubation chamber. Tube lines can be connected to each end of the hollow tube and placed within the one or more channels. In some embodiments, a plurality of hollow tubes and tube lines can be positioned as described above and further positioned to be parallel to one another. In some embodiments, one or more inlets and/or outlets can be formed in the top of the first substrate or the inlets and/or outlets can be formed within the third substrate parallel to the one or more channels fluidly coupled to the incubation chamber. Tube lines can be attached to the inlets and outlets using methods known to those of ordinary skill in the art. In some embodiments, a membrane can be placed between the fluid-compatible component and the medium-compatible component.

Figure 76:
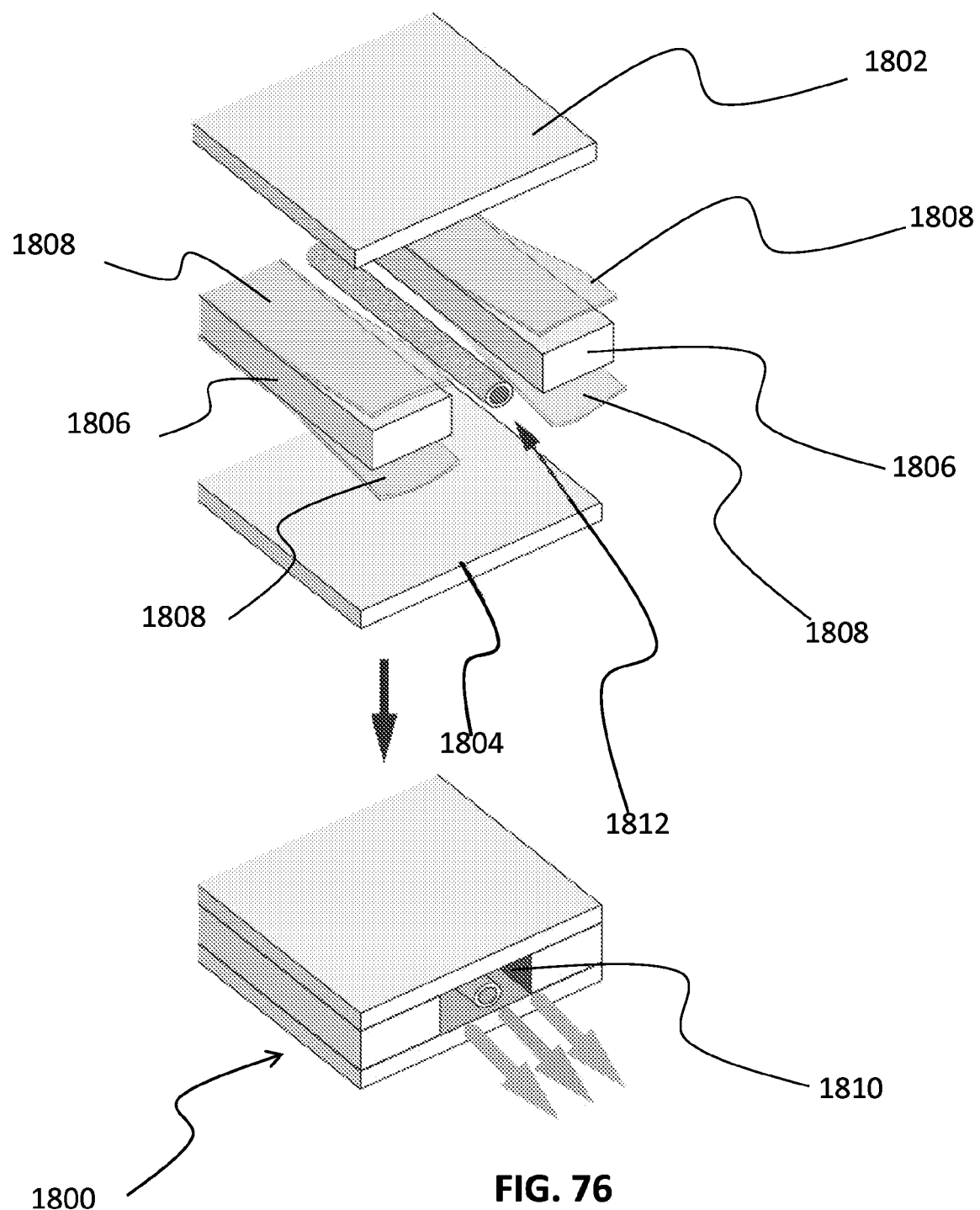
FIG. 76 illustrates an exemplary method of making a bronchiolar device.

In some embodiments, such as the branching bronchiolar device embodiments disclosed herein, a first substrate can be fabricated to include a plurality of channels that branch from junctions. One or more inlets, outlets, and fluid ports also can be cut into the first substrate, typically using a laser. A second substrate can be made in a similar manner. The first and second substrate can be coupled together through a membrane using an adhesive or adhesive tape (single-sided and/or double-sided). In some embodiments, the membrane can be fabricated to include one or more fluid ports that align with the inlets, outlets, and/or fluid ports of the first and/or second substrate. Another exemplary method for making a bronchiolar device is illustrated in FIG. 76. As illustrated in FIG. 76, an exemplary bronchiolar device 1800 can be made by coupling a first substrate 1802 with a second substrate 1804 using multiple segments 1806 that can be positioned between the first substrate 1802 and second substrate 1804 using adhesive component 1808, thereby providing one or more channels 1810 (or incubation chambers). One or more hollow tubes 1812 can be positioned within each channel 1810 (or incubation chamber).

In some embodiments, cells (or compositions comprising cells) can be introduced into the bronchiolar device after it is made using the one or more inlets present in the device. In other embodiments, such as those comprising membranes, the cells can be introduced onto the membrane and then the device can be assembled, or the cells can be introduced after assembly.

Figure 77:
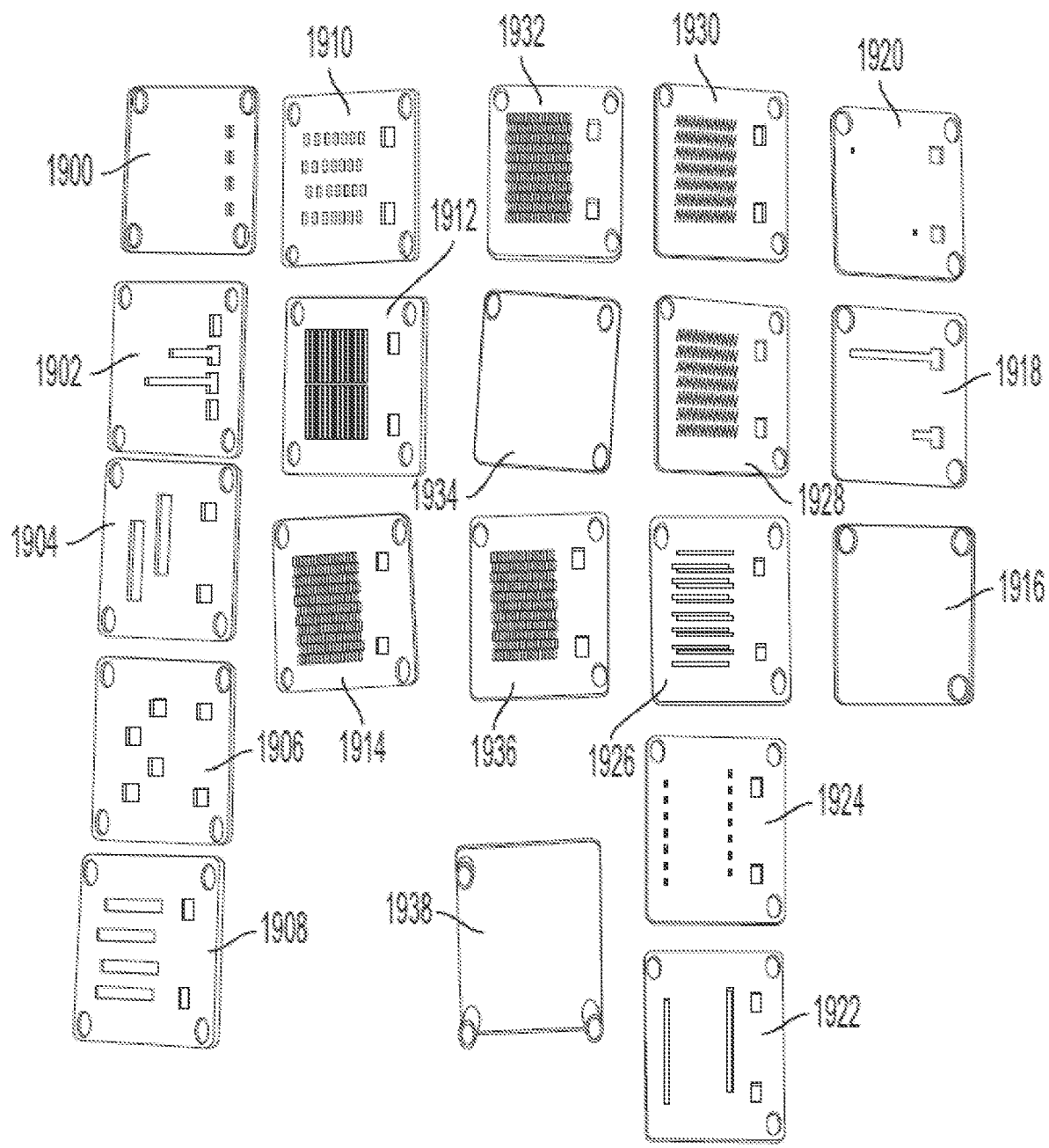
FIG. 77 shows exemplary substrates used to make the fluid-compatible and medium-compatible components of an alveolar device.

In some embodiments, the alveolar devices disclosed herein can be made by coupling a fluid-compatible component, a membrane component, and a medium-compatible component. While exemplary methods of coupling these components are described herein, these components can be coupled in any order. In some embodiments, a plurality of substrates, or at least one substrate, can be coupled to make the fluid-compatible component, which can then be coupled to the membrane component comprising the membrane material, which may or may not be coupled to a medium-compatible component. The medium-compatible component also can be made by coupling a plurality of substrates, or at least one single substrate. In some embodiments, each substrate of the fluid-compatible component and/or the medium-compatible component can be pre-cut with a laser to provide substrates having a suitable number of channels with particular dimensions. Adhesives, adhesive tapes (single-sided and/or double-sided), or lamination techniques known to those of ordinary skill in the art can be used to couple the various independent substrates of the fluid-compatible component together, as well as the various independent substrates of the medium-compatible component. FIG. 77 illustrates an exemplary embodiment illustrating the order in which each substrate can be combined to form the fluid-compatible component and the medium-compatible component. Substrates 1900-1914 can be combined to form an exemplary fluid-compatible component and substrates 1916-1936 can be coupled to form an exemplary medium-compatible component.

An exemplary method of making a fluid-compatible component is illustrated in FIGS. 78A-78H. An exemplary sequence of steps is illustrated in FIGS. 78A-78H; however, any suitable variation in the order of these steps in contemplated by the present disclosure. As illustrated in FIG. 78B, a first substrate can be positioned on an alignment stage. As illustrated in FIGS. 78C and 78D, subsequent substrates can be coupled to the first substrate; the subsequent substrates include an adhesive layer on both sides. The subsequent substrates can be seam rolled (which can occur on or off of the alignment stage) after each substrate is coupled to the previously coupled substrate to facilitate proper coupling (FIG. 78E). A membrane component can be added after the plurality of substrates have been coupled (FIGS. 78F and 78G), followed by coupling of inlet and outlet tubing (illustrated in FIG. 78H), which can be coupled to the inlet and outlet of the first substrate. The substrates of the medium-compatible component can be coupled in a similar manner.

In some embodiments, the alveolar device includes a fluid-compatible component and a medium-compatible component can be made to have a first inlet and first outlet that are arranged parallel to a second inlet and second outlet. Channels extending from the first inlet to the first outlet can be formed within a substrate of the fluid-compatible component and channels extending from the second inlet to the second outlet can be formed within a substrate of the medium-compatible component.

Figure 79:
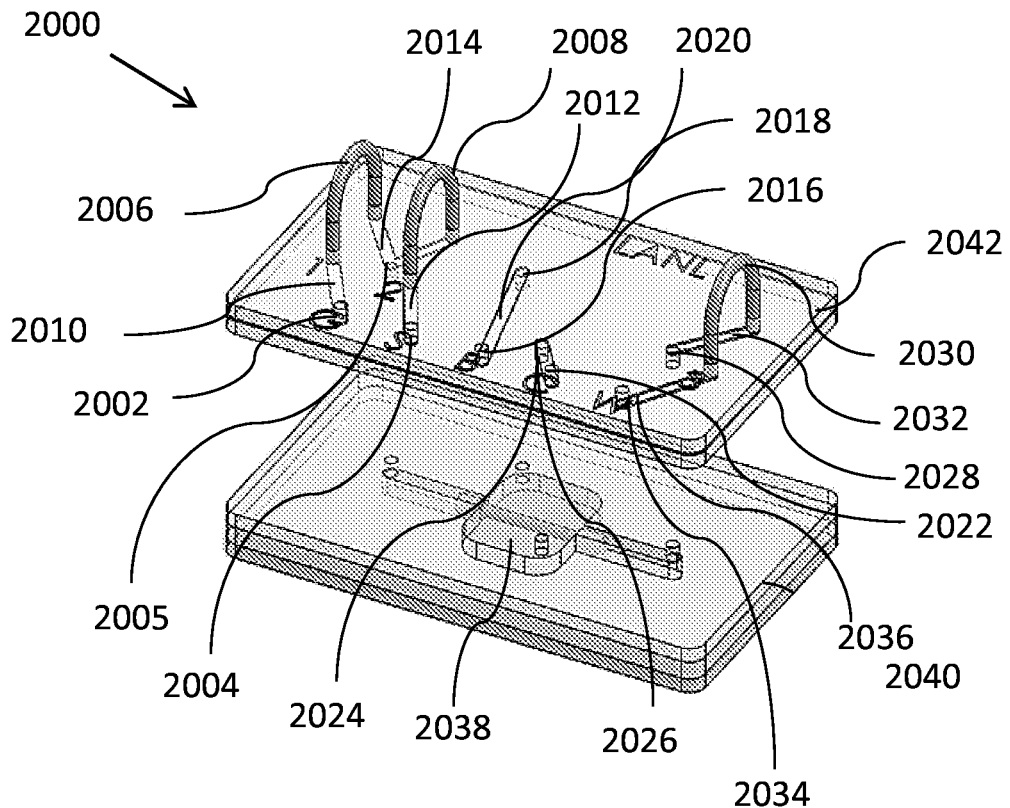
FIG. 79 illustrates an embodiment of a fluid management device that can be used with the lung organ device to control delivery of fluids into and out of the device.
Figure 80:
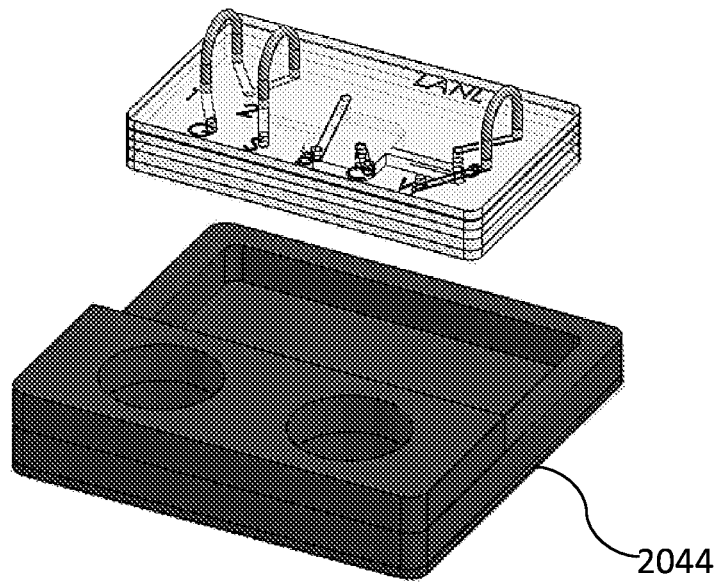
FIG. 80 illustrates an embodiment of a fluid management device connected to a bronchiolar device of the lung organ device and a holding stage that can be used with the device.

In some embodiments, the bronchiolar device can be fluidly coupled to a fluid management device. Embodiments of a fluid management device can be used to manually operate an embodiment of the assembled lung organ device. In some embodiments, operation of the fluid management device can be automated. An embodiment comprising a fluid management device is illustrated in FIGS. 79 and 80. As illustrated in FIG. 79, the fluid management device 2000 can be fabricated as a polymeric substrate 2042 comprising, for example, an inlet 2002 through which a first fluid can be introduced in a bronchiolar device 2040, and a second inlet 2004 through which cells (or a composition thereof) can be introduced into the bronchiolar device. Inlets 2002 and 2004 can be fluidly coupled with channels 2010 and 2012, respectively, which can deliver fluid or cells to tube lines 2006 and 2008, respectively. Tube lines 2006 and 2008 are further fluidly coupled to V-shaped channel 2014, which is fluidly coupled to inlet 2005. Inlet 2005 can deliver the fluid or cells to bronchiolar device 2040. The fluid management device 2000 can further include an inlet 2016 through which a second fluid, such as a biological medium, can be introduced into an incubation chamber 2038 via channel 2020 and fluid port 2018 of bronchiolar device 2040. The second fluid can be delivered from the bronchiolar device 2040 via outlet 2022, which is fluidly coupled to fluid port 2026 via channel 2024. In some embodiments, the fluid management device 2000 includes an outlet 2034 from which the first fluid can be isolated for testing. Outlet 2034 can be fluidly coupled to the bronchiolar device 2040 through channel 2036, which is fluidly coupled to tube 2030, channel 2032, and fluid port 2028. In exemplary embodiments, fluid management device 2000 can be coupled with holder 2044, as illustrated in FIG. 80.

Figure 81:
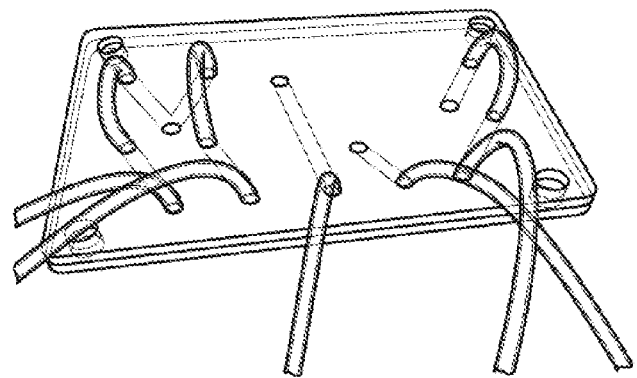
FIG. 81 shows a working example of the fluid management device illustrated in FIG. 79.
Figure 82:
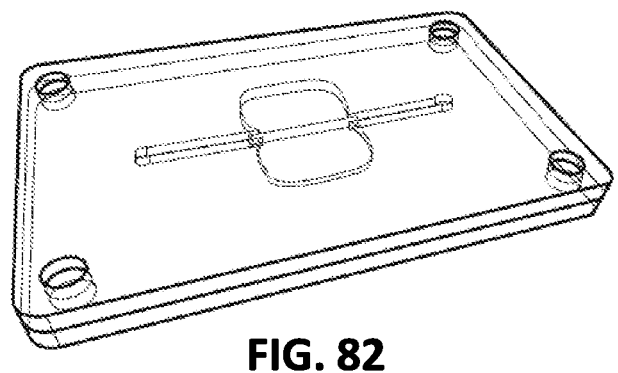
FIG. 82 shows a working example of a bronchiolar device that can be used with the fluid management device shown in FIG. 81.
Figure 83:
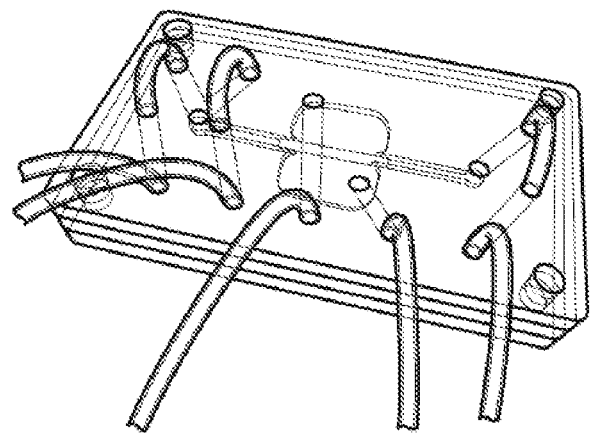
FIG. 83 shows a working example of a fluid management device combined with a bronchiolar device.

While FIG. 79 illustrates an exemplary fluid management device for use with a bronchiolar device, the fluid management devices contemplated by the present disclosure can be modified to include additional ports, inlets, outlets, and/or channels to facilitate use with a bronchiolar device and an alveolar device, as combined to form a lung organ device. An exemplary embodiment of a bronchiolar device comprising a fluid management device is shown in FIGS. 81-83. FIG. 81 shows an exemplary fluid management device and corresponding tubing; FIG. 82 shows an exemplary embodiment of a bronchiolar device that can be fluidly coupled to the fluid management device; and FIG. 83 shows an assembled device with a fluid management device.

V. Methods of Using the Devices

A. Lung Bio-Assessment Devices

In some embodiments, each of the bronchiolar and alveolar device embodiments disclosed herein can be independently used for different applications. For example, the bronchiolar device can serve as a disease model to study bronchiolar disorders such as asthma, chronic obstructive pulmonary disease, cystic fibrosis, respiratory syncytial virus infections, and influenza. The alveolar device, for example, can be used as a disease model to study alveolar targeting diseases such as pneumonia, tuberculosis, lung cancer, cute respiratory distress syndrome, pneumoconiosis and infectious diseases.

Also disclosed herein are embodiments of methods of using the disclosed lung organ devices. Particular method embodiments disclosed herein include introducing a compound (such as a drug, toxin, stimulus, or composition thereof), into a lung organ device embodiment disclosed herein and analyzing a response generated by the lung organ device after the compound has been introduced into the lung organ device. In some embodiments, analyzing a response includes detecting whether a compound causes a change in the way in which the device, or a component thereof, operates. In some embodiments, a control compound is introduced into the device to provide baseline results to be used as a comparison for other compounds of interest that are introduced into the device. Such control compounds could be any compound known to those of ordinary skill in the art to have a known or understood effect on lung activity (e.g., epinephrine, methoxamine, or the like). For example, in some embodiments, the compound can adversely influence or modify one or more of the cell populations associated with various components of the device (e.g., a membrane material, a hollow tube, etc.) so that the cell population produces responses (e.g., immune responses, physical leakage of fluids between a membrane layer or a hollow tube, changes in gene expression, secretion of molecules, cell death or apoptosis, cellular edema, inhibition of gas exchange, or a combination thereof) that can be detected using a suitable detection technique, such as immunohistochemical staining, trans-epithelial electric resistance (TEER) measurements, visual detection, mass spectrometric detection, chromatographic detection or the like.

In some embodiments, a first compound may be administered that has any of the above-mentioned adverse effects on one or more components of the device and then a second compound, such as a therapeutic compound (or potentially therapeutic compound) capable of ameliorating, inhibiting, or stopping the adverse effects, can be administered. The ability of the second compound to ameliorate or stop the adverse effects can then be determined by analyzing a sample extracted from the device and determining whether, for example, leakage has been stopped or reduced or if immune responses from the cell populations have stopped or diminished.

In some embodiments, the disclosed lung organ devices can be used to create a stable and reproducible air-liquid two-phase culture environment for long term lung tissue culture and growth. The disclosed devices also can be used to monitor lung function, metabolism, and secretion. In some embodiments, the devices can be used in combination with biological assays known to those of ordinary skill in the art to be suitable for determining lung function, metabolism, and/or secretion. For example, the disclosed devices can be used in combination with assays suitable for analyzing fluids or other samples that pass through the lung organ device and are affected or modified by the cell populations present in the bronchiolar and alveolar devices of the lung organ device. In additional embodiments, the devices can be used to obtain physiological measurements of cyclic alveolar stretching, $O_2$ and $CO_2$ gas exchange efficiency, mucus clearance efficiency, monitoring pH of a biological medium, immune function (e.g., cytokine profile, creatine kinase release, CPY450 enzyme profiles), or a combination thereof. The devices also can be used to test for inflammatory response to LPS challenge that decreases forced expiratory volume (FEV1), induces severe inflammatory responses (enhanced IL-1, IL-6, IL-8, TNF-α), and recruits immune cells to an infection site.

In some embodiments, the lung organ devices disclosed herein (or components thereof) can be used in combination with one or more disease models and/or can be used to produce disease models. For example, the bronchiolar device can be used to grow cell populations that produce mucin; therefore, the lung organ device can be used to produce a disease model that can simulate increases in mucin (for example, as in cystic fibrosis) and the effects of this increase. The ability to control mucin production with certain drugs can therefore be studied with the disclosed lung organ devices. In other embodiments, the lung organ device can be used to test the effects of various biologically active compounds and/or biomolecules on cell growth and/or differentiation. In some embodiments, manipulation of cell culture conditions, including addition of specific compounds or biomolecules, targeted design of media and using specific extracellular matrix (ECM) proteins, can cause changes in the differentiation of lung cells and the functional characteristics of the lung cells. Different coating materials (e.g., biomolecules—such as laminin, fibronectin, collagen) either alone or at different ratios to simulate the ECM on either an bronchiolar device or an alveolar device can be used to manipulate cell differentiation and allow the development of different model diseases. For example, different ECM coating can induce or reduce cilia formation. A reduction of cilia formation can cause poor clearance of mucus from bronchi and lead to the induction of cystic fibrotic lung. In some embodiments, enhanced mucin secretion or differentiation of cells to mucin producing cells could cause a mucotic disease model. Such disease models can be evaluated using targeted cilia and mucin staining, imaging, cilia movement recordation, immune assays, TEER measurements, gas exchange monitoring, or a combination thereof.

The lung organ devices disclosed herein can be further combined with one or more analytical devices capable of analyzing samples obtained from the lung organ device. Such devices can be used to analyze a response generated by the lung organ device. For example, devices like chromatographs (gas or liquid), mass spectrometers, or a combination thereof can be used to analyze fluids that are extracted from the lung organ device to detect or determine the presence of drugs, toxins, or other chemical components present in the fluids. In some embodiments, fluids may be extracted from the device using an automated system. The analytical devices can be integrated with or separate from the lung organ device, or a component thereof.

In some embodiments, the lung organ devices disclosed herein can be coupled to one or more additional organ mimetic systems, such as heart devices, liver devices, kidney devices, or the like. In such embodiments, the lung organ devices can be fluidly coupled to the one or more additional organ mimetic systems. For example, fluids that are delivered to or from the lung organ device may be delivered to and from one or more organ mimetic systems through a hollow tube (or plurality of hollow tubes) connecting such devices. In yet additional embodiments, the lung organ device can be fluidly coupled to one or more additional bio-assessment devices through the platform device embodiments disclosed herein. Solely by way of example, an inlet of a lung organ device, such as an inlet of a bronchiolar device, can be directly or indirectly (e.g., through a fluid management device) fluidly coupled to a ventilator via a connecting tube. An outlet of a lung organ device, such as an outlet of a bronchiolar device or an outlet of an alveolar device, can be directly or indirectly (e.g., through a fluid management device) fluidly coupled to a heart device or a combination of heart devices (e.g., a left heart device and a right heard device).

In some embodiments, the disclosed lung organ devices can be used for real-time monitoring of lung function, metabolism, and secretion using assays, such as assays to determine anatomical and biochemical immunohistochemistry for occludin (epithelium), cadherin (endothelium), alcian blue (mucin secreting cells), tubulin (ciliated cells), ICAM-1, IL-1β, IL2, IL6, IL10 (inflammatory markers), E- and P-selectin (endothelial barrier), and H&E staining, mucin secretion, surfactant release, and combinations thereof.

B. Platform Devices

The disclosed platform devices can be used to analyze the response of one or more tissues, organ constructs, or bio-assessment devices (such as 2 or more, 3 or more, 4 or more, such as a multi-organ construct or multi-organ system) to one or more agents, such as chemical or biological agents (referred to in some examples as test compounds or agents), including but not limited to drugs or drug candidates (e.g., pharmacological agents), toxins, infectious agents (such as bacteria, viruses, parasites, or fungi), nutritional supplements, nutraceuticals, and/or cosmetic products. Thus, in some examples, the methods disclosed herein are useful for toxicity testing, pharmacodynamics/pharmacokinetic testing, and/or efficacy testing of various agents. In particular examples, the disclosed methods can supplement or even replace in vivo testing of agents, for example in animal models, thus, decreasing drug development time. In particular, since the disclosed devices utilize human cells and their arrangement in organs and/or multi-organ systems, the methods can provide more data that are more physiologically relevant to humans than animal model systems.

In particular embodiments, fluid (such as a universal medium) is circulated through the platform devices disclosed herein. The fluid includes components that support the viability and function of the bio-assessment device(s) in the platform device, including components such as inorganic salts and/or minerals, amino acids, energy-providing components, vitamins and/or cofactors, supplements, trace elements, organic acids, salts, and/or esters, antibiotics, and/or protein growth factors. In some examples, the fluid includes those disclosed in International Patent Application No. PCT/

US2015/052046, entitled MULTI-ORGAN MEDIA COMPOSITIONS AND METHODS OF THEIR USE, filed on Sep. 24, 2015, which is incorporated herein by reference.

In some embodiments, the methods include introducing one or more agents or substances to platform device disclosed herein and measuring one or more effects of the agent(s) or substance(s) at the system level, organ level, and/or cellular level. In some examples, the effects include molecular and biochemical effects, such as changes in gene expression/biomarkers (for example, presence and/or amount of proteins, nucleic acids (such as RNA or cDNA), or metabolic products), production and/or secretion of cellular products (such as enzymes, host defense molecules, surfactants, signaling molecules), or cell-cell interactions. In other examples, the effects include pharmacological or toxicological responses, such as drug metabolism (e.g., absorption, bioavailability, half-life, metabolism, tissue distribution, and/or clearance), changes in drug metabolism pathways (e.g., changes in metabolic and elimination pathways, such as cytochrome P450), or toxicity (such as cell death). In additional examples, the effects include physiological function of one or more tissues or organs. Organ-specific physiological functions may include production of enzymes, proteins, lipids, and/or xenosensors (liver); vesicle formation and cycling, beating cilia, and/or immunological/inflammatory functions (lung); glomerular filtration, urine production, concentration, or content, and/or renin release (kidney); beating rate or force of contractility, arrhythmia, and/or electrophysiology or action potentials (heart). Test compounds or agents may have one or more effects and their effects may overlap molecular/biochemical, pharmacological/toxicological, and physiological categories and/or may have effects on more than one organ construct. For example, test compounds or agents may have effects in one or more categories. Test compounds or agents may also have one or more effects in more than one organ construct. Furthermore, a particular effect of a test compounds or agents may be classified in more than one category. One of ordinary skill in the art can identify additional categories and/or effects that may be relevant to any particular test compound or agent.

In some embodiments, drugs and/or toxins disclosed herein can be tested to determine the anatomical and functional integrity of the bio-assessment device(s) used in the platform device, such as the lung organ device. The platform device's pathophysiological fidelity also can be evaluated. Measurable indicators or biomarkers that are often predictive of functional consequences are used to assess the physiological state of the organ device. Moreover, multiple events will be probed at the organ, tissue, cellular and molecular level, enabling a comprehensive assessment of response. In some embodiments, a combination of on- and off-line methods can be used to monitor the bio-assessment device's physiological and biochemical signature responses. For example, the percent cell viability at different time points can be assessed and assigned to monitor tissue maturation and lifespan.

The anatomical and functional integrity of a bio-assessment device (or another device used with the platform device) is assessed by morphological (anatomical), physiological (e.g., glomerular filtration rate, or "GER," vesicle formation, heart rate, etc.), metabolic characterization and molecular-level benchmark responses specific for each organ. In some embodiments, custom-designed, organ-specific gene array platforms (96 genes×96 conditions—HTP FLUIDIGM®) comprised of genes down-selected to represent a healthy and diseased tissue (gene profile in response to insult agent) are used for high through-put analysis of tissue/organ development, maturation and metabolic state. Embodiments of the array can also include genes that are more representative of a generalized toxicological response to realize the predictive aspects of the platform device and/or the bio-assessment device(s). In some embodiments, drug compounds with extensive human/animal exposure data can be used, such as FDA-approved toxic/non-toxic compounds, chemical threat agents, and pathogens. The well-known/measurable physiological responses and biomarker profiles of the drugs/toxins on human organs can then be used for comparison with the results obtained from using the disclosed platform devices and devices. Some compounds used herein are toxic to more than one organ, while others are efficacious in one and toxic to the other. Such compounds also can be used in the methods described herein. In exemplary embodiments, a threat agent-specific mini-chromosome maintenance protein inhibitor, e.g., ciprofloxacin after biological assessment exposure, can be used. To establish a predictive model of drug metabolism, the flow rate is maintained at rate that is sufficiently high to recapitulate nutrient/waste exchange as in the corresponding in vivo vasculature, but at the same time provide sufficient drug/media residence time in the perfused organ device, such as the lung organ device, to ensure a measurable drug metabolic response. A computational biology model can be used to evaluate the results. In some embodiments, doses and exposure times can be determined based upon literature data and/or the output from trial embodiments. For screening of non-linear responses, a plurality of concentrations, such as at least three concentrations, for each drug/chemical or can be used. In other embodiments, multiplicity of infection (MOI) analysis can be used for pathogens that are analyzed.

In some embodiments, the component to be analyzed (e.g., drug, toxin, pathogen, or the like) is introduced into the platform device or directly into one bio-assessment device. In some embodiments, the component to be analyzed is introduced into a platform device embodiment using a microformulator and is introduced in a manner that enables determination of both the dose-response and dose-timing associated with each observed effect. In other embodiments, the component to be analyzed is introduced into a particular bio-assessment device via an inlet of the bio-assessment device directly or via a fluid management device. In some embodiments, the responses can be validated by correlation to corresponding human/animal pharmacokinetics (e.g., half-lives, tissue retention, distribution and clearance) and established signature responses. High fidelity validation endpoints that are sensitive, robust and generalizable to organ toxicity for the lung organ device (or other device of the platform device) are determined, thus enabling predictive studies. In some embodiments, labeled drugs and chemical threat agents can be used to facilitate the ability to easily track their flow through and interactions with the lung organ device (or other devices in the platform device). For example, isotopic or fluorescent labeling of compounds enables rapid monitoring of the relative pharmacodynamics/pharmacokinetic efficiency of the bio-assessment device or of biochemical pathways.

In some embodiments, the platform devices disclosed herein can be used in combination with different detection methods to understand and validate the ability of the constructs and devices to respond to drugs and toxins. In particular embodiments, the platform devices and lung organ devices can be used in combination with ion mobility-mass spectrometry (IM-MS), which provides significant advantages over alternative MS strategies for complex biological studies by allowing the intricate characterization of the complex biomolecular profile through its unique modes of separation. In some embodiments, IM-MS first separates analytes, in the form of gas-phase ions, according to their orientationally averaged collision cross section with a neutral gas, which when performed under appropriate conditions correlates with molecular surface area. These separations can, in some embodiments, be analogous to gas-phase electrophoresis but in the gas-phase the timescale for separation is μseconds to mseconds, or nearly five orders of magnitude faster than condensed-phase separations of LC. Following IM separation, the ions are characterized by their mass using high speed MS analysis.

In some embodiments, ultra performance liquid chromatography (UPLC) can be used to quantify and/or identify compounds present in media used in the lung organ device and/or platform device. In some embodiments, UPLC can be used alone or in combination with the IM-MS techniques discussed above. In embodiments where UPLC and IM-MS are used together, they typically are operated in a multiplexed fashion to retain the temporal resolution of the microfluidics. Solely by way of example, a single 5 minute UPLC run can be duplexed to increase temporal resolution to less than 3 minutes with no sample loss (e.g., column 1 separates while column 2 is loaded). The microfluidic-UPLC-IM-MS platform can be used for online analysis, but with a delay of approximately 5 minutes between sample draw and data output. Such online techniques can be used to evaluate and/or monitor events at multiple points in the fluid path of a platform device nearly simultaneously.

Figure 97:
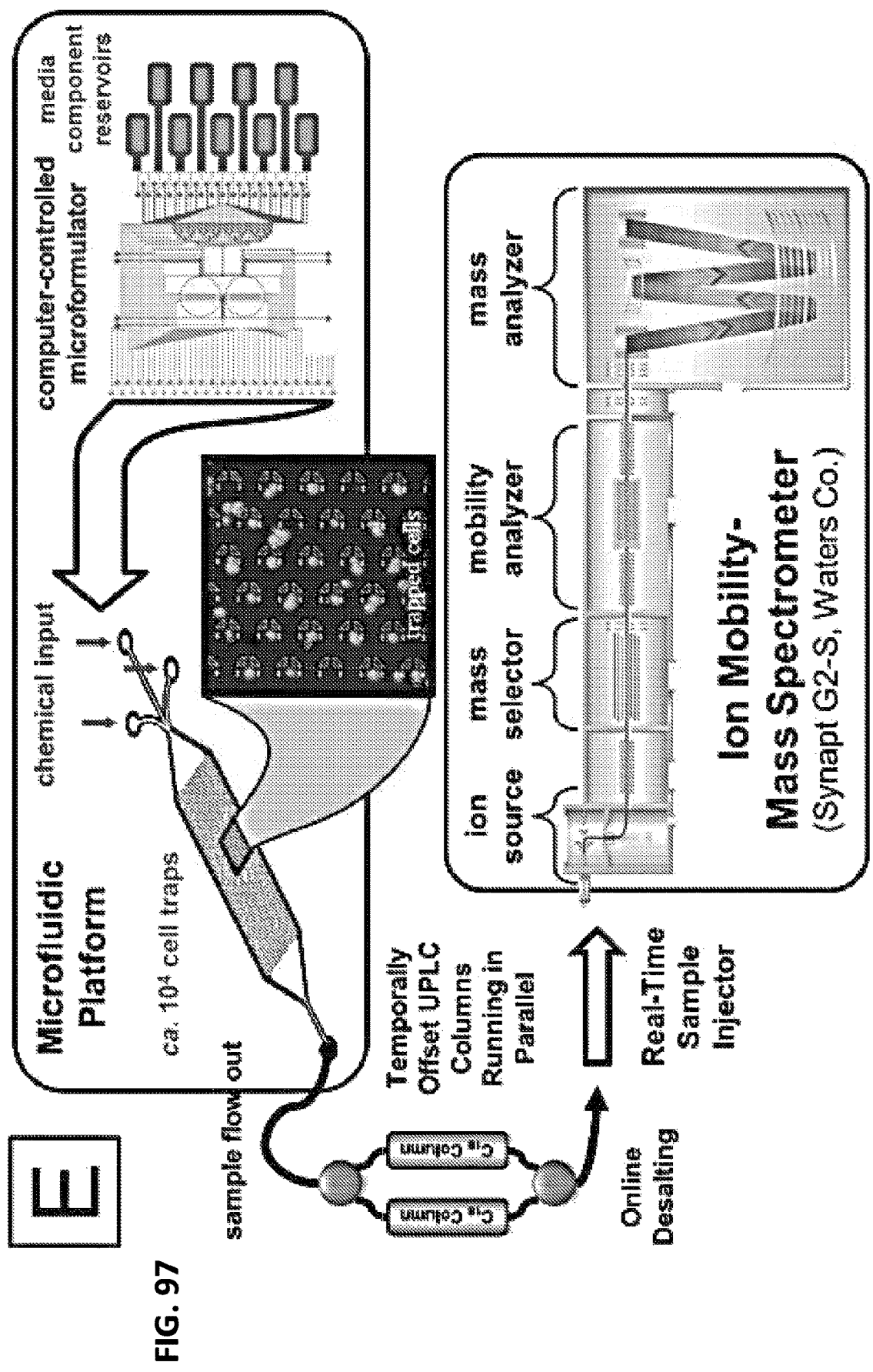
FIG. 97 illustrates a representative embodiment of a sampling configuration wherein an ion-mobility mass spectrometer is coupled to an online ultra performance liquid chromatograph, which accepts a sample from a fluidic platform device, which simply represents a bio-assessment device as disclosed herein.

FIG. 97 illustrates a flow diagram of a microfluidic-coupled LC-IM-MS embodiment. Solely by way of example and with reference to FIG. 97, viable cells stored and maintained in a microfluidic device (which can correspond to one or more of the bio-assessment devices disclosed herein) can be perfused with a custom cocktail of chemicals from a microformulator. Resulting cellular excretions are then directed to a multiplexed UPLC setup, where salts are removed and the sample is directed online to the IM-MS. The IM-MS acquires simultaneous IM-MS and tandem IM-MS/MS data. Data are processed by multivariable statistical analysis to identify, quantify, and validate significant metabolic signatures.

Compounds or agents that may be used in the methods described herein include chemical or biological agents (referred to in some examples as test compounds or agents), including but not limited to drugs or drug candidates (e.g., pharmacological agents), toxins, infectious agents (such as bacteria, viruses, parasites, or fungi), nutritional supplements, nutraceuticals, and/or cosmetic products. In some examples, as discussed above, one or more compounds or agents are tested simultaneously or sequentially, such as a toxin and a countertoxin or candidate countertoxin.

Exemplary infectious agents that may be used in the disclosed methods (for example to assess the effects of an infectious agent or to screen for or test safety or efficacy of candidate treatments) include bacteria, such as *Francisella tularensis, Burkholderia* spp. (for example, *B. mallei, B. pseudomallei*), *Brucella* spp. (for example, *B. melitensis, B. abortus, B. suis*), *Yersina pestis, Bacillus anthracis, Mycobacterium tuberculosis, Legionella* spp. (for example, *L. pneumophila*), *Neisseria meningitidis, Streptococcus pneumoniae, Mycoplasma pneumoniae, Haemophilus influenzae* type B, or drug-resistant bacteria (such as drug-resistant *Staphylococcus aureus*, drug-resistant *Streptococcus pneumoniae*, for example, methicillin-resistant *Staphylococcus aureus*). Infectious agents that may be used in the disclosed methods also include viruses, such as influenza virus, hepatitis virus (such as hepatitis A, hepatitis B, or hepatitis C), human immunodeficiency virus, respiratory syncytial virus, polyoma virus, cytomegalovirus, human papilloma virus, flavivirus (for example, Dengue virus, West Nile virus, St. Louis encephalitis virus, Japanese encephalitis virus, tick-borne encephalitis virus), togavirus (for example, rubella, Western equine encephalitis, Eastern equine encephalitis, Venezuelan equine encephalitis virus), filoviruses (for example, Ebola virus, Marburg virus), enteroviruses, poliovirus, and smallpox virus. In other examples, infectious agents that may be used in the disclosed methods include fungi (such as *Candida, Aspergillus, Blastomyces, Coccidioides, Cryptococcus, Histoplasma, Pneumocystis, Sporothrix, Exserohilum*) or parasites (such as *Plasmodium, Trypanosoma, Toxoplasma, Leishmania, Cryptosporidium, Giardia, Trichinella*). One of ordinary skill in the art can identify other infectious agents that can be used with the methods and devices disclosed herein.

In some examples, the disclosed methods include testing of chemical agents (such as chemical warfare agents), for example, to assess the effects of a chemical agent or to screen for or test safety or efficacy of candidate treatments (such as medical countermeasures, MCMs). Exemplary chemical agents include tear agents (for example, a-chlorotoluene, benzyl bromide, bromoacetone, bromobenzylcyanide, capsaicin, chloracetophenone, chloromethyl chloroformate, dibenzoxazepine (CR), ethyl iodoacetate, orthochlorobenzylidene malonitrile, trichloromethyl chloroformate, xylyl bromide), vomiting agents (adamsite, diphenylchloroarsine, diphenylcyanoarsine), or malodorants. Chemical agents also include psychological agents (for example, 3-quinuclidinyl benzilate, phencyclidine, lysergic acid diethylamide), nitrogen mustards (such as bis(2-chloroethyl)ethylamine, bis(2-chloroethyl)methylamine, tris(2-chloroethyl)amine), sulfur mustards (for example, 1,2-bis(2-chloroethylthio) ethane, 1,3-bis(2-chloroethylthio)-n-propane, 1,3-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether, bis(2-chloroethylthioethyl) ether), arsenicals (such as ethyldichloroarsine, methyldichloroarsine, phenyldichloroarsine, 2-chlorovinyldichloroarsine), phosgene oxime, cyanogen chloride, hydrogen cyanide, arsine, chlorine, chloropicrin, diphosgene, phosgene. Additional exemplary chemical agents also include nerve agents, for example, sarin, soman, tabun, cyclosarin, Novicok agents, GV, VE, VG, VM, VX, saxitoxin). One of ordinary skill in the art can identify additional chemical agents that could be used with the devices and methods disclosed herein.

In additional examples, the disclosed methods include testing of toxins (which may include chemical agents discussed above), for example, to assess the effects of a toxin or to screen for or to test safety or efficacy of candidate treatments. Toxins include biological toxins (toxins of biological origin) as well as environmental toxins, such as industrial pollutants or synthetic toxic substances. Exemplary toxins include but are not limited to ricin, botulinum toxin, tetrodotoxin, chlorotoxin, conotoxin, tetanus toxin, bungarotoxin, dendrotoxin, batrachotoxin, curare, pertussis toxin, diphtheria toxin, crotamine, or other reptile or insect venoms. Additional exemplary toxins include pesticides (such as organophosphates, carbamates, organochlorines, neonicotinoids, or pyrethroids), herbicides (such as glyphosate, atrazine, 2,4-D, dicamba, trifluralin, pendimethalin, metolachlor), heavy metals (such as lead, mercury, chromium, cadmium, arsenic), volatile organic compounds (such as benzene, formaldehyde, toluene, perchlroethylene), asbestos, bis-phenol A, and polychlorinated biphenyls (PCBs). One of ordinary skill in the art can identify additional toxins that could be used with the devices and methods disclosed herein.

Exemplary compounds or agents also include, but are not limited to, peptides, such as soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), small organic or inorganic molecules (such as, so-called natural products or members of chemical combinatorial libraries), molecular complexes (such as protein complexes), or nucleic acids (such as antisense compounds, for example, shRNA, siRNA, sgRNA).

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds. Exemplary libraries are available from the NIH Molecular Libraries Program (Molecular Libraries Small Molecule Repository), the NIH Developmental Therapeutics Program compound sets, GlaxoSmithKline, Sigma-Aldrich, Microsource Discovery Systems, ChemBridge, SelleckChem, DNA2.0, AbCheck, GenScript, Thermo Fisher Scientific, GE Dharmacon, Cellecta, Charles River, Phoenix Pharmaceuticals, the EPA ToxCast™ library, and the World Toxin Bank. One of ordinary skill in the art can identify suitable compounds and/or libraries for use in the methods disclosed herein.

V. Examples

Example 1

In some embodiments, microporous polyethersulphone hollow tubes (pore size 10 kD or ~0.3 μm; lumen size 1 mm) are used to create biologically relevant architectures of an in vivo bronchial airway system. Some embodiments of the bronchiolar device have five hollow fibers encased in a PDMS channel manifold that is perfused on the outside with a biological medium, such as a blood surrogate. During establishment of the pulmonary endothelium, media containing bronchiolar epithelial cells and endothelial cells is circulated through the hollow tube central lumens and the extracapillary space (e.g., the space between the outer perimeter of the incubation chamber and the exterior of the elongated bodies of the hollow tubes, respectively. After cell attachment in the central lumen, the cell medium that passes through the hollow tubes is replaced with humidified air to form an air-liquid interface environment allowing for differentiation of cells to form a 3-dimensional lung tissue. Hollow tubes with appropriate pore diameters allow immune cells to be introduced into either the vascular or airway spaces from either side of the hollow tube and simulate bronchial immune function.

In some examples, a membrane (or membranes) is suspended and bonded on ~400 μm diameter apertures on a 10 μm thick polyester membrane substrate, with each planar sheet supporting 768 alveoli. Alveolar epithelial cells are inoculated on the airway side of the membrane component prior to system assembly. A stack of six PDMS substrates are bonded to the airway side of the membrane component. Stacked PDMS substrates with increased thickness are connected with increased weight of inter-connected channels to allow ventilation of the alveolar surface using two reciprocating air pumps, one for the "blue" alveoli (e.g., alveoli simulating inhalation of $O_2$) and one for the "red" alveoli (e.g., alveoli simulating exhalation of $CO_2$) (FIGS. 63 and 64), with out-of-phase red-blue breathing to eliminate cyclic changes in pulmonary blood-surrogate volume. The resulting cyclic bubble-like alveolar expansion can increase membrane surface area and simulate mechanical stretching. The vascular side of the membrane component is overlaid with a bonded stack of PDMS substrates that produces a set of interconnected flow-through microchannels of growing dimensions, enabling uniform pressure and shear on the membrane material. The vascular side of the membrane material is seeded with pulmonary microvascular cells, which adhere to both the membrane material and the channel walls, and fluid shear forces will maintain cell polarization. After alveolar cells are coupled to the membrane component, the PDMS substrates for conducting air can be replaced with new substrates to remove the alveolar cells attached on the PDMS substrates to eliminate the biological responses produced by these cells.

The reconstructed bronchiolar device and alveolar device are integrated together to form lung organ system with relevant physiological functions to a native lung. In some embodiments, each bronchial hollow tube will connect with an alveolar unit; thus, five alveolar units connected with five bronchiolar hollow tubes can provide a total of 3840 alveoli and ~500 $mm^2$ surface area.

Coupling the hollow tubes with co-cultured primary normal human bronchial epithelial (NHBE) cells and human lung microvascular endothelial (HLMVE) with the membrane material supporting human alveolar cells and HLMVEs in the same universal surrogate demonstrates the possibility to perform long term tissue culture in one platform.

Example 2

Figure 84A:
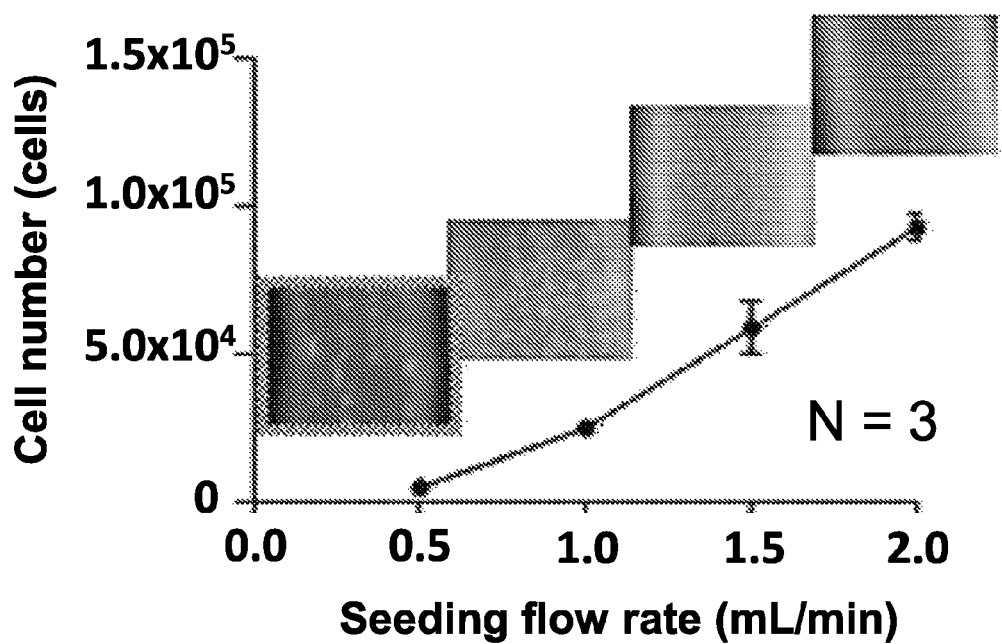
FIGS. 84A-84G show images and data obtained from growing an exemplary cell population within the central lumen of a hollow tube embodiment.
Figure 84B:
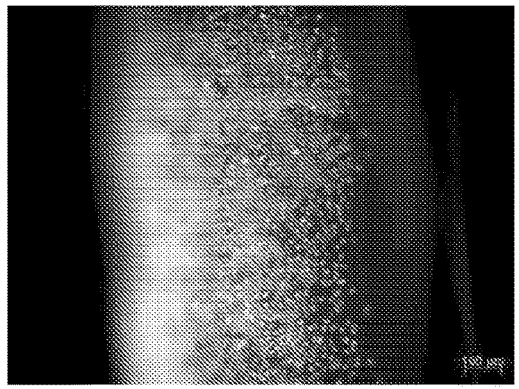
Figure 84C:
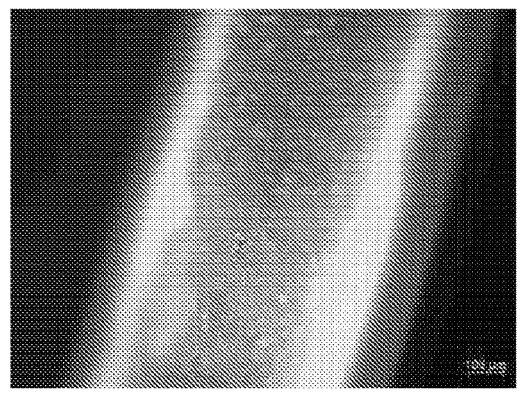
Figure 84D:
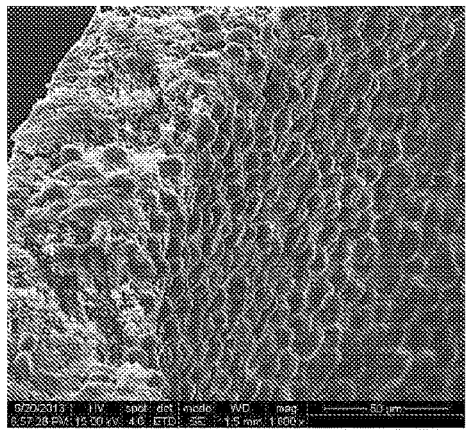
Figure 84E:
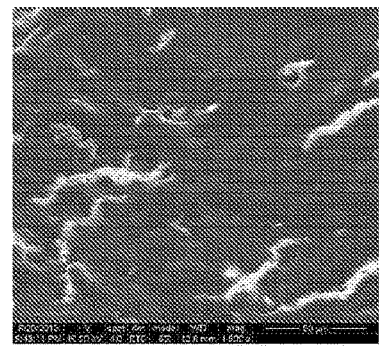
Figure 84F:
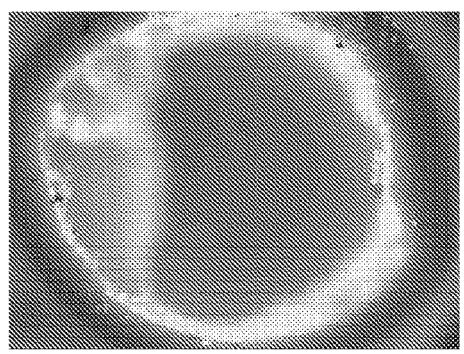
Figure 84G:
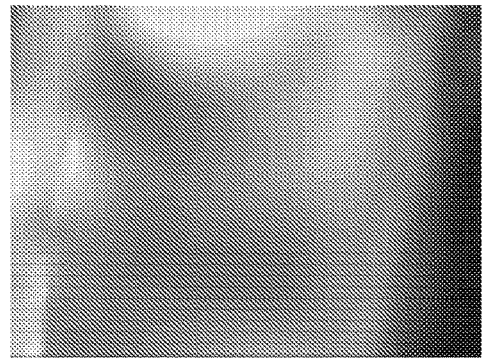

Cells can be seeded on hollow fibers and cultured for a period of time (e.g., 30 days) to produce endothelium tissue and/or epithelium tissue, which can then be adhered to the exterior of the elongated body and/or the interior of the central lumen, respectively. In an exemplary embodiment, human alveolar basal epithelial cells (A549) cells were seeded in the lumen of the hollow fibers using a seeding density of $5\times10^5$ cells/mL and a flow rate of 1 mL/minute for 30 seconds. The hollow fibers were made up of mixed cellulose ester with 0.6 mm of inner diameter and 1 mm of outer diameter. The pore size of the hollow fibers was 0.2

μm. FIG. 84A illustrates a graph of seeding flow rate versus cell number, which provides graphical and pictorial results obtained from a particular embodiment. Additional images from the cultured cells are illustrated in FIGS. 84B-84G.

Example 3

The ability of hollow tubes to facilitate fluid exchange between an air-liquid interface was tested by determine the ability of a liquid to pass from the central lumen of the hollow tubes into a liquid present on the outside of the hollow tube. In one example, a red dye was passed through the central lumen of a hollow tube comprising a plurality of pores and water was allowed to flow over the exterior of the hollow tube. As illustrated in FIG. 85, the red dye was able to pass through the pores into the water. In another example, an air-liquid interface was tested by passing air through the central lumen of a hollow tube and passing a red dye over the exterior of the hollow tube. As illustrated in FIG. 86, bubbles formed on the exterior of the hollow tube, thus corroborating the ability of the air to pass through the pores of the hollow tube. The hollow tubes used in these examples were made of mixed cellulose ester with 0.6 mm of inner diameter and 1 mm of outer diameter. The red dye fluid surrounded by hollow fiber flow had a constant flow of 5 μL/min. The high flow rate of airflow of 1 mL/min was injected constantly into the hollow fiber to build-up internal pressure and allow for the bubbles generated on the exterior of the hollow tube.

Example 4

The ability to grow cells on the surface of a central lumen of a hollow tube was established. Live and dead staining was used to show that human lung adenocarcinoma epithelial cells (A549 cells) could be grown in the central lumen of a hollow tube made using materials disclosed herein, as illustrated in FIGS. 87A-87D (as compared with FIG. 87E, which illustrates the central lumen prior to culture). The hollow fibers were made up of mixed cellulose ester with 0.6 mm of inner diameter and 1 mm of outer diameter. The seeding procedure was used with cell density of $5 \times 10^5$ cells/mL and a flow rate of 1 mL/minute for 30 seconds.

Example 5

Figure 88:
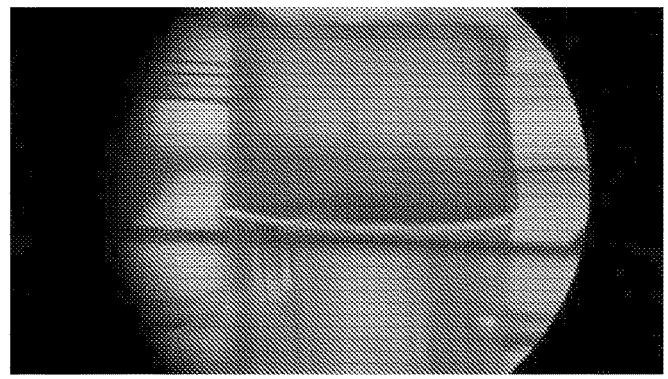
FIG. 88 shows a membrane component of an alveolar device after air has been introduced into the device.
Figure 89A:
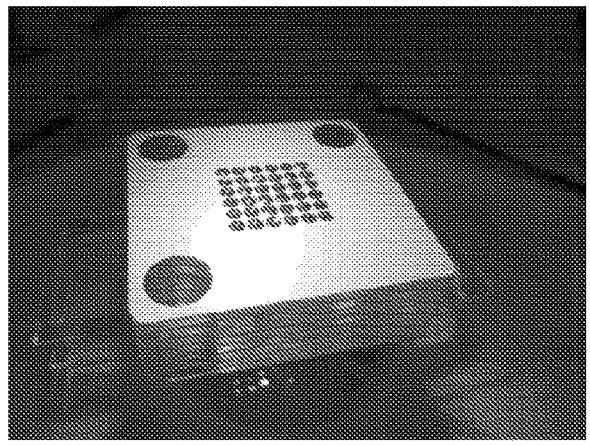
FIGS. 89A and 89B show a portion of alveolar device (FIG. 89A) and the plurality of apertures provided within the device as dual inflation occurs (FIG. 89B).
Figure 89B:
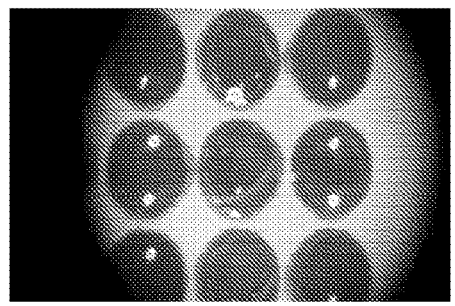
Figure 90A:
FIGS. 90A and 90B show an embodiment of a membrane component of an alveolar device in a resting state (FIG. 90A) and as it is inflated (FIG. 90B).
Figure 90B:
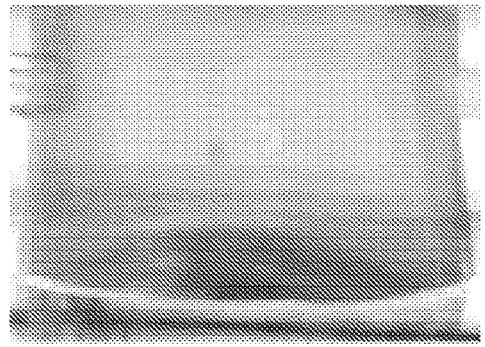

The ability of the membrane component of an alveolar device embodiment to resiliently deform (e.g., expand) and reform (e.g., contract back to its resting state) upon exposure to air was tested. In this embodiment, air pumps were used to inflate (mimicking inhalation) a membrane made from a PDMS-containing material through apertures of an alveolar device, such as that illustrated in FIGS. 63 and 64 (comprising 28×28 wells), for 4 seconds and to deflate (mimicking exhalation) the membrane material for 6 seconds (FIG. 88). The membranes also were tested using dual inflation in an alveolar device comprising 6×6 wells (FIGS. 89A and 89B). In other examples, pumping with 10 cycles per minute (three seconds ON and three seconds OFF) for 12 hours was used. In yet other embodiments, a breathing pattern using 12 cycles per minute (2 seconds ON and 3 seconds OFF) was used (FIGS. 90A and 90B).

Figure 91:
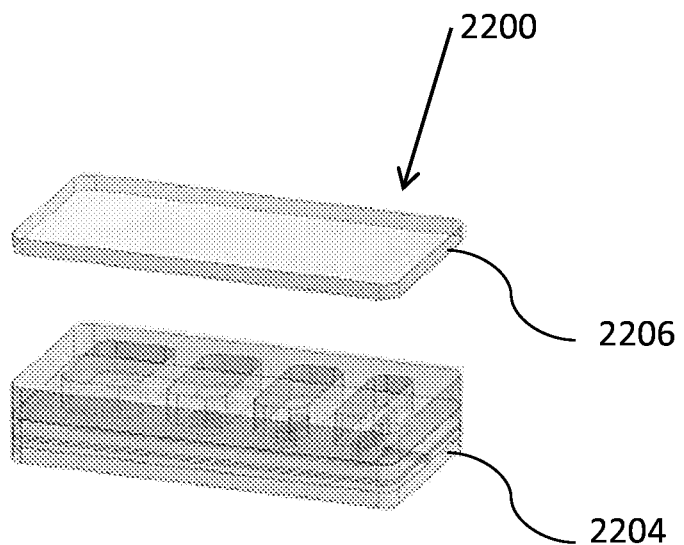
FIG. 91 illustrates an embodiment of an alveolar test device.
Figure 92:
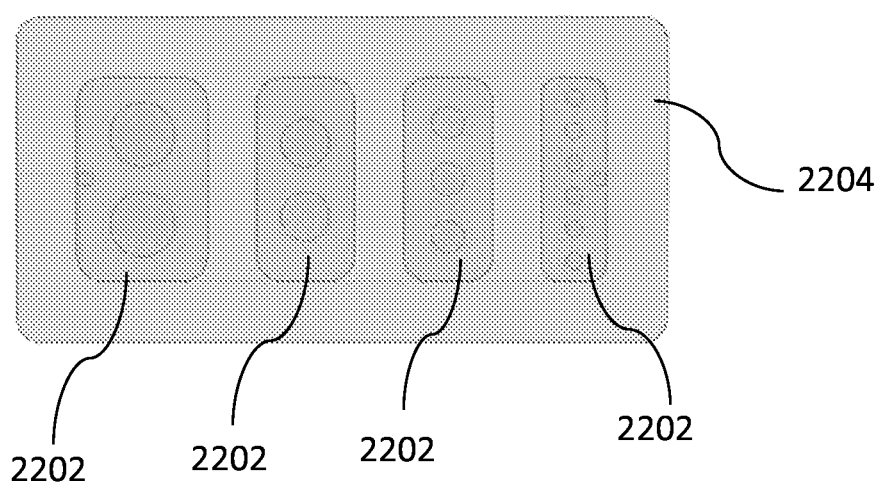
FIG. 92 illustrates a top view of the alveolar test device illustrated in FIG. 86.
Figure 93A:
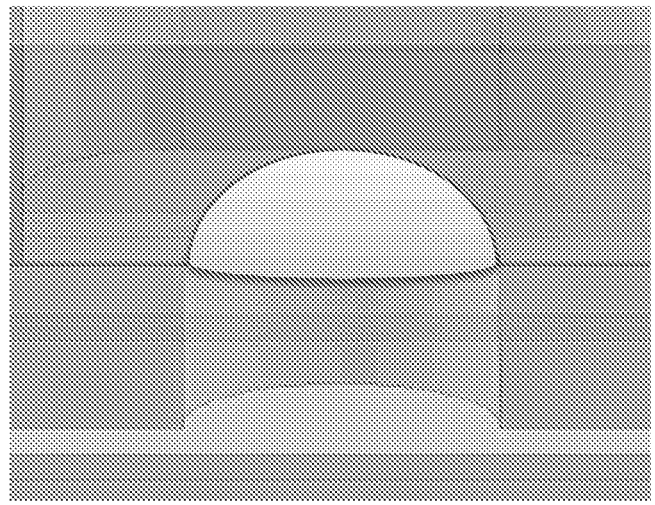
FIGS. 93A and 93B are schematic illustrations of membrane inflation (FIG. 93A) and deflation (FIG. 93B) that can occur in an alveolar device.
Figure 93B:
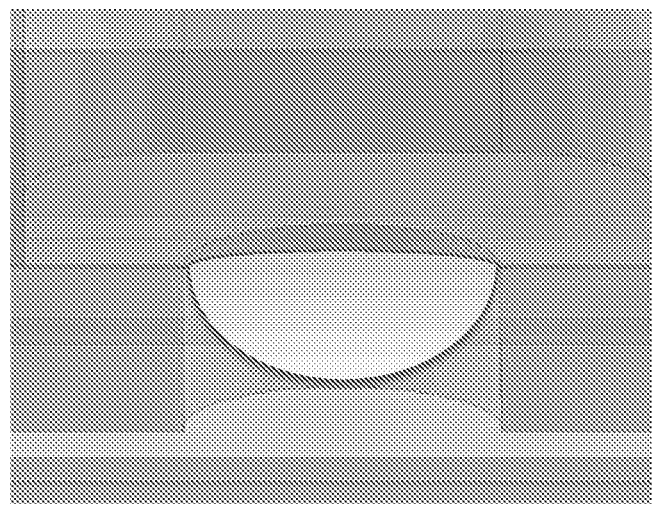
Figure 94A:
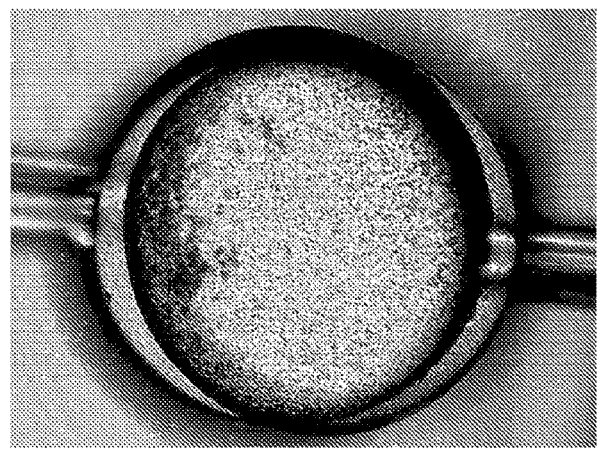
FIGS. 94A-94D show cell populations grown on a membrane material of an alveolar device embodiment.
Figure 94B:
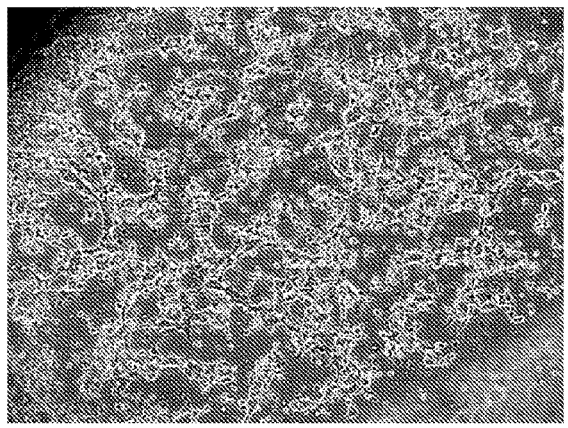
Figure 94C:
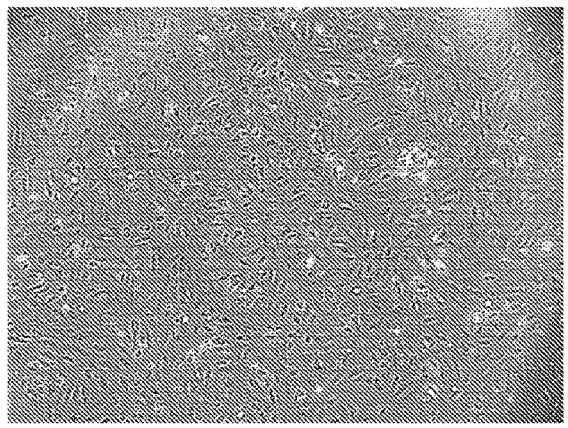
Figure 94D:
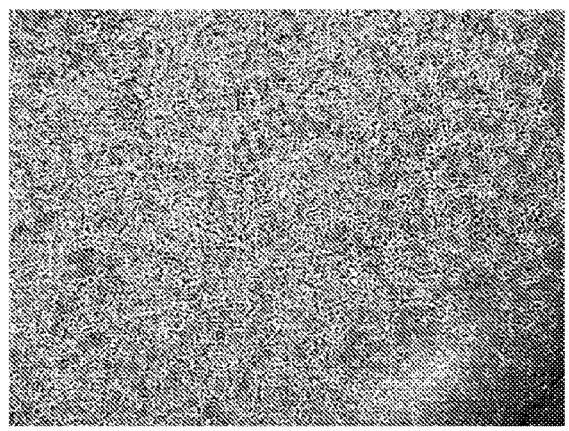

In some embodiments, the mechanical stretch of the membrane of the alveolar device can be tested using a mechanical stretching device, such as the device illustrated in FIGS. 91 and 92. This device can be used to test whether a particular material (such as any membrane materials disclosed herein for use with the alveolar device) is suitable for use in the alveolar device). As illustrated in FIG. 91, the mechanical stretching device 2200 includes a plurality of medium chambers 2202 in a platform 2204 and a device cover 2206. FIG. 92 illustrates a top view of platform 2204. The device includes an air inlet and outlet located on one end of the device, with the other end of the device being blocked. A membrane material (e.g., PDMS) can be used with the mechanical stretching device to detect the ability of the membrane to inflate as air is injected (FIG. 93A) and deflate as air is withdrawn (FIG. 93B).

Example 6

Cells were seeded onto a membrane component of an alveolar device by coating the basolateral side of a poly-L-lactide acid membrane with HLMVE cells and the apical side of poly-L-lactide acid membrane with AT2 cells for four days. Images of the cell populations are provided by FIGS. 94A-94D. The seeding density for both the HLMVE and AT2 cells was $1 \times 10^6$ cells/cm$^2$.

Example 7

Figure 95A:
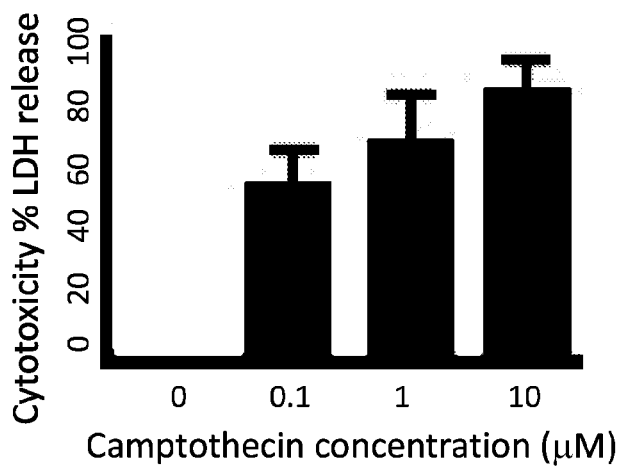
FIG. 95A is a graph of camptothecin concentration (µM) vs. cytotoxicity (% LDH release) illustrating the cytotoxicity of camptothecin as measured after having passed through the bronchiolar device.
Figure 95B:
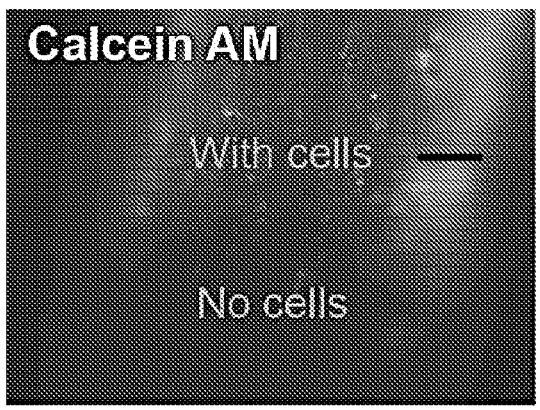
Figure 95C:
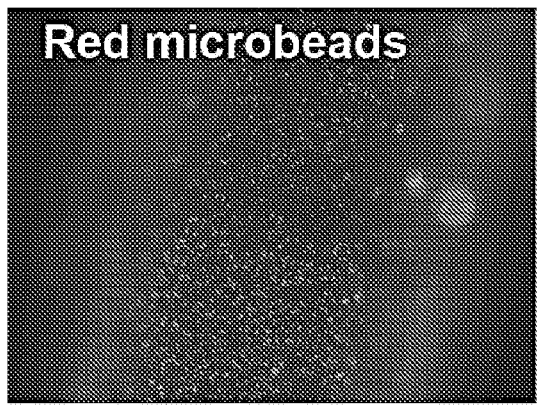
Figure 95D:
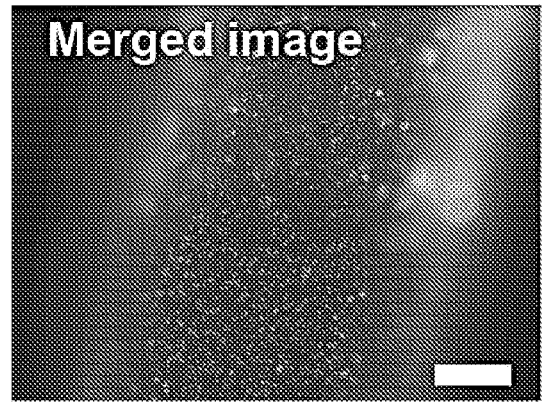

The ability of the disclosed bronchiolar device to test drug toxicity was examined. A bronchiolar device comprising A549 cells was exposed to camptothecin, a pro-apoptotic anti-cancer drug. FLUORESBRITE® Polychromatic Red Microspheres of 0.5 μm diameter (Polysciences) were diluted to $3.64 \times 10^8$ particles/mL using cell culture medium to ensure the better image distinguished when particles deposited in lumen of hollow tube. After the lumen region of hollow fibers (mixed cellulose ester with 0.6 mm of inner diameter and 1 mm of outer diameter) was covered with BEAS-2B cells. The seeding procedure was used with a cell density of $5 \times 10^5$ cells/mL and a flow rate of 1 mL/minute for 30 seconds. After the cell seeding, the bronchiolar device was placed at 37° C. in a 5% CO$_2$ incubator for at least 16 hours to ensure the cell attachment on hollow fiber. The unattached cells were washed out from the hollow fiber with cell culture medium. The continuous medium flow was injected into the bronchiolar device with 10 μL/min flow rate using peristaltic pump. The bronchiolar device was maintained inside an incubator at 37° C. in 5% CO$_2$ for at least 5 days allowing the bronchiolar cells to develop into bronchiolar epithelium tissue. Fluorescent particles were injected into the bronchiolar device through a recirculation system connected to the tubing of the hollow tubes and circulated for 16 h at 10 μL/min of flow rate. A recirculating system connected to medium chamber (outside of the hollow tubes) was maintained at a flow rate of 10 μL/min. Prior to imaging, the bronchiolar device was washed with PBS to remove undeposited or untrapped particles. The treated hollow fibers were recovered by disassembling the device and cell viability was verified using live and dead staining procedure. Representative stained hollow tube(s) were cut longitudinally and imaged using a Zeiss Z1 fluorescent microscope. FIGS. 95B-95D further illustrate that the deposition of fluorescent microbeads (used to detect the camptothecin) decreased in portions of the central lumen where cells were provided in comparison to portions of the central lumen where cells were not present.

Example 8

Drug toxicity was tested using a bronchiolar device as described herein. A pro-apoptotic anti-cancer drug, camptothecin, was chosen to monitor drug toxicity in the bronchiolar device illustrated in FIG. 27. Different concentrations of camptothecin (0.1, 1.0 and 10 µM) were prepared by diluting the original stock solution (2 mg/mL in DMSO) with BEGM culturing medium. After the lumen of a hollow tube of the device was covered with BEAS-2B epithelium, medium in the medium reservoir (which was connected to a maintaining system) was replaced with individual concentrations of the camptothecin medium solution to allow the circulating flow into medium chamber of device. The tubing connected to hollow tube was closed and the recirculating flow rate was set to 10 µL/min to allow camptothecin to diffuse into the bronchiolar epithelium for 48 hours. A drug dose dependence was observed as illustrated by FIG. 95A, which illustrates a graph of camptothecin concentration versus cytotoxicity.

Example 9

In this example, multiple different non-toxic and toxic compounds are evaluated using an embodiment of the lung organ device disclosed herein.

In one embodiment, QVAR® (beclonethasone dipropionate) is evaluated. It is expected that no organ damage will be observed at low doses. After introduction of the agent, the device is assessed for inflammation and clearance, alveolar device ventilation properties, gas exchange efficiency of the alveolar device, and the pH of any blood surrogate used in combination with the lung organ device. In another embodiment, the absorption and clearance of amiodarone (or its desethyl metabolite) can be evaluated. In yet another example, the effects of methamidophos/sulfur mustard and *Bacillus anthracis* (with and without Cipro MCM) are evaluated.

For chemical threat agents, an initial handling protocol and analysis method is applied to test and evaluate the lung organ device using less toxic simulants, such as, but not limited to $^{13}$C- or $^{14}$C-labeled methamidophos (an organophosphorus pesticide), chloroethyl ethyl-sulfide (CEES, half-mustard), and labeled diisopropylfluorophosphate as a chemical reactive surrogate. Subsequently, either $^{13}$C or $^{14}$C-labeled mustard (HD) and soman (GD; O-Pinacolyl methylphosphonofluoridate) are used as chemical agents for validation of the lung organ device, based on results obtained with the surrogate compounds. The lung organ device is then used to investigate any existing or emerging chemical threat in follow-up studies.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A device, comprising:
a first component comprising (i) a first substrate comprising a first plurality of channels, a first inlet, a second inlet, a first outlet fluidly coupled to the first inlet, a second outlet fluidly coupled to the second inlet, and at least two fluid ports, wherein the first plurality of channels are fluidly coupled to the first inlet and to one of the at least two fluid ports; (ii) a second substrate comprising a second plurality of channels, a first fluid port fluidly coupled to the first inlet of the first substrate through at least one fluid port of the first substrate, and a second fluid port fluidly coupled to the second inlet of the first substrate, wherein the plurality of channels are fluidly coupled to the second fluid port; and wherein the first plurality of channels and the second plurality of channels are fluidly coupled and wherein the first inlet and the second inlet of the first substrate are positioned adjacent to one another at the same end of the substrate; and (iii) a bronchiolar membrane comprising a first surface and a second surface, wherein the bronchiolar membrane is positioned between the first substrate and the second substrate such that the first surface of the bronchiolar membrane touches the first substrate and the second surface of the bronchiolar membrane touches the second substrate and wherein the first plurality of channels are arranged in a branching configuration and the second plurality of channels are arranged in a branching configuration that matches that of the first plurality of channels so as to provide two sets of branched channels that have the same branching configuration and that extend along the bronchiolar membrane in a direction parallel to the first and second surfaces of the bronchiolar membrane and wherein each of the first and second plurality of channels are continuously open to the bronchiolar membrane along a length of the first and second plurality of channels so as to provide fluid communication between the bronchiolar membrane and the first and second plurality of channels; and
a second component, comprising an alveolar membrane component comprising an alveolar membrane material coupled to a substrate comprising a plurality of apertures; and
wherein the first component and the second component are fluidly coupled together without any intervening connecting tubes providing the fluid coupling between the first component and the second component.

2. The device of claim 1, wherein the second substrate further comprises:
a third fluid port fluidly coupled to the first outlet of the first substrate; and
a fourth fluid port fluidly coupled to the second outlet of the first substrate.

3. The device of claim 1, wherein the second component further comprises:
a fluid-compatible component comprising:
a plurality of substrates coupled together,
a first fluid inlet fluidly coupled to the first inlet of the first substrate of the first component, and
a first fluid outlet fluidly coupled to the first outlet of the first substrate of the first component; and
a medium-compatible component comprising:
a plurality of substrates coupled together,
a second fluid inlet fluidly coupled to the second inlet of the first substrate of the first component, and
a second fluid outlet fluidly coupled to the second outlet of the first substrate of the first component; and
wherein the alveolar membrane component is positioned between and fluidly coupled to the fluid-compatible component and the medium-compatible component.

4. The device of claim 1, wherein the first substrate is positioned on top of the bronchiolar membrane and the second substrate is placed below the bronchiolar membrane.

5. The device of claim 1, wherein the bronchiolar membrane comprises a porous material.

6. The device of claim 1, wherein the bronchiolar membrane comprises poly-L-lactic acid.

7. The device of claim 1, wherein the bronchiolar membrane comprises an endothelial side that is or can be associated with endothelial cells comprising lung microvascular endothelial cells selected from HLMVE cells and an epithelial side that is or can be associated with epithelial cells selected from BEAS-2B bronchial epithelial cells.

8. The device of claim 1, wherein the bronchiolar membrane includes a plurality of fluid ports that align with one or more of the at least two fluid ports of the first substrate of the first component.

9. The device of claim 3, wherein the plurality of substrates of the fluid-compatible component and the medium-compatible component comprises substrates comprising one or more microchannels or nanochannels.

10. The device of claim 1, wherein the alveolar membrane material of the alveolar membrane component is selected to resiliently deform and reform and to allow gas exchange between the fluid-compatible component and the medium-compatible component.

11. The device of claim 3, wherein one side of the membrane material of the alveolar membrane component is associated with a first population of cells comprising immune responsive cells, surfactant-producing cells, or a combination thereof and the other side of the membrane material is associated with a second population of cells comprising pulmonary microvascular cells and wherein the first population of cells is associated with a side of the membrane material of the alveolar membrane component that is fluidly coupled with the fluid-compatible component and the second population of cells is associated with a side of the membrane material of the alveolar membrane component that is fluidly coupled with the medium-compatible component.

12. The device of claim 11, wherein the first population of cells comprises AT1 cells, AT2 cells, or a combination thereof and wherein the second population of cells comprises human lung microvascular endothelial cells, human lung smooth muscle cells, human lung fibroblast cells, monocytes, dendritic cells, or a combination thereof.

13. The device of claim 1, wherein the first component is fluidly coupled to a plurality of second components and the device further comprises a fluid management device fluidly coupled to the device.

14. A method, comprising:
introducing a compound, or composition containing a compound, into the device according to claim 1; and
analyzing a response generated by the device or the platform device after the compound, or composition thereof, has been introduced into the device or the platform device.

15. The method of claim 14, wherein analyzing the response generated by the device comprises detecting an immune response produced by one or more cell populations associated with the bronchiolar membrane of the device.

16. The method of claim 14, further comprising extracting from the device a sample selected from a fluid that passes through the device, a cell sample, a tissue sample, or a combination thereof to determine the presence or amount of at least one compound.

17. The method of claim 14, wherein the method further comprises introducing the sample into a chromatograph, a mass spectrometer, or a combination thereof to detect the compound.

* * * * *